United States Patent
Nageswaran et al.

(10) Patent No.: US 10,045,867 B2
(45) Date of Patent: Aug. 14, 2018

(54) DELIVERY OF MEDICAL DEVICES

(71) Applicant: Covidien LP, Mansfield, MA (US)

(72) Inventors: Ashok Nageswaran, Irvine, CA (US); Michael Losordo, San Juan Capistrano, CA (US); Gabriel Newell, San Francisco, CA (US); Lawrence Farhat, Carlsbad, CA (US)

(73) Assignee: COVIDIEN LP, Mansfield, MA (US)

( * ) Notice: Subject to any disclaimer, the term of this patent is extended or adjusted under 35 U.S.C. 154(b) by 16 days.

(21) Appl. No.: 14/040,489

(22) Filed: Sep. 27, 2013

(65) Prior Publication Data

US 2015/0066129 A1    Mar. 5, 2015

Related U.S. Application Data

(60) Provisional application No. 61/870,755, filed on Aug. 27, 2013.

(51) Int. Cl.
*A61F 2/06* (2013.01)
*A61F 2/962* (2013.01)
(Continued)

(52) U.S. Cl.
CPC ............... *A61F 2/962* (2013.01); *A61F 2/82* (2013.01); *A61F 2/86* (2013.01); *A61F 2/90* (2013.01);
(Continued)

(58) Field of Classification Search
CPC .......... A61F 2/07; A61F 2/2427; A61F 2/243; A61F 2/2433; A61F 2/2436;
(Continued)

(56) References Cited

U.S. PATENT DOCUMENTS 3,416,531 A    12/1968  Edwards
4,364,391 A    12/1982  Toye
(Continued)

FOREIGN PATENT DOCUMENTS

CN    102159157        8/2011
EP       450221  A1   10/1991
(Continued)

OTHER PUBLICATIONS

DuPont Product and Properties Handbook Teflon FEP Jan. 1998, accessed Jan. 14, 2016 from http://ww.rjchase.com/fep_handbook.pdf.*

(Continued)

*Primary Examiner* — Katrina Stransky
*Assistant Examiner* — Kankindi Rwego
(74) *Attorney, Agent, or Firm* — Fortem IP LLP; Matthew Lincicum

(57) ABSTRACT

A stent delivery system can include a core member, a stent engagement member, and a stent. The core member can have a distal segment. The stent engagement member can have a generally tubular body positioned about the core member distal segment and can be rotatably coupled to the core member. The engagement member can include an inner layer that has a first durometer and an outer layer that has a second durometer less than the first durometer. The stent can extend along the core member distal segment such that an inner surface of the stent is engaged by the engagement member outer layer for facilitating rotation of the stent relative to the core member.

18 Claims, 25 Drawing Sheets

(51) Int. Cl.
*A61F 2/95* (2013.01)
*A61F 2/97* (2013.01)
*A61F 2/958* (2013.01)
*A61M 25/00* (2006.01)
*A61F 2/82* (2013.01)
*A61F 2/86* (2013.01)
*A61F 2/92* (2013.01)
*A61F 2/90* (2013.01)

(52) U.S. Cl.
CPC ............... *A61F 2/92* (2013.01); *A61F 2/95* (2013.01); *A61F 2/958* (2013.01); *A61F 2/97* (2013.01); *A61M 25/008* (2013.01); *A61M 25/0053* (2013.01); *A61F 2002/823* (2013.01); *A61F 2002/9505* (2013.01); *A61F 2002/9528* (2013.01); *A61F 2230/0091* (2013.01); *A61F 2250/0018* (2013.01)

(58) Field of Classification Search
CPC .......... A61F 2/2439; A61F 2/95; A61F 2/958; A61F 2/962; A61F 2/966; A61F 2/97; A61F 2002/9505; A61F 2002/9583; A61F 2002/9665; A61F 2250/0018; A61F 2002/9522; A61F 2002/9534; A61F 2/954
See application file for complete search history.

(56) References Cited

U.S. PATENT DOCUMENTS

| | | | |
|---|---|---|---|
| 4,425,919 A | 1/1984 | Alston, Jr. et al. | |
| 4,516,972 A | 5/1985 | Samson | |
| 4,655,771 A | 4/1987 | Wallsten | |
| 4,723,936 A | 2/1988 | Buchbinder et al. | |
| 4,877,031 A | 10/1989 | Conway et al. | |
| 4,990,151 A | 2/1991 | Wallsten | |
| 5,011,478 A | 4/1991 | Cope | |
| 5,026,377 A | 6/1991 | Burton et al. | |
| 5,037,404 A | 8/1991 | Gold et al. | |
| 5,098,393 A | 3/1992 | Amplatz et al. | |
| 5,108,411 A | 4/1992 | McKenzie et al. | |
| 5,147,370 A | 9/1992 | McNamara et al. | |
| 5,178,158 A | 1/1993 | de Toledo | |
| 5,201,316 A | 4/1993 | Pomeranz et al. | |
| 5,209,734 A | 5/1993 | Hurley et al. | |
| 5,279,562 A | 1/1994 | Sirhan et al. | |
| 5,279,596 A | 1/1994 | Castaneda et al. | |
| 5,292,311 A | 3/1994 | Cope | |
| 5,318,032 A | 6/1994 | Lonsbury et al. | |
| 5,318,525 A * | 6/1994 | West | A61B 18/1492 600/585 |
| 5,318,529 A | 6/1994 | Kontos | |
| 5,358,493 A | 10/1994 | Schweich, Jr. et al. | |
| 5,382,259 A | 1/1995 | Phelps et al. | |
| 5,389,087 A | 2/1995 | Miraki | |
| 5,403,292 A | 4/1995 | Ju | |
| 5,437,288 A | 8/1995 | Schwartz et al. | |
| 5,445,646 A | 8/1995 | Euteneuer et al. | |
| 5,454,795 A | 10/1995 | Samson | |
| 5,458,605 A | 10/1995 | Klemm | |
| 5,474,563 A | 12/1995 | Myler et al. | |
| 5,478,349 A * | 12/1995 | Nicholas | A61F 2/958 606/198 |
| 5,484,444 A | 1/1996 | Braunschweiler et al. | |
| 5,496,294 A | 3/1996 | Hergenrother et al. | |
| 5,499,975 A | 3/1996 | Cope et al. | |
| 5,522,822 A | 6/1996 | Phelps et al. | |
| 5,531,721 A | 7/1996 | Pepin et al. | |
| 5,534,007 A * | 7/1996 | St. Germain | A61F 2/95 606/191 |
| 5,545,209 A | 8/1996 | Roberts et al. | |
| 5,554,139 A | 9/1996 | Okajima | |
| 5,569,220 A | 10/1996 | Webster, Jr. | |
| 5,571,135 A | 11/1996 | Fraser et al. | |
| 5,573,520 A | 11/1996 | Schwartz et al. | |
| 5,584,821 A | 12/1996 | Hobbs et al. | |
| 5,599,325 A | 2/1997 | Ju et al. | |
| 5,599,326 A | 2/1997 | Carter | |
| 5,601,539 A | 2/1997 | Corso, Jr. | |
| 5,636,641 A | 6/1997 | Fariabi | |
| 5,645,559 A * | 7/1997 | Hachtman | A61F 2/90 606/198 |
| 5,658,264 A | 8/1997 | Samson | |
| 5,662,622 A | 9/1997 | Gore et al. | |
| 5,676,659 A | 10/1997 | McGurk | |
| 5,695,483 A | 12/1997 | Samson | |
| 5,695,499 A * | 12/1997 | Helgerson | A61F 2/95 606/108 |
| 5,702,373 A | 12/1997 | Samson | |
| 5,702,418 A | 12/1997 | Ravenscroft | |
| 5,704,926 A | 1/1998 | Sutton | |
| 5,709,703 A | 1/1998 | Lukic et al. | |
| 5,711,909 A | 1/1998 | Gore et al. | |
| 5,725,513 A | 3/1998 | Ju et al. | |
| 5,725,571 A | 3/1998 | Imbert et al. | |
| 5,728,063 A | 3/1998 | Preissman et al. | |
| 5,741,429 A | 4/1998 | Donadio, III et al. | |
| 5,743,876 A | 4/1998 | Swanson | |
| 5,759,173 A | 6/1998 | Preissman et al. | |
| 5,776,141 A | 7/1998 | Klein et al. | |
| 5,782,811 A | 7/1998 | Samson et al. | |
| 5,791,036 A * | 8/1998 | Goodin | A61M 25/0014 29/423 |
| 5,824,041 A | 10/1998 | Lenker et al. | |
| 5,833,632 A | 11/1998 | Jacobsen et al. | |
| 5,836,925 A | 11/1998 | Soltesz | |
| 5,836,926 A | 11/1998 | Peterson et al. | |
| 5,851,203 A | 12/1998 | van Muiden | |
| 5,853,400 A | 12/1998 | Samson | |
| 5,873,866 A | 2/1999 | Kondo et al. | |
| 5,876,386 A | 3/1999 | Samson | |
| 5,891,112 A | 4/1999 | Samson | |
| 5,897,529 A | 4/1999 | Ponzi | |
| 5,897,537 A | 4/1999 | Berg et al. | |
| 5,902,290 A | 5/1999 | Peacock, III et al. | |
| 5,906,605 A | 5/1999 | Coxum | |
| 5,935,161 A | 8/1999 | Robinson et al. | |
| 5,938,653 A | 8/1999 | Pepin | |
| 5,951,494 A | 9/1999 | Wang et al. | |
| 5,951,539 A | 9/1999 | Nita et al. | |
| 5,961,510 A | 10/1999 | Fugoso et al. | |
| 5,968,053 A | 10/1999 | Revelas | |
| 5,971,975 A | 10/1999 | Mills et al. | |
| 5,984,963 A | 11/1999 | Loomis et al. | |
| 6,017,323 A | 1/2000 | Chee | |
| 6,030,371 A | 2/2000 | Pursley | |
| 6,045,547 A | 4/2000 | Ren et al. | |
| 6,053,903 A | 4/2000 | Samson | |
| 6,053,904 A | 4/2000 | Scribner et al. | |
| 6,077,258 A | 6/2000 | Lange et al. | |
| 6,077,295 A | 6/2000 | Limon et al. | |
| 6,077,297 A | 6/2000 | Robinson et al. | |
| 6,083,152 A | 7/2000 | Strong | |
| 6,093,177 A | 7/2000 | Javier, Jr. et al. | |
| 6,105,651 A | 8/2000 | Leanna | |
| 6,106,510 A | 8/2000 | Lunn et al. | |
| 6,106,540 A | 8/2000 | White et al. | |
| 6,123,723 A | 9/2000 | Konya et al. | |
| 6,126,685 A | 10/2000 | Lenker et al. | |
| 6,135,992 A | 10/2000 | Wang | |
| 6,149,680 A | 11/2000 | Shelso et al. | |
| 6,152,912 A | 11/2000 | Jansen et al. | |
| 6,152,944 A | 11/2000 | Holman et al. | |
| 6,159,219 A | 12/2000 | Ren | |
| 6,165,163 A | 12/2000 | Chien et al. | |
| 6,165,166 A | 12/2000 | Samuelson et al. | |
| 6,171,295 B1 | 1/2001 | Garabedian et al. | |
| 6,171,296 B1 | 1/2001 | Chow | |
| 6,171,297 B1 | 1/2001 | Pedersen et al. | |
| 6,186,986 B1 | 2/2001 | Berg et al. | |
| 6,193,739 B1 | 2/2001 | Chevillon et al. | |
| 6,197,015 B1 | 3/2001 | Wilson | |
| 6,217,565 B1 | 4/2001 | Cohen | |

(56) References Cited

U.S. PATENT DOCUMENTS

| | | |
|---|---|---|
| 6,217,566 B1 | 4/2001 | Ju et al. |
| 6,251,132 B1 | 6/2001 | Ravenscroft et al. |
| 6,258,080 B1 | 7/2001 | Samson |
| 6,264,683 B1 | 7/2001 | Stack et al. |
| 6,287,315 B1 | 9/2001 | Wijeratne et al. |
| 6,325,807 B1 | 12/2001 | Que |
| 6,350,278 B1 | 2/2002 | Lenker et al. |
| 6,355,027 B1 | 3/2002 | Le et al. |
| 6,358,238 B1 | 3/2002 | Sherry |
| 6,358,460 B1 | 3/2002 | Hunt, Jr. et al. |
| 6,368,316 B1 | 4/2002 | Jansen et al. |
| 6,371,953 B1 | 4/2002 | Beyar et al. |
| 6,383,171 B1 | 5/2002 | Gifford et al. |
| 6,387,118 B1 | 5/2002 | Hanson |
| 6,395,008 B1 | 5/2002 | Ellis et al. |
| 6,395,017 B1 | 5/2002 | Dwyer et al. |
| 6,398,791 B1 | 6/2002 | Que et al. |
| 6,419,693 B1 | 7/2002 | Fariabi |
| 6,425,898 B1 | 7/2002 | Wilson et al. |
| 6,428,552 B1 | 8/2002 | Sparks |
| 6,443,971 B1 | 9/2002 | Boylan et al. |
| 6,458,075 B1 | 10/2002 | Sugiyama et al. |
| 6,464,684 B1 | 10/2002 | Galdonik |
| 6,468,298 B1 | 10/2002 | Pelton |
| 6,475,184 B1 | 11/2002 | Wang et al. |
| 6,494,907 B1 | 12/2002 | Bulver et al. |
| 6,508,804 B2 | 1/2003 | Sarge et al. |
| 6,508,805 B1 | 1/2003 | Garabedian et al. |
| 6,508,806 B1 | 1/2003 | Hoste |
| 6,517,547 B1 | 2/2003 | Feeser et al. |
| 6,554,820 B1 | 4/2003 | Wendlandt et al. |
| 6,562,021 B1 | 5/2003 | Derbin et al. |
| 6,562,063 B1 | 5/2003 | Euteneuer et al. |
| 6,576,006 B2 | 6/2003 | Limon et al. |
| 6,582,460 B1 | 6/2003 | Cryer |
| 6,589,227 B2 | 7/2003 | Sønderskov Klint |
| 6,602,271 B2 | 8/2003 | Adams et al. |
| 6,607,551 B1 * | 8/2003 | Sullivan ............... A61F 2/95 623/1.11 |
| 6,622,367 B1 | 9/2003 | Bolduc et al. |
| 6,635,047 B2 | 10/2003 | Forsberg |
| 6,638,245 B2 | 10/2003 | Miller et al. |
| 6,641,564 B1 | 11/2003 | Kraus |
| 6,648,654 B1 | 11/2003 | Akram et al. |
| 6,648,874 B2 | 11/2003 | Parisi et al. |
| 6,652,508 B2 | 11/2003 | Griffin et al. |
| 6,663,614 B1 | 12/2003 | Carter |
| 6,669,719 B2 | 12/2003 | Wallace et al. |
| 6,689,120 B1 | 2/2004 | Gerdts |
| 6,699,274 B2 | 3/2004 | Stinson |
| 6,702,782 B2 | 3/2004 | Miller et al. |
| 6,706,055 B2 | 3/2004 | Douk et al. |
| 6,716,207 B2 | 4/2004 | Farnholtz |
| 6,726,659 B1 | 4/2004 | Stocking et al. |
| 6,764,504 B2 | 7/2004 | Wang et al. |
| 6,808,529 B2 | 10/2004 | Fulkerson |
| 6,815,325 B2 | 11/2004 | Ishii |
| 6,817,995 B1 | 11/2004 | Halpern |
| 6,830,575 B2 | 12/2004 | Stenzel et al. |
| 6,837,890 B1 | 1/2005 | Chludzinski et al. |
| 6,843,802 B1 | 1/2005 | Villalobos et al. |
| 6,858,024 B1 | 2/2005 | Berg et al. |
| 6,866,660 B2 | 3/2005 | Garabedian et al. |
| 6,866,679 B2 | 3/2005 | Kusleika |
| 6,932,837 B2 | 8/2005 | Amplatz et al. |
| 6,939,353 B2 | 9/2005 | Que et al. |
| 6,945,970 B2 | 9/2005 | Pepin |
| 6,960,227 B2 | 11/2005 | Jones et al. |
| 6,989,024 B2 | 1/2006 | Hebert et al. |
| 7,001,369 B2 | 2/2006 | Griffin et al. |
| 7,011,675 B2 | 3/2006 | Hemerick et al. |
| 7,025,758 B2 | 4/2006 | Klint |
| 7,074,236 B2 | 7/2006 | Rabkin et al. |
| 7,104,979 B2 | 9/2006 | Jansen et al. |
| 7,147,656 B2 | 12/2006 | Andreas et al. |
| 7,163,523 B2 | 1/2007 | Devens, Jr. et al. |
| 7,166,088 B2 | 1/2007 | Heuser |
| 7,166,099 B2 | 1/2007 | Devens, Jr. |
| 7,166,100 B2 | 1/2007 | Jordan et al. |
| 7,172,575 B2 * | 2/2007 | El-Nounou ............ A61F 2/958 428/304.4 |
| 7,228,878 B2 | 6/2007 | Chen et al. |
| 7,306,624 B2 | 12/2007 | Yodfat et al. |
| 7,323,000 B2 | 1/2008 | Monstdt et al. |
| 7,331,948 B2 | 2/2008 | Skarda |
| 7,357,812 B2 | 4/2008 | Andreas et al. |
| 7,371,248 B2 | 5/2008 | Dapolito et al. |
| 7,402,151 B2 | 7/2008 | Rosenman et al. |
| 7,427,288 B2 | 9/2008 | Sater |
| 7,438,712 B2 | 10/2008 | Chouinard |
| 7,445,684 B2 | 11/2008 | Pursley |
| 7,473,271 B2 | 1/2009 | Gunderson |
| 7,473,272 B2 | 1/2009 | Pryor |
| 7,481,804 B2 | 1/2009 | Devens, Jr. |
| 7,507,229 B2 | 3/2009 | Hewitt et al. |
| 7,524,322 B2 | 4/2009 | Monstdt et al. |
| 7,556,634 B2 | 7/2009 | Lee et al. |
| 7,556,710 B2 | 7/2009 | Leeflang et al. |
| 7,569,046 B2 | 8/2009 | Zhou |
| 7,572,290 B2 | 8/2009 | Yodfat et al. |
| 7,582,079 B2 | 9/2009 | Wendlandt et al. |
| 7,597,830 B2 | 10/2009 | Zhou |
| 7,621,904 B2 | 11/2009 | McFerran et al. |
| 7,625,337 B2 | 12/2009 | Campbell et al. |
| 7,641,646 B2 | 1/2010 | Kennedy, II |
| 7,651,520 B2 | 1/2010 | Fischell et al. |
| 7,655,031 B2 | 2/2010 | Tenne et al. |
| 7,674,411 B2 | 3/2010 | Berg et al. |
| 7,691,138 B2 | 4/2010 | Stenzel et al. |
| 7,708,704 B2 | 5/2010 | Mitelberg et al. |
| 7,717,953 B2 | 5/2010 | Kaplan et al. |
| 7,758,624 B2 | 7/2010 | Dorn et al. |
| 7,766,820 B2 | 8/2010 | Core |
| 7,766,896 B2 | 8/2010 | Kornkven Volk et al. |
| 7,780,646 B2 | 8/2010 | Farnholtz |
| 7,815,600 B2 | 10/2010 | Al-Marashi et al. |
| 7,815,608 B2 | 10/2010 | Schafersman et al. |
| 7,815,628 B2 | 10/2010 | Devens, Jr. |
| 7,828,790 B2 | 11/2010 | Griffin |
| 7,867,267 B2 | 1/2011 | Sullivan et al. |
| 7,879,022 B2 | 2/2011 | Bonnette et al. |
| 7,942,925 B2 | 5/2011 | Yodfat et al. |
| 7,955,370 B2 | 6/2011 | Gunderson |
| 7,981,148 B2 | 7/2011 | Aguilar et al. |
| 7,993,385 B2 | 8/2011 | Levine et al. |
| 8,025,692 B2 | 9/2011 | Feeser |
| 8,034,095 B2 | 10/2011 | Randolph et al. |
| 8,042,720 B2 | 10/2011 | Shifrin et al. |
| 8,048,104 B2 | 11/2011 | Monstdt et al. |
| 8,066,754 B2 | 11/2011 | Malewicz |
| 8,083,791 B2 | 12/2011 | Kaplan et al. |
| 8,088,140 B2 | 1/2012 | Ferrera et al. |
| 8,092,508 B2 | 1/2012 | Leynov et al. |
| 8,109,987 B2 | 2/2012 | Kaplan et al. |
| 8,133,266 B2 | 3/2012 | Thomas et al. |
| 8,147,534 B2 | 4/2012 | Berez et al. |
| 8,187,314 B2 | 5/2012 | Davis et al. |
| 8,257,432 B2 | 9/2012 | Kaplan et al. |
| 8,298,276 B2 | 10/2012 | Ozawa et al. |
| 8,317,850 B2 | 11/2012 | Kusleika |
| 8,366,763 B2 | 2/2013 | Davis et al. |
| 8,382,818 B2 | 2/2013 | Davis et al. |
| 8,480,701 B2 | 7/2013 | Monstdt |
| 8,579,958 B2 | 11/2013 | Kusleika |
| 8,591,566 B2 | 11/2013 | Newell et al. |
| 8,597,321 B2 | 12/2013 | Monstdt et al. |
| 8,790,387 B2 | 7/2014 | Nguyen et al. |
| 8,968,383 B1 | 3/2015 | Johnson et al. |
| 9,072,624 B2 | 7/2015 | Brown |
| 2001/0020173 A1 | 9/2001 | Klumb et al. |
| 2001/0027310 A1 | 10/2001 | Parisi et al. |
| 2001/0029362 A1 | 10/2001 | Sirhan et al. |
| 2001/0044591 A1 | 11/2001 | Stevens et al. |
| 2001/0049547 A1 | 12/2001 | Moore |

(56) References Cited

U.S. PATENT DOCUMENTS

| | | |
|---|---|---|
| 2002/0029046 A1 | 3/2002 | Lorentzen Cornelius et al. |
| 2002/0049412 A1 | 4/2002 | Madrid et al. |
| 2002/0072789 A1 | 6/2002 | Hackett et al. |
| 2002/0107526 A1 | 8/2002 | Greenberg et al. |
| 2002/0111666 A1 | 8/2002 | Hart et al. |
| 2002/0138128 A1 | 9/2002 | Stiger et al. |
| 2002/0156459 A1 | 10/2002 | Ye et al. |
| 2002/0156460 A1 | 10/2002 | Ye et al. |
| 2002/0165523 A1 | 11/2002 | Chin et al. |
| 2003/0004539 A1 | 1/2003 | Linder et al. |
| 2003/0009208 A1 | 1/2003 | Snyder et al. |
| 2003/0050600 A1 | 3/2003 | Ressemann et al. |
| 2003/0191451 A1 | 10/2003 | Gilmartin |
| 2003/0212410 A1 | 11/2003 | Stenzel et al. |
| 2003/0212430 A1 | 11/2003 | Bose et al. |
| 2004/0024416 A1 | 2/2004 | Yodfat et al. |
| 2004/0092879 A1 | 5/2004 | Kraus et al. |
| 2004/0111095 A1 | 6/2004 | Gordon et al. |
| 2004/0143239 A1 | 7/2004 | Zhou et al. |
| 2004/0147903 A1 | 7/2004 | Latini |
| 2004/0158230 A1 | 8/2004 | Hunn et al. |
| 2004/0181174 A2 | 9/2004 | Davis et al. |
| 2004/0193140 A1 | 9/2004 | Griffin et al. |
| 2004/0193243 A1 | 9/2004 | Mangiardi et al. |
| 2004/0220585 A1 | 11/2004 | Nikolchev |
| 2004/0230285 A1 | 11/2004 | Gifford et al. |
| 2004/0260271 A1 | 12/2004 | Huyser et al. |
| 2004/0260384 A1 | 12/2004 | Allen |
| 2005/0033403 A1 | 2/2005 | Ward et al. |
| 2005/0070794 A1 | 3/2005 | Deal et al. |
| 2005/0090802 A1 | 4/2005 | Connors et al. |
| 2005/0096724 A1 | 5/2005 | Stenzel et al. |
| 2005/0119719 A1 | 6/2005 | Wallace et al. |
| 2005/0125051 A1 | 6/2005 | Eidenschink et al. |
| 2005/0131449 A1 | 6/2005 | Salahieh et al. |
| 2005/0143773 A1 | 6/2005 | Abrams et al. |
| 2005/0149160 A1 | 7/2005 | McFerran et al. |
| 2005/0182388 A1 | 8/2005 | Garabedian et al. |
| 2005/0182475 A1 | 8/2005 | Jen et al. |
| 2005/0228361 A1 | 10/2005 | Tremaglio |
| 2005/0240254 A1 | 10/2005 | Austin |
| 2005/0273149 A1 | 12/2005 | Tran et al. |
| 2005/0277949 A1 | 12/2005 | Que et al. |
| 2006/0030835 A1 | 2/2006 | Sherman et al. |
| 2006/0036309 A1 | 2/2006 | Hebert et al. |
| 2006/0058865 A1 | 3/2006 | Case et al. |
| 2006/0064123 A1 | 3/2006 | Bonnette et al. |
| 2006/0074477 A1 | 4/2006 | Berthiaume et al. |
| 2006/0089618 A1 | 4/2006 | McFerran et al. |
| 2006/0095050 A1 | 5/2006 | Hartley et al. |
| 2006/0100687 A1 | 5/2006 | Fahey et al. |
| 2006/0116750 A1 | 6/2006 | Hebert et al. |
| 2006/0129166 A1 | 6/2006 | Lavelle |
| 2006/0178698 A1 | 8/2006 | McIntyre et al. |
| 2006/0184226 A1 | 8/2006 | Austin |
| 2006/0212042 A1 | 9/2006 | Lamport et al. |
| 2006/0217682 A1 | 9/2006 | Stivland et al. |
| 2006/0235502 A1 | 10/2006 | Belluche et al. |
| 2007/0027520 A1 | 2/2007 | Sherburne |
| 2007/0043430 A1 | 2/2007 | Stinson |
| 2007/0049903 A1 | 3/2007 | Jansen et al. |
| 2007/0078504 A1 | 4/2007 | Mialhe |
| 2007/0088323 A1 | 4/2007 | Campbell et al. |
| 2007/0100421 A1 | 5/2007 | Griffin |
| 2007/0117645 A1 | 5/2007 | Nakashima |
| 2007/0129706 A1 | 6/2007 | Katoh et al. |
| 2007/0161956 A1 | 7/2007 | Heuser |
| 2007/0185446 A1 | 8/2007 | Accisano |
| 2007/0203563 A1 | 8/2007 | Hebert et al. |
| 2007/0233224 A1* | 10/2007 | Leynov ............. A61F 2/95 623/1.12 |
| 2007/0239254 A1 | 10/2007 | Chia et al. |
| 2007/0239261 A1 | 10/2007 | Bose et al. |
| 2007/0250039 A1 | 10/2007 | Lobbins et al. |
| 2007/0250040 A1 | 10/2007 | Provost et al. |
| 2007/0255255 A1 | 11/2007 | Shah et al. |
| 2007/0255388 A1 | 11/2007 | Rudakov et al. |
| 2007/0270779 A1 | 11/2007 | Jacobs et al. |
| 2007/0299424 A1 | 12/2007 | Cumming et al. |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0009934 A1 | 1/2008 | Schneider et al. |
| 2008/0015558 A1 | 1/2008 | Harlan |
| 2008/0015678 A1 | 1/2008 | Kaplan et al. |
| 2008/0027528 A1 | 1/2008 | Jagger et al. |
| 2008/0033399 A1 | 2/2008 | Hunn et al. |
| 2008/0033528 A1 | 2/2008 | Satasiya et al. |
| 2008/0051705 A1 | 2/2008 | Von Oepen et al. |
| 2008/0051761 A1 | 2/2008 | Slazas et al. |
| 2008/0071301 A1 | 3/2008 | Matsuura et al. |
| 2008/0077229 A1 | 3/2008 | Andreas et al. |
| 2008/0082083 A1 | 4/2008 | Forde et al. |
| 2008/0091169 A1 | 4/2008 | Heideman et al. |
| 2008/0097398 A1 | 4/2008 | Mitelberg et al. |
| 2008/0108974 A1 | 5/2008 | Yee Roth |
| 2008/0132933 A1 | 6/2008 | Gerber |
| 2008/0140180 A1 | 6/2008 | Dolan et al. |
| 2008/0147001 A1 | 6/2008 | Al-Marashi et al. |
| 2008/0147162 A1 | 6/2008 | Andreas et al. |
| 2008/0177249 A1 | 7/2008 | Heuser et al. |
| 2008/0188865 A1 | 8/2008 | Miller et al. |
| 2008/0188928 A1 | 8/2008 | Salahieh et al. |
| 2008/0221666 A1 | 9/2008 | Licata et al. |
| 2008/0234660 A2 | 9/2008 | Cumming et al. |
| 2008/0234795 A1 | 9/2008 | Snow et al. |
| 2008/0243225 A1 | 10/2008 | Satasiya et al. |
| 2008/0255541 A1* | 10/2008 | Hoffman ............. A61B 17/3415 604/533 |
| 2008/0255653 A1 | 10/2008 | Schkolnik |
| 2008/0255654 A1 | 10/2008 | Hebert et al. |
| 2008/0262471 A1 | 10/2008 | Warnock |
| 2008/0262472 A1 | 10/2008 | Lunn et al. |
| 2008/0262592 A1 | 10/2008 | Jordan et al. |
| 2008/0275426 A1 | 11/2008 | Holman et al. |
| 2008/0300667 A1 | 12/2008 | Hebert et al. |
| 2008/0312639 A1 | 12/2008 | Weber |
| 2009/0012500 A1 | 1/2009 | Murata et al. |
| 2009/0082609 A1 | 3/2009 | Condado |
| 2009/0105802 A1 | 4/2009 | Henry et al. |
| 2009/0125053 A1 | 5/2009 | Ferrera et al. |
| 2009/0132019 A1 | 5/2009 | Duffy et al. |
| 2009/0138066 A1 | 5/2009 | Leopold et al. |
| 2009/0143849 A1 | 6/2009 | Ozawa et al. |
| 2009/0149835 A1 | 6/2009 | Velasco et al. |
| 2009/0157048 A1 | 6/2009 | Sutermeister et al. |
| 2009/0160112 A1 | 6/2009 | Ostrovsky |
| 2009/0171319 A1 | 7/2009 | Guo et al. |
| 2009/0204196 A1 | 8/2009 | Weber |
| 2009/0240235 A1 | 9/2009 | Murata |
| 2009/0264985 A1 | 10/2009 | Bruszewski |
| 2009/0287182 A1 | 11/2009 | Bishop et al. |
| 2009/0287183 A1 | 11/2009 | Bishop et al. |
| 2009/0287187 A1 | 11/2009 | Legaspi et al. |
| 2009/0287292 A1 | 11/2009 | Becking et al. |
| 2009/0299333 A1 | 12/2009 | Wendlandt et al. |
| 2009/0299449 A1 | 12/2009 | Styrc |
| 2009/0318947 A1 | 12/2009 | Garcia et al. |
| 2010/0020354 A1 | 1/2010 | Ito |
| 2010/0036363 A1 | 2/2010 | Watanabe et al. |
| 2010/0049293 A1 | 2/2010 | Zukowski et al. |
| 2010/0049297 A1 | 2/2010 | Dorn |
| 2010/0057184 A1 | 3/2010 | Randolph et al. |
| 2010/0057185 A1 | 3/2010 | Melsheimer et al. |
| 2010/0069852 A1 | 3/2010 | Kelley |
| 2010/0087913 A1 | 4/2010 | Rabkin et al. |
| 2010/0094258 A1 | 4/2010 | Shimogami et al. |
| 2010/0094394 A1* | 4/2010 | Beach ............. A61F 2/91 623/1.11 |
| 2010/0094395 A1 | 4/2010 | Kellett |
| 2010/0100106 A1 | 4/2010 | Ferrera |
| 2010/0160863 A1 | 6/2010 | Heuser |
| 2010/0198334 A1 | 8/2010 | Yodfat et al. |
| 2010/0204770 A1 | 8/2010 | Mas et al. |

(56) References Cited

U.S. PATENT DOCUMENTS

| | | |
|---|---|---|
| 2010/0217235 A1 | 8/2010 | Thorstenson et al. |
| 2010/0256602 A1 | 10/2010 | Lippert et al. |
| 2010/0256603 A1 | 10/2010 | Lippert et al. |
| 2010/0262157 A1 | 10/2010 | Silver et al. |
| 2010/0268243 A1 | 10/2010 | Parker |
| 2010/0268328 A1 | 10/2010 | Stiger |
| 2010/0274270 A1 | 10/2010 | Patel et al. |
| 2010/0298931 A1 | 11/2010 | Quadri et al. |
| 2010/0331951 A1 | 12/2010 | Bei et al. |
| 2011/0009943 A1 | 1/2011 | Paul et al. |
| 2011/0022157 A1 | 1/2011 | Essinger et al. |
| 2011/0029065 A1 | 2/2011 | Wood et al. |
| 2011/0034987 A1 | 2/2011 | Kennedy |
| 2011/0054586 A1 | 3/2011 | Mayberry et al. |
| 2011/0093055 A1 | 4/2011 | Kujawski |
| 2011/0098804 A1 | 4/2011 | Yeung et al. |
| 2011/0106235 A1 | 5/2011 | Haverkost et al. |
| 2011/0112623 A1 | 5/2011 | Schatz |
| 2011/0152760 A1 | 6/2011 | Parker |
| 2011/0160763 A1 | 6/2011 | Ferrera et al. |
| 2011/0178588 A1 | 7/2011 | Haselby |
| 2011/0190862 A1 | 8/2011 | Bashiri et al. |
| 2011/0190865 A1 | 8/2011 | McHugo et al. |
| 2011/0208292 A1 | 8/2011 | Von Oepen et al. |
| 2011/0224650 A1 | 9/2011 | Itou et al. |
| 2011/0288626 A1* | 11/2011 | Straubinger .......... A61F 2/2436 623/1.12 |
| 2011/0319904 A1 | 12/2011 | Hollett et al. |
| 2012/0029607 A1 | 2/2012 | McHugo et al. |
| 2012/0035700 A1 | 2/2012 | Leanna et al. |
| 2012/0053681 A1 | 3/2012 | Alkhatib et al. |
| 2012/0059449 A1 | 3/2012 | Dorn et al. |
| 2012/0065660 A1 | 3/2012 | Ferrera et al. |
| 2012/0116494 A1 | 5/2012 | Leynov et al. |
| 2012/0123511 A1 | 5/2012 | Brown |
| 2012/0253447 A1 | 10/2012 | Hayasaka et al. |
| 2012/0316638 A1 | 12/2012 | Grad et al. |
| 2013/0085562 A1 | 4/2013 | Rincon et al. |
| 2013/0131775 A1 | 5/2013 | Hadley et al. |
| 2013/0172925 A1 | 7/2013 | Garcia et al. |
| 2013/0172979 A1 | 7/2013 | Fargahi |
| 2013/0226276 A1 | 8/2013 | Newell et al. |
| 2013/0226278 A1 | 8/2013 | Newell et al. |
| 2013/0261730 A1 | 10/2013 | Bose et al. |
| 2013/0274618 A1 | 10/2013 | Hou et al. |
| 2013/0274859 A1 | 10/2013 | Argentine |
| 2013/0282099 A1 | 10/2013 | Huynh |
| 2013/0304185 A1 | 11/2013 | Newell et al. |
| 2014/0025150 A1 | 1/2014 | Lim |
| 2014/0031918 A1 | 1/2014 | Newell et al. |
| 2014/0148893 A1 | 5/2014 | Kusleika |
| 2014/0171826 A1 | 6/2014 | Lampropoulis et al. |
| 2014/0172067 A1 | 6/2014 | Brown et al. |
| 2014/0194919 A1 | 7/2014 | Losordo et al. |
| 2014/0200648 A1 | 7/2014 | Newell et al. |
| 2015/0032198 A1 | 1/2015 | Folk |
| 2015/0066128 A1 | 3/2015 | Losordo et al. |
| 2015/0066129 A1 | 3/2015 | Nageswaran et al. |
| 2015/0066130 A1 | 3/2015 | Haggstrom et al. |
| 2015/0066131 A1 | 3/2015 | Luong et al. |
| 2015/0080937 A1 | 3/2015 | Davidson |
| 2015/0133990 A1 | 5/2015 | Davidson |
| 2015/0164666 A1 | 6/2015 | Johnson et al. |
| 2015/0238336 A1 | 8/2015 | Johnson et al. |
| 2017/0035592 A1 | 2/2017 | Haggstrom |

FOREIGN PATENT DOCUMENTS

| | | | |
|---|---|---|---|
| EP | 775470 | | 5/1997 |
| EP | 1637176 | | 3/2006 |
| EP | 1637176 | A1 | 3/2006 |
| EP | 1656963 | A1 | 5/2006 |
| EP | 1656963 | A1 | 5/2006 |
| EP | 1698369 | A1 | 9/2006 |
| EP | 2 078 512 | | 7/2009 |
| GB | 1449622 | * | 9/1976 |
| GB | 1449622 | A | 9/1976 |
| GB | 2179258 | A | 3/1987 |
| GB | 2179258 | A | 3/1987 |
| JP | 3272716 | B2 | 4/2002 |
| JP | 2005110721 | A | 4/2005 |
| JP | 2006021039 | | 1/2006 |
| WO | WO-96/01591 | | 1/1996 |
| WO | WO-2001/007231 | | 2/2001 |
| WO | WO-01/49212 | | 7/2001 |
| WO | WO-01/89619 | | 11/2001 |
| WO | WO-2002/036179 | | 5/2002 |
| WO | WO-2007/095031 | A2 | 8/2007 |
| WO | WO-2007/117645 | | 10/2007 |
| WO | WO-2009/140545 | A2 | 11/2009 |
| WO | WO-2009/140546 | A2 | 11/2009 |
| WO | WO-2010/008571 | A1 | 1/2010 |
| WO | WO-2010/027485 | | 3/2010 |
| WO | WO-2010/086320 | | 8/2010 |
| WO | WO-2010/123831 | | 10/2010 |
| WO | WO-2010/127838 | | 11/2010 |
| WO | WO-2011/014814 | | 2/2011 |
| WO | WO-2011/076408 | | 6/2011 |
| WO | WO-2011/095966 | | 8/2011 |
| WO | WO-2011/144351 | A2 | 11/2011 |
| WO | WO-2012/040240 | | 3/2012 |
| WO | WO-2012/158152 | A1 | 11/2012 |

OTHER PUBLICATIONS

Thermal Tech Equipment Shore Durometer Conversion Chart, accessed Jun. 14, 2016 from http://www.ttequip.com/knowledgelibrary/TechPageShoreDurometerCoversionChart.htm.*

Plastics International Hardness Scale—Durometer Comparisons of Materials 2016, accessed Jun. 14, 2016 from http://www.plasticsintl.com/polyhardness.htm.*

U.S. Appl. No. 13/553,855, filed Jul. 20, 2012.
U.S. Appl. No. 13/664,547, filed Oct. 31, 2012.
U.S. Appl. No. 13/950,950, filed Jul. 25, 2013.
U.S. Appl. No. 14/040,501, filed Sep. 27, 2013.
U.S. Appl. No. 14/040,510, filed Sep. 27, 2013.
U.S. Appl. No. 14/040,516, filed Sep. 27, 2013.
U.S. Appl. No. 14/042,423, filed Sep. 30, 2013.
U.S. Appl. No. 14/076,448, filed Nov. 11, 2013.
Covidien's Pipeline Embolization Device and Delivery System Product Description and Instructions for Use, Jun. 2010.
Misumi, Properties and Characteristics—Polyurethane—Tensile Strength, http://us.misumi-ec.com/maker/misumi/mech/product/ur/detail.html, accessed Apr. 19, 2016.
WS Hampshire Inc., Typical Properties of PTFE—Tensile Strength, http://catalog.wshampshire.com/asset/psg_teflon_ptfe.pdf, accessed Apr. 19, 2016.
Wikipedia, Polyether block amide—Tensile Strength, https://en.wikipedia.org/wiki/polyether_block_amide, accessed Apr. 19, 2016.
DuPont Product and Properties Handbook Teflon FRP Jan. 1998 accessed Jun. 14, 2016 from http:Iwww.rjchase.com/ep_handbook.pdf_.
International Search Report and Written Opinion from PCT/US2014/050270 dated Nov. 18, 2014.
Jankowitz et al. "Measurement of Intracranial Arteries using Digital Subtraction Angiography; with an Internal Control in 85 Patients" University of Pittsburgh Medical Center 2009.
Kim et al. "Sum of the Curve Indices for Estimating the Vascular Tortuousness of the Internal Carotid Arte," Neurointervention 2009; 4: 101-106.
Osborn "Diagnostic Cerebral Angiography 2nd Edition" 1999 Lippincott Williams & Wilkins pp. 3-38 31 57-81 83-116 135-151 173-194.
Plastics International Hardness Scale—Durometer Comparisons of Materials 2016 accessed Jun. 14, 2016 from http:/www.plasticsintl.com/polyhardness.htm.

(56) References Cited

OTHER PUBLICATIONS

Sugawara et al. "Carotid-Femoral Pulse Wave Velocity: Impact of Different Arterial Path Length Measurements" Artery Res Mar. 2010 4 (1) : 27-31.
Thermal tech Equipment Shore Durometer Conversion Chart accessed Jun. 14, 2016 from http:/www.ttequip/knowledgelibraryfTechPageShoreDurometerConversionChart.htm.
International Search Report and Written Opinion dated Jun. 13, 2016; International Application No. PCT/US2016/020382; 12 pages.

* cited by examiner

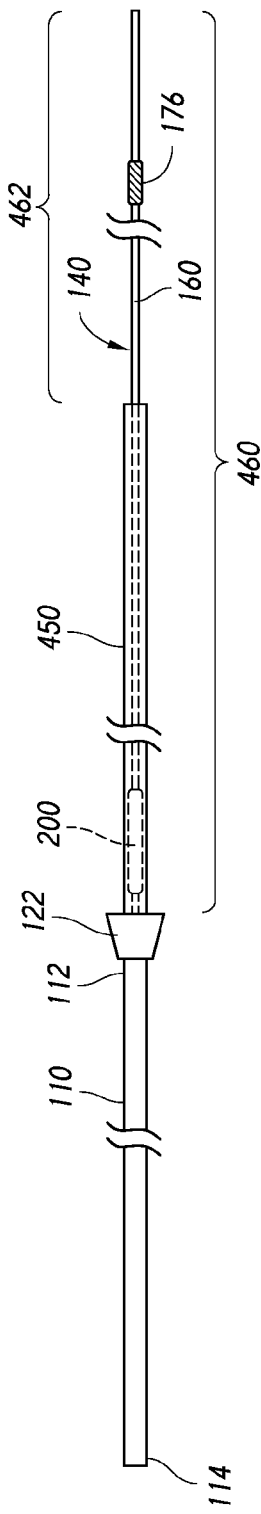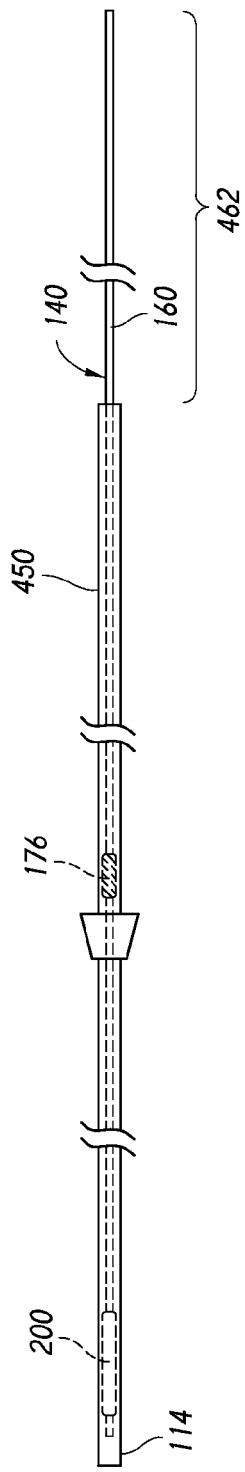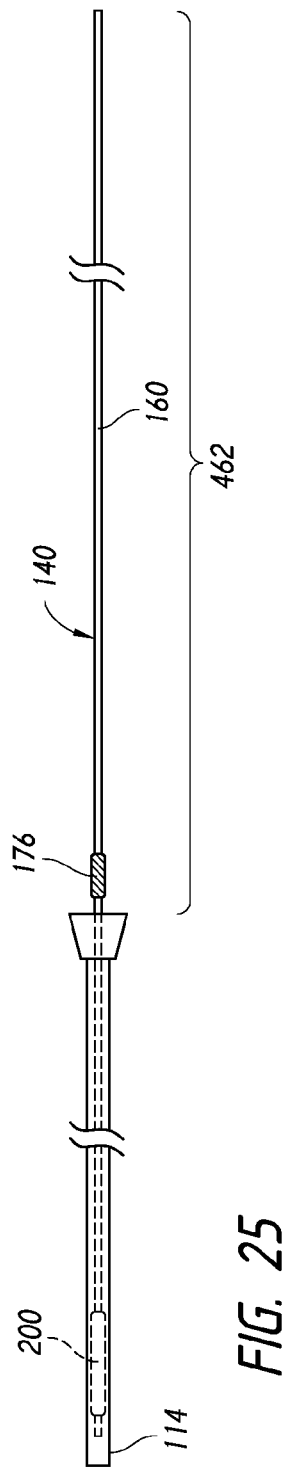

DELIVERY OF MEDICAL DEVICES

CROSS-REFERENCE TO RELATED APPLICATIONS

This application claims the benefit of U.S. Provisional Application No. 61/870,755, filed Aug. 27, 2013, the entirety of which is incorporated herein by reference.

BACKGROUND

Walls of the vasculature, particularly arterial walls, may develop areas of pathological dilatation called aneurysms. As is well known, aneurysms have thin, weak walls that are prone to rupturing. Aneurysms can be the result of the vessel wall being weakened by disease, injury, or a congenital abnormality. Aneurysms could be found in different parts of the body, and the most common are abdominal aortic aneurysms and brain or cerebral aneurysms in the neurovasculature. When the weakened wall of an aneurysm ruptures, it can result in death, especially if it is a cerebral aneurysm that ruptures.

Aneurysms are generally treated by excluding the weakened part of the vessel from the arterial circulation. For treating a cerebral aneurysm, such reinforcement is done in many ways including: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to provide support against the collapse of the vessel. Methods for delivering these intravascular stents are also well known.

In conventional methods of introducing a compressed stent into a vessel and positioning it within in an area of stenosis or an aneurysm, a guiding catheter having a distal tip is percutaneously introduced into the vascular system of a patient. The guiding catheter is advanced within the vessel until its distal tip is proximate the stenosis or aneurysm. A guidewire positioned within an inner lumen of a second, inner catheter and the inner catheter are advanced through the distal end of the guiding catheter. The guidewire is then advanced out of the distal end of the guiding catheter into the vessel until the distal portion of the guidewire carrying the compressed stent is positioned at the point of the lesion within the vessel. Once the compressed stent is located at the lesion, the stent may be released and expanded so that it supports the vessel.

SUMMARY

At least one aspect of the disclosure provides methods and apparatuses for delivering an occluding device or devices (e.g., stent or stents) in the body. The occluding device can easily conform to the shape of the tortuous vessels of the vasculature. The occluding device can be used in a variety of applications. For example, in some embodiments, the occluding device can direct the blood flow within a vessel away from an aneurysm. Additionally, such an occluding device can allow adequate blood flow to be provided to adjacent structures such that those structures, whether they are branch vessels or oxygen demanding tissues, are not deprived of the necessary blood flow.

The delivery of an intravascular stent to a treatment site within the vessel of a patient requires substantial precision. Generally, during the implantation process, a stent is passed through a vessel to a treatment location. The stent can be expanded at the treatment location, often by allowing a first end of the stent to expand and thereafter slowly expanding the remainder of the stent until the entire stent has been expanded. The process of initially contacting the vessel wall as the first end of the stent expands can be referred to as "landing" the stent. The final position of the stent within the vessel is generally determined by its initial placement or landing within the vessel. In some situations, the stent may initially be "landed" in a suboptimal location within the vessel. Using traditional methods and apparatuses, it may be very difficult for a clinician to reposition the stent within the vessel. For example, a clinician may be unable to recapture, collapse, withdraw, or resheath the stent back into the catheter after the stent has been partially expanded within the vessel. As such, the initial landing is critical to successful placement of the stent.

The subject technology is illustrated, for example, according to various aspects described below. Various examples of aspects of the subject technology are described as numbered embodiments (1, 2, 3, etc.) for convenience. These are provided as examples and do not limit the subject technology. It is noted that any of the dependent embodiments may be combined in any combination with each other or one or more other independent embodiments, to form an independent embodiment. The other embodiments can be presented in a similar manner. The following is a non-limiting summary of some embodiments presented herein:

Embodiment 1. A stent delivery system, comprising:
  a core member having an intermediate portion and an elongate, spiral-cut tube extending proximally of the intermediate portion, the tube having first and second flex zones, the second flex zone being proximal of the first flex zone, and a transition zone between the first and second flex zones;
  the first flex zone having a bending stiffness of less than 12 N*mm^2 so as to be navigable through the internal carotid artery bifurcation, the spiral cut of the tube in the first flex zone having a first pitch;
  the second flex zone having a bending stiffness of greater than 60 N*mm^2, the spiral cut of the tube in the second flex zone having a second pitch different from the first pitch;
  wherein the spiral cut of the tube in the transition zone changes from the first pitch to the second pitch in a series of pitch transitions, the spiral cut pitch in the transition zone increasing by an overall percent increase from the first pitch to the second pitch, such that the average overall percent increase achieved per transition is 15% or less; and
  a stent carried by the intermediate portion.

Embodiment 2. The system of Embodiment 1, wherein the pitch transitions of the spiral cut of the tube have a density along the transition zone greater than 1 transition per centimeter.

Embodiment 3. The system of Embodiment 1, wherein the pitch of the spiral cut of the tube increases by over 150% from the first pitch to the second pitch in a proximal direction in the transition zone.

Embodiment 4. The system of Embodiment 1, wherein the first flex zone length is greater than 60 mm.

Embodiment 5. The system of Embodiment 1, wherein the second flex zone length is greater than 30 mm.

Embodiment 6. The system of Embodiment 1, wherein the second flex zone bending stiffness is 60-100 $N*mm^2$.

Embodiment 7. The system of Embodiment 1, wherein the transition zone comprises about 25 pitch transitions.

Embodiment 8. The system of Embodiment 1, wherein the first flex zone is navigable to the M1 bifurcation.

Embodiment 9. The system of Embodiment 8, wherein the second flex zone is navigable to the common carotid artery.

Embodiment 10. The system of Embodiment 1, further comprising a second transition zone distal of the first flex zone, the spiral cut of the tube in the second transition zone decreasing from the second pitch in a second series of pitch transitions, the second series of pitch transitions having a density along the second transition zone greater than five transitions per centimeter.

Embodiment 11. The system of Embodiment 1, wherein a distal end of the first flex zone is spaced 8-12 mm from a proximal end of the stent.

Embodiment 12. The system of Embodiment 11, wherein a distal end of the second flex zone is spaced 225-275 mm from a proximal end of the stent.

Embodiment 13. The system of Embodiment 1, wherein the spiral cut of the tube prevails along a cut length of the tube, the cut length being greater than 50 cm.

Embodiment 14. The system of Embodiment 13, wherein the spiral cut is contiguous along the cut length.

Embodiment 15. The system of Embodiment 13, further comprising a polymeric outer layer disposed over the outer surface of the tube along at least a portion of the cut length, wherein the spiral cut is not cut into the polymeric outer layer.

Embodiment 16. The system of Embodiment 15, wherein the polymeric outer layer covers the entire cut length of the tube.

Embodiment 17. A stent delivery system, comprising:
a core member having an intermediate portion and an elongate, spiral-cut tube extending proximally of the intermediate portion, the tube having an uncut-tube bending stiffness and a first flex zone located near a distal end of the tube, and a transition zone extending proximally from the first flex zone;
the first flex zone having a bending stiffness of less than 5% of the uncut-tube bending stiffness so as to be navigable through the carotid siphon, the spiral cut of the tube in the first flex zone having a first pitch;
wherein the spiral cut of the tube in the transition zone increases from the first pitch in a proximal direction in a series of pitch transitions, the spiral cut pitch in the transition zone increasing by an overall percent increase from the first pitch, such that the average overall percent increase achieved per transition is 15% or less; and
a stent carried by the intermediate portion.

Embodiment 18. The system of Embodiment 17, wherein the pitch transitions of the spiral cut of the tube have a density along the transition zone greater than 1 transition per centimeter.

Embodiment 19. The system of Embodiment 17, wherein the pitch of the spiral cut of the tube increases by over 150% from the first pitch in a proximal direction in the transition zone.

Embodiment 20. The system of Embodiment 17, wherein the first flex zone length is greater than 60 mm.

Embodiment 21. The system of Embodiment 17, wherein the transition zone comprises about 25 pitch transitions.

Embodiment 22. The system of Embodiment 17, wherein the first flex zone is navigable to the M1 bifurcation.

Embodiment 23. The system of Embodiment 17, further comprising a second transition zone distal of the first flex zone, the spiral cut of the tube in the second transition zone decreasing from the second pitch in a second series of pitch transitions, the second series of pitch transitions having a density along the second transition zone greater than five transitions per centimeter.

Embodiment 24. The system of Embodiment 17, wherein a distal end of the first flex zone is spaced 8-12 mm from a proximal end of the stent.

Embodiment 25. The system of Embodiment 17, wherein the spiral cut of the tube prevails along a cut length of the tube, the cut length being greater than 50 cm.

Embodiment 26. The system of Embodiment 25, wherein the spiral cut is contiguous along the cut length.

Embodiment 27. The system of Embodiment 25, further comprising a polymeric outer layer disposed over the outer surface of the tube along at least a portion of the cut length, wherein the spiral cut is not cut into the polymeric outer layer.

Embodiment 28. The system of Embodiment 27, wherein the polymeric outer layer covers the entire cut length of the tube.

Embodiment 29. The system of Embodiment 17, wherein the tube has an outer diameter of 0.040" or less, and a wall thickness of 0.010" or less.

Embodiment 30. A stent delivery system, comprising:
a core member having an intermediate portion and an elongate, spiral-cut tube extending proximally of the intermediate portion, the tube having first and second flex zones, the second flex zone being proximal of the first flex zone, and a transition zone between the first and second flex zones;
the first flex zone having a bending stiffness of less than 220 $N*mm^2$ so as to be navigable through the aortic arch, the spiral cut of the tube in the first flex zone having a first pitch,
the second flex zone having a bending stiffness of greater than 250 $N*mm^2$, the spiral cut of the tube in the second flex zone having a second pitch different from the first pitch,
wherein the spiral cut of the tube in the transition zone changes from the first pitch to the second pitch in a series of pitch transitions, the spiral cut pitch in the transition zone increasing by an overall percent increase from the first pitch to the second pitch, such that the average overall percent increase achieved per transition is 10% or less; and
a stent carried by the intermediate portion.

Embodiment 31. The system of Embodiment 30, wherein the pitch transitions of the spiral cut of the tube have a density along the transition zone greater than 1 transition per centimeter.

Embodiment 32. The system of Embodiment 30, wherein the pitch of the spiral cut of the tube increases by over 35% from the first pitch to the second pitch in a proximal direction in the transition zone.

Embodiment 33. The system of Embodiment 30, wherein the first flex zone length is greater than 200 mm.

Embodiment 34. The system of Embodiment 30, wherein the second flex zone length is greater than 30 mm.

Embodiment 35. The system of Embodiment 30, wherein the second flex zone bending stiffness is 250-310 $N*mm^2$.

Embodiment 36. The system of Embodiment 30, wherein the transition zone comprises about 8 pitch transitions.

Embodiment 37. The system of Embodiment 30, wherein a distal end of the first flex zone is spaced 480-540 mm from a proximal end of the stent.

Embodiment 38. The system of Embodiment 37, wherein a distal end of the second flex zone is spaced 780-820 mm from a proximal end of the stent.

Embodiment 39. The system of Embodiment 30, wherein the spiral cut of the tube prevails along a cut length of the tube, the cut length being greater than 50 cm.

Embodiment 40. The system of Embodiment 39, wherein the spiral cut is contiguous along the cut length.

Embodiment 41. The system of Embodiment 39, further comprising a polymeric outer layer disposed over the outer surface of the tube along at least a portion of the cut length, wherein the spiral cut is not cut into the polymeric outer layer.

Embodiment 42. The system of Embodiment 41, wherein the polymeric outer layer covers the entire cut length of the tube.

Embodiment 43. A stent delivery system, comprising:
  a core member having an intermediate portion and an elongate, spiral-cut tube extending proximally of the intermediate portion, the tube having first and second flex zones, the second flex zone being proximal of the first flex zone, and a transition zone between the first and second flex zones;
  the first flex zone having a bending stiffness of less than 120 N*mm^2 so as to be navigable to the common carotid artery, the spiral cut of the tube in the first flex zone having a first pitch,
  the second flex zone having a bending stiffness of greater than 180 N*mm^2, the spiral cut of the tube in the second flex zone having a second pitch different from the first pitch
  wherein the spiral cut of the tube in the transition zone changes from the first pitch to the second pitch in a series of pitch transitions, the spiral cut pitch in the transition zone increasing by an overall percent increase from the first pitch to the second pitch, such that the average overall percent increase achieved per transition is 10% or less; and
  a stent carried by the intermediate portion.

Embodiment 44. The system of Embodiment 43, wherein the pitch transitions of the spiral cut of the tube have a density along the transition zone greater than 0.5 transitions per centimeter.

Embodiment 45. The system of Embodiment 43, wherein the pitch of the spiral cut of the tube increases by over 80% from the first pitch to the second pitch in a proximal direction in the transition zone.

Embodiment 46. The system of Embodiment 43, wherein the first flex zone length is greater than 50 mm.

Embodiment 47. The system of Embodiment 43, wherein the second flex zone length is greater than 200 mm.

Embodiment 48. The system of Embodiment 43, wherein the second flex zone bending stiffness is 190-210 N*mm^2.

Embodiment 49. The system of Embodiment 43, wherein the transition zone comprises about 10 pitch transitions.

Embodiment 50. The system of Embodiment 43, wherein a distal end of the first flex zone is spaced 300-340 mm from a proximal end of the stent.

Embodiment 51. The system of Embodiment 50, wherein a distal end of the second flex zone is spaced 480-540 mm from a proximal end of the stent.

Embodiment 52. The system of Embodiment 43, wherein the spiral cut of the tube prevails along a cut length of the tube, the cut length being greater than 50 cm.

Embodiment 53. The system of Embodiment 52, wherein the spiral cut is contiguous along the cut length.

Embodiment 54. The system of Embodiment 52, further comprising a polymeric outer layer disposed over the outer surface of the tube along at least a portion of the cut length, wherein the spiral cut is not cut into the polymeric outer layer.

Embodiment 55. The system of Embodiment 54, wherein the polymeric outer layer covers the entire cut length of the tube.

Embodiment 56. A stent delivery system, comprising:
  a core member having an intermediate portion and an elongate, spiral-cut tube extending proximally of the intermediate portion, the tube having first, second, and third flex zones and first and second transition zones, the first transition zone between the first and second flex zones, the second transition zone between the second and third flex zones,
  the core member being configured such that (i) a bending stiffness of the first flex zone is greater than a bending stiffness of the second flex zone and a bending stiffness of the third flex zone and (ii) the bending stiffness of the second flex zone is greater than the bending stiffness of the third flex zone, for providing distal pushability of portions of the core member distal to the first flex zone,
  the spiral cut of the tube has (i) a first pitch in the first flex zone, (ii) a second pitch in the second flex zone, (iii) a third pitch in the third flex zone, and (iv) changing in the first transition zone from the first pitch to the second pitch in a series of pitch transitions and (v) in the second transition zone from the second pitch to the third pitch in a series of pitch transitions for preventing buckling of the tube in the first and second transition zones when the tube is pushed; and
  a stent carried by the intermediate portion.

Embodiment 57. The system of Embodiment 56, wherein the spiral cut of the tube prevails along a cut length of the tube, the cut length being greater than 50 cm.

Embodiment 58. The system of Embodiment 57, wherein the spiral cut is contiguous along the cut length.

Embodiment 59. The system of Embodiment 58, further comprising a polymeric outer layer disposed over the outer surface of the tube along at least a portion of the cut length, wherein the spiral cut is not cut into the polymeric outer layer.

Embodiment 60. The system of Embodiment 59, wherein the polymeric outer layer covers the entire cut length of the tube.

Embodiment 61. The system of Embodiment 56, wherein the tube comprises an uncut segment at a distal portion of the tube.

Embodiment 62. A method of operating a stent delivery system, the method comprising:
  inserting a core member comprising a varying-stiffness elongate tube into a tortuous catheter,
  advancing the tube through the tortuous catheter by bending the tube in a transition zone of the tube, thereby forming a curving, non-kinking bend in the transition zone.

Embodiment 63. The method of Embodiment 62, wherein the transition zone is located between two flex zones of the tube.

Embodiment 64. The method of Embodiment 63, wherein one or both flex zones has a substantially constant bending stiffness.

Embodiment 65. The method of Embodiment 62, wherein the tube is spiral-cut along a cut length of the tube, and the cut length is greater than 50 cm.

Embodiment 66. The method of Embodiment 65, wherein the spiral cut of the tube is contiguous along the cut length.

Embodiment 67. The method of Embodiment 62, wherein advancing the tube comprises navigating the tube through the aortic arch.

Embodiment 68. The method of Embodiment 62, wherein advancing the tube comprises navigating the tube through the carotid siphon.

Embodiment 69. The method of Embodiment 62, performed with the core member of any of s 1-Embodiment 61.

Embodiment 70. The method of Embodiment 62, wherein the catheter extends into the internal carotid artery, and advancing the tube comprises navigating a portion of the core member through the internal carotid artery without buckling the tube.

Embodiment 71. A stent delivery system, comprising:
an elongate core member sized for insertion into a blood vessel, the core member configured for advancing a stent toward a treatment location in the blood vessel, the core member comprising a longitudinally extending tube having a helical cut extending along the tube, the helical cut having an axial length of at least 50 cm and being continuous along the axial length.

Embodiment 72. The system of Embodiment 71, wherein the helical cut comprises a void in the shape of a helix that extends along the axial length of the tube, wherein the void is continuous along the axial length.

Embodiment 73. The system of Embodiment 72, wherein the void comprises multiple helical slots.

Embodiment 74. The system of Embodiment 73, wherein the helical slots are arranged in a contiguous, end-to-end manner.

Embodiment 75. The system of Embodiment 74, wherein the void further comprises at least one connection aperture that joins adjacent helical slots.

Embodiment 76. The system of Embodiment 75, wherein the helical slots and the at least one connection aperture together form the continuous void.

Embodiment 77. The system of Embodiment 74, wherein the at least one connection aperture is a circle.

Embodiment 78. The system of Embodiment 77, wherein the at least one connection aperture has a diameter of about 100 microns.

Embodiment 79. The system of Embodiment 77, wherein the at least one connection aperture has a diameter of greater than 50 microns.

Embodiment 80. The system of Embodiment 77, wherein the at least one connection aperture has a diameter at least twice a width of a helical slot.

Embodiment 81. The system of Embodiment 73, wherein each of the helical slots has a slot width of about 25 microns.

Embodiment 82. The system of Embodiment 73, wherein at least one of the helical slots has a slot width of about 70 microns or less.

Embodiment 83. The system of Embodiment 71, wherein the helical cut forms a cut pattern.

Embodiment 84. The system of Embodiment 71, wherein the tube has a diameter of 2.3 mm or less.

Embodiment 85. The system of Embodiment 71, wherein the tube has a wall thickness of 0.010" or less.

Embodiment 86. A stent delivery system comprising a hypotube having an elongate tubular body having a first section and a continuous helical cut extending about the first section, the cut having an axial length of at least 50 cm.

Embodiment 87. The system of Embodiment 86, wherein the cut comprises a plurality of individual helical slots interconnected in an end-to-end manner.

Embodiment 88. The system of Embodiment 87, wherein each individual helical slot has an axial length of less than or equal to about 15 cm.

Embodiment 89. The system of Embodiment 87, wherein adjacent individual helical slots interconnect via an aperture extending through the hypotube, the adjacent individual helical slots extending from the aperture.

Embodiment 90. The system of Embodiment 86, further comprising a second section, proximal to the first section, wherein a proximal end of the cut terminates proximal to the second section.

Embodiment 91. The system of Embodiment 86, wherein the tube further comprises an uncut region distal to the cut.

Embodiment 92. The system of Embodiment 86, wherein a pitch of the helical cut varies over the length of the cut.

Embodiment 93. The system of Embodiment 92, the pitch of the helical cut changes from a first pitch to a second pitch within a longitudinal segment length of about 5 mm or less.

Embodiment 94. The system of Embodiment 92, the pitch of the helical cut changes from a first pitch to a second pitch within a longitudinal segment length of about 3 mm or less.

Embodiment 95. The system of Embodiment 92, the pitch of the helical cut changes from a first pitch to a second pitch within a longitudinal segment length of about 2 mm or less.

Embodiment 96. The system of Embodiment 92, the pitch of the helical cut changes from a first pitch to a second pitch within a longitudinal segment length of about 1.0 mm.

Embodiment 97. The system of Embodiment 92, wherein the pitch of the helical cut changes within a longitudinal distance of about 10 cm or more from an endpoint of the cut.

Embodiment 98. The system of Embodiment 92, wherein the pitch of the helical cut changes within a longitudinal distance of about 20 cm or more from an endpoint of the cut.

Embodiment 99. The system of Embodiment 92, wherein the pitch of the helical cut changes within a longitudinal distance of about 30 cm or more from an endpoint of the cut.

Embodiment 100. The system of Embodiment 92, wherein the pitch of the helical cut changes in magnitude from a first segment to a second segment by 0.2 mm/rotation or less.

Embodiment 101. The system of Embodiment 92, wherein the pitch of the helical cut changes in magnitude from a first segment to a second segment by 0.1 mm/rotation or less.

Embodiment 102. The system of Embodiment 92, wherein the pitch of the helical cut changes in magnitude from a first segment to a second segment by 0.01 mm/rotation or less.

Embodiment 103. The system of Embodiment 92, wherein the pitch of the helical cut changes in magnitude from a first segment to a second segment by 0.005 mm/rotation or less.

Embodiment 104. A method of manufacturing a stent delivery system, the method comprising:
mounting a hypotube in a cutting device having a cutting head;
aligning the hypotube with the cutting head; and
while rotating and axially moving the hypotube relative to the cutting head, cutting the hypotube to form a helically extending cut having an axial length of at least 50 cm.

Embodiment 105. The method of Embodiment 104, wherein the cutting comprises cutting multiple helical slots to form the helically extending cut.

Embodiment 106. The method of Embodiment 105, wherein the cutting comprises cutting the helical slots in a contiguous, end-to-end manner.

Embodiment 107. The method of Embodiment 106, wherein the cutting comprises cutting at least one connection aperture at an end of a helical slot.

Embodiment 108. The method of Embodiment 107, wherein the aligning the cutting head with the at least one connection aperture to begin cutting a subsequent helical slot from the at least one connection aperture.

Embodiment 109. The method of Embodiment 107, wherein the cutting at least one connection aperture comprises cutting a circle at an end of a helical slot.

Embodiment 110. The method of Embodiment 104, further comprising releasing the hypotube and repositioning and remounting the hypotube in the cutting device after completing a cut.

Embodiment 111. The method of Embodiment 110, wherein the repositioning and remounting comprises aligning the cutting head with an end of the cut.

Embodiment 112. The method of Embodiment 110, wherein the cutting the hypotube comprises making three or more contiguous, end-to-end cuts to create the helically extending cut.

Embodiment 113. A method of operating a stent delivery system, the method comprising:
  inserting a core member into a catheter in a tortuous configuration, the core member comprising a longitudinally extending tube having a helical cut extending along the tube, the helical cut having an axial length of at least 50 cm and being continuous along the axial length; and
  pushing the core member through the tortuous catheter; and
  by pushing the core member, causing the tube to flex along the helical cut, thereby facilitating advancement of the core member through the tortuous catheter.

Embodiment 114. The method of Embodiment 113, wherein the core member comprises a plurality of flex zones, and the pushing comprises advancing at least one flex zone across a tortuosity of the catheter such that the tube forms a curving, non-kinking bend across the tortuosity.

Embodiment 115. The method of Embodiment 113, wherein a pitch of the helical cut varies over the length of the cut to provide a variable flexibility to the tube during advancement through the tortuous catheter.

Embodiment 116. The method of Embodiment 113, wherein inserting the core member into the catheter comprises doing so without buckling the tube.

Embodiment 117. The method of Embodiment 113, wherein the tube has an outside diameter of 2.3 mm or less.

Embodiment 118. The method of Embodiment 113, wherein the tube has a wall thickness of 0.010" or less.

Embodiment 119. The method of Embodiment 113, wherein pushing the core member through the catheter comprises moving a stent through the catheter with the core member.

Embodiment 120. The method of Embodiment 119, further comprising releasing the stent from the core member.

Embodiment 121. The method of Embodiment 113, wherein pushing the core member through the tortuous catheter comprises pushing the tube through the tortuous catheter.

Embodiment 122. A method of operating a stent delivery system, the method comprising:
  inserting a core member into a blood vessel of a patient, the core member comprising a longitudinally extending tube having a helical cut extending along the tube and an axial length of at least 50 cm, the helical cut being continuous along the axial length;
  advancing the core member to the internal carotid artery; and
  by advancing the core member, causing the tube to flex along the helical cut, thereby facilitating advancement of the core member to the internal carotid artery.

Embodiment 123. The method of Embodiment 122, further comprising distally advancing the core member through the internal carotid artery to the middle cerebral artery of the patient.

Embodiment 124. The method of Embodiment 122, wherein the core member comprises a plurality of flex zones, and the method further comprises advancing at least one flex zone across the aortic arch such that the tube forms a curving, non-kinking bend across the aortic arch.

Embodiment 125. The method of Embodiment 122, further comprising distally advancing the core member through the carotid siphon.

Embodiment 126. The method of Embodiment 122, wherein the cut length is greater than 60 cm.

Embodiment 127. The method of Embodiment 122, wherein a pitch of the helical cut varies over the length of the cut to provide a variable flexibility to the tube during advancement through the blood vessel.

Embodiment 128. The method of Embodiment 122, wherein advancing the core member to the internal carotid artery comprises doing so without buckling the tube.

Embodiment 129. The method of Embodiment 122, wherein the tube has an outside diameter of 2.3 mm or less.

Embodiment 130. The method of Embodiment 122, wherein the tube has a wall thickness of 0.010" or less.

Embodiment 131. The method of Embodiment 122, wherein advancing the core member comprises moving a stent with the core member.

Embodiment 132. The method of Embodiment 131, further comprising releasing the stent from the core member.

Embodiment 133. The method of Embodiment 122, wherein advancing the core member to the internal carotid artery comprises positioning the tube so that it extends from the aortic arch to the internal carotid artery.

Embodiment 134. The method of Embodiment 122, wherein advancing the core member to the internal carotid artery comprises advancing the tube to the internal carotid artery.

Embodiment 135. A stent delivery system, comprising:
  a core member having a distal segment;
  a stent engagement member positioned along the core member distal segment and coupled to the core member, the engagement member comprising an outer surface; and
  a stent extending along the core member distal segment such that the outer surface of the engagement member engages an inner surface of the stent along at least a portion of only a distal half of the stent for transmitting an axial force from the core member to only the stent distal half.

Embodiment 136. The system of Embodiment 135, wherein an axial force on the core member is transmitted to the stent only through the engagement member.

Embodiment 137. The system of Embodiment 135, wherein a proximal end of the engagement member is positioned distal to a midpoint of the stent such that transmission of a distal axial force allows the engagement member to pull the stent.

Embodiment 138. The system of Embodiment 135, wherein the engagement member is rotatably coupled to the core member.

Embodiment 139. The system of Embodiment 135, wherein the engagement member is positioned in an axial gap between restraints, coupled to the core member, for permitting rotational movement of the engagement member relative to the core member.

Embodiment 140. The system of Embodiment 139, wherein the positioning of the engagement member in the axial gap permits translation movement of the engagement member relative to the core member.

Embodiment 141. The system of Embodiment 135, wherein the engagement member is a first engagement member, and the system further comprises a second stent engagement member coupled to the core member and positioned proximal to the first stent engagement member.

Embodiment 142. The system of Embodiment 141, wherein a distal end of the second stent engagement member is positioned proximal to a midpoint of the stent such that transmission of a distal axial force allows the second stent engagement member to push the stent.

Embodiment 143. The system of Embodiment 141, wherein the second stent engagement member is rotatably coupled to the core member.

Embodiment 144. The system of Embodiment 141, wherein the second stent engagement member is positioned in an axial gap between restraints, coupled to the core member, for permitting rotational movement of the second stent engagement member relative to the core member.

Embodiment 145. The system of Embodiment 144, wherein the positioning of the second stent engagement member in the axial gap permits translation movement of the second stent engagement member relative to the core member.

Embodiment 146. The system of Embodiment 135, wherein the engagement member comprises a generally tubular body.

Embodiment 147. The system of Embodiment 135, further comprising a radially expandable member coupled to the core member proximal to the engagement member, the radially expandable member having a collapsed position and an expanded position, wherein in the expanded position, the radially expandable member is configured to engage a proximal portion of the stent.

Embodiment 148.The system of Embodiment 147, wherein the radially expandable member comprises a balloon coupled to the core member proximal to the engagement member, the balloon being inflatable to engage a proximal portion of the stent.

Embodiment 149. The system of Embodiment 148, wherein the core member comprises an inflation lumen extending axially to the balloon.

Embodiment 150. The system of Embodiment 147, wherein the radially expandable member comprises a wedge component having an outer portion configured to expand radially when the core member is proximally refracted such that the wedge component engages with the stent to transmit a proximal force to the stent.

Embodiment 151. The system of Embodiment 135, further comprising a stent cover component having a first end coupled to the core member distal segment and a second end extending from the first end, the second end configured to at least partially surround at least a distal portion of a stent carried by the stent delivery system.

Embodiment 152. The system of Embodiment 151, wherein the cover component first end is positioned in an axial gap between first and second restraints such that the first end is rotatably coupled to the core member distal segment.

Embodiment 153. The system of Embodiment 151, wherein a distal end of the engagement member is spaced less than 1 mm proximal to the second end of the cover component.

Embodiment 154. The system of Embodiment 151, wherein a distal end of the engagement member is spaced distal to the second end of the cover component such that the second end is configured to at least partially surround a portion of the engagement member.

Embodiment 155. The system of Embodiment 151, wherein a proximal end of the engagement member is positioned adjacent to the second end of the cover component such that the cover component extends longitudinally along an entire length of the engagement member.

Embodiment 156. The system of Embodiment 135, further comprising a catheter having a lumen configured to receive the core member, engagement member, and stent, wherein the stent is radially compressed between an inner surface of the catheter and the outer surface.

Embodiment 157. The system of Embodiment 135, wherein the stent is a self-expanding stent.

Embodiment 158. The system of Embodiment 135, further comprising a retraction-only interface positioned along the core member distal segment proximal of the stent engagement member.

Embodiment 159. The system of Embodiment 158, wherein the retraction-only interface comprises a balloon.

Embodiment 160. The system of Embodiment 158, wherein the retraction-only interface comprises an expandable pad.

Embodiment 161. A stent delivery system, comprising:
    a catheter having a lumen and an inner surface extending along the lumen;
    a core member, extending within the catheter lumen, having a distal segment and a device interface; and
    a stent extending along the core member distal segment, at least a portion of only a distal half of the stent being radially compressed between the interface and the catheter inner surface such that a distal axial force exerted on the core member is transmitted through the interface to pull the stent in a distal direction.

Embodiment 162. The system of Embodiment 161, wherein a proximal end of the interface is positioned distal to a midpoint of the stent.

Embodiment 163. The system of Embodiment 161, wherein the interface comprises a stent engagement member coupled to the distal segment of the core member, the engagement member comprising an outer surface configured to engage an inner surface of the stent.

Embodiment 164. The system of Embodiment 161, wherein the device interface is a first device interface, and the system further comprises a second device interface, proximal to the first device interface, configured to engage the stent along a proximal half thereof.

Embodiment 165. The system of Embodiment 164, wherein the second device interface comprises a second stent engagement member coupled to the distal segment of the core member, the second stent engagement member comprising an outer surface configured to engage an inner surface of the stent.

Embodiment 166. The system of Embodiment 164, wherein the second device interface comprises an expandable member coupled to the core member proximal to the first stent engagement member, the radially expandable member having a collapsed position and an expanded position, wherein in the expanded position, the radially expandable member is configured to engage a proximal portion of the stent.

Embodiment 167. The system of Embodiment 166, wherein the radially expandable member comprises a balloon coupled to the core member proximal to the first stent engagement member, the balloon being inflatable to engage a proximal portion of the stent.

Embodiment 168. The system of Embodiment 164, wherein the second device interface comprises a retraction-only interface.

Embodiment 169. The system of Embodiment 168, wherein the retraction-only interface comprises a balloon.

Embodiment 170. The system of Embodiment 168, wherein the retraction-only interface comprises an expandable pad.

Embodiment 171. The system of Embodiment 161, further comprising a stent cover component having a first end coupled to the core member distal segment and a second end extending from the first end, the second end configured to at least partially surround at least a distal portion of a stent carried by the stent delivery system.

Embodiment 172. The system of Embodiment 171, wherein a distal end of the interface is spaced less than 1 mm proximal to the second end of the cover component.

Embodiment 173. The system of Embodiment 171, wherein a distal end of the interface is spaced distal to the second end of the cover component such that the second end is configured to at least partially surround a portion of the interface.

Embodiment 174. The system of Embodiment 171, wherein a proximal end of the interface is positioned adjacent to the second end of the cover component such that the cover component extends longitudinally along an entire length of the interface.

Embodiment 175. A method of advancing a stent delivery assembly through a tortuous catheter, the method comprising:
 moving a core assembly distally within a lumen of the catheter, the core assembly comprising a stent engagement member that is engaged with at least a portion of a stent along only a distal half of the stent;
 by moving the core assembly, pulling the stent distally within the catheter lumen, the engagement member configured such that friction between the engagement member and the core member is less than friction between the engagement member and the stent.

Embodiment 176. The method of Embodiment 175, wherein the moving comprises causing the stent to rotate with respect to a core member of the core assembly.

Embodiment 177. The method of Embodiment 176, further comprising rotating the core member to steer the core assembly to avoid damaging vasculature adjacent to a treatment site within a blood vessel.

Embodiment 178. The method of Embodiment 175, further comprising applying a proximally oriented retracting force on the core assembly to retract the stent into the catheter after a distal portion of the stent has been expanded outside of the catheter.

Embodiment 179. The method of Embodiment 178, wherein the applying comprises inflating a balloon, coupled to a core member of the core assembly, to engage a proximal portion of the stent prior to applying the proximally oriented force.

Embodiment 180. The method of Embodiment 175, further comprising advancing the core assembly distally until at least a distal portion of the stent extends distally beyond the catheter such that the stent distal portion expands from a collapsed configuration.

Embodiment 181. The method of Embodiment 180, wherein the advancing comprises inflating a balloon, coupled to a core member of the core assembly, to engage a proximal portion of the stent prior to advancing the stent distal portion distally beyond the catheter.

Embodiment 182. The method of Embodiment 181, wherein the advancing comprises, after the stent distal end extends distally beyond the catheter, advancing the stent by transferring a distal pushing force to the stent via the balloon until a proximal portion of the stent is distally beyond the catheter.

Embodiment 183. The method of Embodiment 175, further comprising partially expanding the stent distally of the catheter, and retracting the stent into the catheter with a retraction-only interface.

Embodiment 184. The method of Embodiment 183, wherein pulling the stent distally comprises doing so without applying any substantial distal pulling force to the stent by the retraction-only interface.

Embodiment 185. A stent delivery system, comprising:
 a core member having a first section and a second section distal to the first section, the second section having a bending stiffness per unit length that is less than a bending stiffness per unit length of the first section;
 an introducer sheath having a lumen configured to receive the core member therethrough, the introducer sheath having a length of at least about 80 cm; and
 a microcatheter having a lumen and a proximal end configured to interface with a distal end of the introducer sheath for delivering the core member into the microcatheter lumen.

Embodiment 186. The system of Embodiment 185, wherein the sheath length is equal to or greater than a length of the core member second section.

Embodiment 187. The system of Embodiment 185, wherein the first section has a substantially constant bending stiffness per unit length.

Embodiment 188. The system of Embodiment 185, wherein the sheath length is between about 80 cm and about 150 cm.

Embodiment 189. The system of Embodiment 188, wherein the sheath length is about 106 cm.

Embodiment 190. The system of Embodiment 185, wherein the core member comprises a marker visible through the introducer sheath.

Embodiment 191. The system of Embodiment 190, wherein the marker is disposed along the core member in the first section thereof Embodiment 192. The system of Embodiment 190, wherein the introducer sheath comprises titanium dioxide.

Embodiment 193. The system of Embodiment 185, wherein the core member comprises a solid wire in the first section.

Embodiment 194. The system of Embodiment 185, wherein the core member comprises a hollow tubular member in the second section.

Embodiment 195. The system of Embodiment 194, wherein at least a portion of the hollow tubular member comprises a spiral cut.

Embodiment 196.The system of Embodiment 195, wherein the spiral cut extends along about 60 cm to about 100 cm of a length of the second section.

Embodiment 197. The system of Embodiment 196, wherein the spiral cut extends along about 86 cm of the length of the second section.

Embodiment 198. A stent delivery system, comprising:
- a core member having (i) a stiff section having a first bending stiffness and (ii) a soft section having a second bending stiffness that is less than the first bending stiffness, the second bending stiffness varying spatially along the soft section;
- an introducer sheath covering any portion of the core member having a bending stiffness that is less than the first bending stiffness, the introducer sheath having a length of at least about 80 cm; and
- a microcatheter having a lumen and a proximal end configured to interface with a distal end of the introducer sheath for delivering the core member into the microcatheter lumen.

Embodiment 199. The system of Embodiment 198, wherein the bending stiffness of the stiff section is substantially constant.

Embodiment 200. The system of Embodiment 198, wherein the stiff section is proximal to the soft section.

Embodiment 201. The system of Embodiment 198, wherein the sheath length is between about 80 cm and about 150 cm.

Embodiment 202. The system of Embodiment 201, wherein the sheath length is about 106 cm.

Embodiment 203. A method of manufacturing a stent delivery system, the method comprising:
- providing a core member and an introducer sheath configured to extend over the core member, the core member comprising a stiff proximal section configured to allow a clinician to grasp the core member for advancing the core member relative to the sheath; and
- inserting the core member into the sheath such that the sheath covers any portion of the core member having a bending stiffness less than a bending stiffness of the proximal section and such that only the proximal section is exposed for gripping.

Embodiment 204. The method of Embodiment 203, wherein the inserting comprises advancing the core member into the sheath until a proximal end of the sheath is positioned axially over a distal end of the stiff proximal section.

Embodiment 205. The method of Embodiment 203, wherein the inserting comprises aligning a marker on the core member with a proximal end of the sheath.

Embodiment 206. A method of advancing a stent delivery system, the method comprising:
- positioning a distal end of the stent delivery assembly adjacent to a proximal end of a guide catheter for moving the core member into a lumen of the catheter, the core member comprising a proximal first section and a distal second section that is more flexible than the first section, the stent delivery assembly comprising an introducer sheath extending over the entire distal second section; and
- while grasping a proximal end of the introducer sheath, grasping only the core member first section to apply a distal axial force to advance the core member into the catheter lumen.

Embodiment 207. The method of Embodiment 206, wherein the core member comprises a marker visible through the introducer sheath, the method further comprising advancing the core member into the catheter lumen until the marker reaches a first position visible within the introducer sheath, the first position of the marker corresponding to a position of a stent carried on the core member within the catheter.

Embodiment 208. The method of Embodiment 206, further comprising proximally withdrawing the introducer sheath from over the core member when the marker reaches the first position.

Embodiment 209. A stent delivery system, comprising:
- a core member having a distal segment;
- a stent engagement member having a generally tubular body positioned about the core member distal segment and rotatably coupled to the core member, the engagement member comprising an inner layer having a first durometer and an outer layer having a second durometer less than the first durometer; and
- a stent extending along the core member distal segment such that an inner surface of the stent is engaged by the engagement member outer layer for facilitating rotation of the stent relative to the core member.

Embodiment 210. The system of Embodiment 209, wherein the inner layer comprises a substantially cylindrical inner surface surrounding the core member.

Embodiment 211. The system of Embodiment 209, wherein the inner layer comprises a coil.

Embodiment 212. The system of Embodiment 209, wherein the outer layer comprises a durometer of between about 10 A to about 50 A.

Embodiment 213. The system of Embodiment 212, wherein the outer layer comprises a durometer of between about 15 A to about 40 A.

Embodiment 214. The system of Embodiment 213, wherein the outer layer comprises a durometer of about 20 A.

Embodiment 215. The system of Embodiment 209, wherein the inner layer comprises polyimide and the outer layer comprises silicone.

Embodiment 216. The system of Embodiment 209, wherein the outer layer comprises a substantially cylindrical outer surface for contacting the stent.

Embodiment 217. The system of Embodiment 209, wherein the outer layer comprises a plurality of protrusions for contacting the stent.

Embodiment 218. The system of Embodiment 209, wherein the outer layer is adhered to the inner layer.

Embodiment 219. The system of Embodiment 209, wherein the stent is moveable within a tubular component by virtue of engagement with the engagement member.

Embodiment 220. The system of Embodiment 209, further comprising a sheath having a lumen configured to receive the core member, engagement member, and stent, wherein the stent is radially compressed between an inner surface of the sheath and the engagement member outer layer.

Embodiment 221. The system of Embodiment 220, wherein friction between the engagement member and the stent is greater than friction between the sheath inner surface and the stent.

Embodiment 222. The system of Embodiment 209, wherein the engagement member comprises a pad.

Embodiment 223. The system of Embodiment 209, wherein the stent is a self-expanding stent.

Embodiment 224. A stent delivery system, comprising:
- a core member having a distal segment;
- a stent engagement member positioned about the core member distal segment and rotatably coupled to the core member, the engagement member comprising an inner layer and an outer layer having a durometer of less than 50 A; and a stent extending along the core member distal segment such that an inner surface of the stent is engaged by the engagement member outer layer for facilitating rotation of the stent relative to the core member.

Embodiment 225. The system of Embodiment 224, wherein the inner layer comprises a substantially cylindrical inner surface surrounding the core member.

Embodiment 226. The system of Embodiment 224, wherein the inner layer comprises a coil.

Embodiment 227. The system of Embodiment 224, wherein the outer layer comprises a durometer of between about 10 A to about 50 A.

Embodiment 228. The system of Embodiment 227, wherein the outer layer comprises a durometer of between about 15 A to about 40 A.

Embodiment 229. The system of Embodiment 228, wherein the outer layer comprises a durometer of about 20 A.

Embodiment 230. The system of Embodiment 224, wherein the inner layer comprises a durometer of between about 70 A to about 100 A.

Embodiment 231. The system of Embodiment 224, wherein the inner layer comprises polyimide and the outer layer comprises silicone.

Embodiment 232. A method of manufacturing a stent delivery system, the method comprising:

forming a tubular body of a first material having a first durometer; and dipping the tubular body in a second material to form an outer layer of the second material on the body, wherein the second material, when in solid form, has a second durometer less than the first durometer.

Embodiment 233. The method of Embodiment 232, wherein the forming comprises dipping a wire in the first material to form the tubular body Embodiment 234. The method of Embodiment 233, wherein the dipping the wire comprises dipping the wire in polyimide to form the tubular body.

Embodiment 235. The method of Embodiment 233, wherein the dipping the wire comprises repeatedly dipping the wire such that the tubular body has an outer diameter of from about 0.343 mm to about 0.380 mm.

Embodiment 236. The method of Embodiment 233, wherein the forming comprises selecting a wire having an outer diameter of less than or equal to 0.25 mm.

Embodiment 237. The method of Embodiment 232, wherein the dipping comprises repeatedly dipping the tubular body in the second material such that the outer layer has an outer diameter of about 0.579 mm to about 0.635 mm.

Embodiment 238. The method of Embodiment 232, wherein the dipping comprises dipping the tubular body in silicone, ChronoPrene, Pebax®, or polyurethane.

Embodiment 239. The method of Embodiment 232, further comprising cutting the tubular body to form an engagement member.

Embodiment 240. The method of Embodiment 239, wherein the cutting comprises cutting the tubular body to a length of from about 2.1 mm to about 2.5 mm.

Embodiment 241. The method of Embodiment 239, further comprising positioning the engagement member over a core member of the stent delivery system.

Embodiment 242. A method of advancing a stent delivery assembly through a tortuous catheter, the method comprising:

moving a core assembly distally within a lumen of the catheter;

by moving the core assembly, moving a stent distally within the catheter lumen;

by moving the core assembly, causing the stent, together with and supported on a stent engagement member of the core assembly, to rotate with respect to a core member of the core assembly, the engagement member being configured such that friction between the engagement member and the core member is less than friction between the engagement member and the stent.

Embodiment 243. The method of Embodiment 242, wherein the moving comprises contacting an inner layer of the engagement member with the core member and an outer layer of the engagement member with the stent, wherein the causing the stent to rotate about the core member comprises causing the inner layer to rotate or slide with respect to the core member while the outer layer is substantially stationary with respect to the stent.

Embodiment 244. The method of Embodiment 242, further comprising rotating the core member to steer the core assembly to avoid damaging vasculature adjacent to a treatment site within a blood vessel.

Embodiment 245. The method of Embodiment 242, wherein the moving comprises distally advancing the core assembly through the aortic arch of a patient.

Embodiment 246. A stent delivery system, comprising:

a microcatheter having a lumen with an internal diameter;

a core member having a proximal segment and a distal segment, the proximal segment comprising a hollow, tubular portion having an external diameter such that the tubular portion fills a majority of space in the microcatheter lumen; and a stent carried on the core member distal segment such that distal advancement or proximal withdrawal of the core member results in distal advancement or proximal withdrawal, respectively, of the stent within the microcatheter;

wherein the core member tubular portion provides core member pushability by providing (i) column strength to the core member during distal advancement within the microcatheter and (ii) radial support of the tubular portion against a wall of the microcatheter lumen to reduce buckling tendency of the core member.

Embodiment 247. The system of Embodiment 246, wherein the tubular portion external diameter is between about 60% and about 98% of the microcatheter internal diameter.

Embodiment 248. The system of Embodiment 246, wherein the tubular portion external diameter is between about 75% and about 95% of the microcatheter internal diameter.

Embodiment 249. The system of Embodiment 248, wherein the tubular portion external diameter is between about 90% and about 93% of the microcatheter internal diameter.

Embodiment 250. The system of Embodiment 246, wherein the tubular portion external diameter is between about 0.35 mm to about 0.70 mm.

Embodiment 251. The system of Embodiment 250, wherein the tubular portion external diameter is between about 0.45 mm to about 0.65 mm.

Embodiment 252. The system of Embodiment 251, wherein the tubular portion external diameter is about 0.51 mm.

Embodiment 253. The system of Embodiment 246, wherein the proximal segment comprises a solid core wire coupled to a proximal end of the tubular portion.

Embodiment 254. The system of Embodiment 253, wherein the proximal segment comprises a sheath extending from a proximal end of the distal segment to the proximal end of the tubular portion.

Embodiment 255. The system of Embodiment 254, wherein the proximal segment comprises a solid core wire coupled to a proximal end of the tubular portion and the sheath is bonded to the solid core wire and to a distal end of the tubular portion.

Embodiment 256. The system of Embodiment 254, wherein an assembly of the sheath and the proximal segment has an outer diameter of about 0.61 mm.

Embodiment 257. The system of Embodiment 246, wherein the distal segment comprises a core wire and the proximal segment comprises a tubular member coupled to the core wire.

Embodiment 258. The system of Embodiment 246, wherein the tubular portion comprises a helical cut extending along an axial length of at least 50 cm.

Embodiment 259. A method of advancing a stent delivery system through a torturous microcatheter, the method comprising:
  moving a core assembly distally within a lumen of the microcatheter, the lumen having an internal diameter;
  by moving the core assembly, moving a core member distally within the microcatheter lumen, the core member having a proximal segment and a distal segment, the proximal segment comprising a hollow, tubular portion having an external diameter such that the tubular portion fills a majority of space in the microcatheter lumen;
  by moving the core assembly, forcing the tubular portion into radial contact with a wall of the microcatheter lumen such that the tubular portion is operative to (i) provide column strength to the core member during distal advancement within the microcatheter and (ii) reduce buckling tendency of the core member.

Embodiment 260. The method of Embodiment 259, further comprising distally advancing the core assembly such that a stent carried by the core assembly is permitted to extend out of the microcatheter and expand.

Embodiment 261. The method of Embodiment 260, further comprising proximally retracting the core member prior to releasing the stent such that the stent is recaptured to within the microcatheter.

Embodiment 262. A stent delivery system, comprising:
  a core member having a distal segment;
  first and second restraints coupled to the core member distal segment and axially spaced apart from each other to provide an axial gap, the first and second restraints each having an outer profile that tapers radially inwardly, in a direction away from the gap such that the first restraint tapers in a distal direction and the second restraint tapers in a proximal direction; and
  a stent cover component having a first end positioned in the axial gap between the first and second restraints such that the first end is rotatably coupled to the core member distal segment.

Embodiment 263. The system of Embodiment 262, wherein the stent cover component has at least one second end extending from the first end, the at least one second end being configured to at least partially surround at least a distal portion of a stent carried by the stent delivery system.

Embodiment 264. The system of Embodiment 262, wherein the first end of the stent cover component is formed separately from the core member such that the first end is rotatable about and slidable along the core member between the first and second restraints.

Embodiment 265. The system of Embodiment 262, wherein the first restraint is positioned distally of the second restraint, the first restraint having an outer profile that is less than an outer profile of the second restraint.

Embodiment 266. The system of Embodiment 265, wherein the first restraint has a maximum outer diameter less than a maximum outer diameter of the second restraint.

Embodiment 267. The system of Embodiment 262, wherein the first restraint has a maximum outer diameter less than a maximum cross-sectional profile of the stent cover component.

Embodiment 268. The system of Embodiment 262, further comprising (i) third and fourth restraints rotatably coupled to the core member distal segment and axially spaced apart from each other to provide a second axial gap and (ii) a stent engagement member rotatably coupled to the core member distal segment in the second axial gap between the first and second restraints.

Embodiment 269. The system of Embodiment 268, wherein the stent engagement member is formed separately from the core member such that it can rotate about and slide along the core member between the third and fourth restraints.

Embodiment 270. The system of Embodiment 269, further comprising a stent positioned over and engaged by the stent engagement member such that the stent is freely rotatable about the core member.

Embodiment 271. The system of Embodiment 270, wherein the stent has an inner diameter, the inner diameter of the stent being greater than maximum cross-sectional profiles of the third and fourth restraints.

Embodiment 272. The system of Embodiment 269, further comprising a stent positioned over and engaged by the stent engagement member, the stent having an inner diameter that is greater than maximum cross-sectional profiles of the third and fourth restraints.

Embodiment 273. The system of Embodiment 268, wherein the engagement member has a maximum outer diameter, the maximum outer diameter of the engagement member being greater than maximum cross-sectional profiles of the third and fourth restraints.

Embodiment 274. The system of Embodiment 268, wherein the second axial gap has an axial length that is between about 0.30 mm and about 0.50 mm greater than an axial length of the stent engagement member.

Embodiment 275. The system of Embodiment 274, wherein the axial length of the second axial gap is about 0.40 mm greater than the axial length of the stent engagement member.

Embodiment 276. The system of Embodiment 262, wherein the axial gap has an axial length of between about 0.50 mm and about 0.70 mm.

Embodiment 277. The system of Embodiment 276, wherein the axial length of the axial gap is about 0.60 mm.

Embodiment 278. The system of Embodiment 262, further comprising an introducer sheath having a lumen configured to receive the core member, the first and second restraints, and the stent cover component.

Embodiment 279. A stent delivery system, comprising:
  a core member having a distal segment;
  first and second restraints coupled to the core member distal segment and axially spaced apart from each other to provide an axial gap, the first and second restraints each having an outer profile that tapers radially inwardly in directions away from the gap; and a stent engagement component at least partially disposed in the axial gap between the first and second restraints such that the component is slidably and rotatably coupled to the core member distal segment.

Embodiment 280. The system of Embodiment 279, wherein the stent engagement component comprises a stent cover component having (i) a first end positioned in the axial gap between the first and second restraints such that the first end is rotatably coupled to the core member distal segment and (ii) at least one second end extending from the first end, the at least one second end being configured to at least partially surround at least a distal portion of a stent carried by the stent delivery system.

Embodiment 281. The system of Embodiment 279, wherein the stent engagement component comprises a stent engagement member rotatably coupled to the core member distal segment in the gap between the first and second restraints.

Embodiment 282. The system of Embodiment 281, wherein the first and second restraints have maximum outer cross-sectional profiles that are less than a maximum diameter of the stent engagement member.

Embodiment 283. The system of Embodiment 282, wherein the first and second restraints have different maximum outer cross-sectional profiles.

Embodiment 284. The system of Embodiment 279, further comprising (i) a third restraint spaced apart from the first and second restraints and providing a second axial gap and (ii) a second stent engagement component rotatably coupled to the core member distal segment in the second axial gap.

Embodiment 285. The system of Embodiment 279, further comprising a stent carried by the core member, the stent having an inner diameter that is greater than maximum cross-sectional profiles of the first and second restraints.

Embodiment 286. The system of Embodiment 279, wherein the delivery system comprises a first radiopaque marker, the catheter comprises a second radiopaque marker, the first and second radiopaque markers being longitudinally movable relative to each other and longitudinally alignable with each other such that the system achieves a pre-release position beyond which additional distal advancement of the core member permits release of a stent from the delivery system.

Embodiment 287. The system of Embodiment 286, wherein the first restraint comprises the first radiopaque marker, and a distal portion of the catheter comprises the second radiopaque marker.

Embodiment 288. The system of Embodiment 287, wherein the second radiopaque marker is positioned at the catheter distal end.

Embodiment 289. The system of Embodiment 287, wherein the first restraint is positioned distally of the second restraint.

Embodiment 290. A method of delivering a stent delivery system, the method comprising:

inserting the delivery system into a curved path, the delivery system comprising a catheter, a core member disposed within the catheter, first and second restraints coupled to the core member, a stent engagement component coupled to the core member between the first and second restraints, and a stent having a first portion (i) supported on the stent engagement component and (ii) extending over at least one of the first and second restraints, the first and second restraints each having a longitudinally tapered end;

causing the core member to bend in the curved path, more than the core member could if the first and second restraints were not tapered, without causing the first and second restraints to compress the stent against an inner wall of the catheter.

Embodiment 291. The method of Embodiment 290, wherein the first restraint is positioned distally of the second restraint, the method further comprising advancing the core member until the first restraint is determined to be positioned adjacent to the distal end of the catheter.

Embodiment 292. The method of Embodiment 291, further comprising holding the axial position of the core member relative to the catheter, when the first restraint is determined to be positioned adjacent to the distal end of the catheter, until initial placement of the stent is determined to be correct.

Embodiment 293. The method of Embodiment 291, wherein the delivery system comprises a first radiopaque marker, the catheter comprises a second radiopaque marker longitudinally movable relative to the first radiopaque marker, and the advancing comprises longitudinally aligning the first and second radiopaque markers such that the system achieves a pre-release position beyond which additional distal advancement of the core member permits release of the stent from the delivery system.

Embodiment 294. The method of Embodiment 293, wherein the first restraint comprises the first radiopaque marker, a distal portion of the catheter comprises the second radiopaque marker, and the advancing comprises observing an image of the first radiopaque marker and the second radiopaque marker as the core member is advanced relative to the catheter.

Embodiment 295. The method of Embodiment 294, wherein the second radiopaque marker is positioned at the catheter distal end, and the advancing comprises longitudinally aligning the first restraint with the catheter distal end.

Embodiment 296. The method of Embodiment 291, further comprising advancing the first and second restraints distally of the catheter distal end such that the stent first portion is released and the stent is disengaged from the delivery system.

Embodiment 297. The method of Embodiment 290, wherein the stent first portion undergoes a bend of at least about 30°.

Embodiment 298. The method of Embodiment 290, wherein the causing comprises causing the stent first portion to undergo the bend without causing the first and second restraints to contact an inner surface of the stent.

Embodiment 299. The method of Embodiment 290, wherein the causing comprises causing the stent first portion to undergo a bend of at least about 45° without causing the first and second restraints to compress the stent against the inner wall of the catheter.

Embodiment 300. The method of Embodiment 299, wherein the causing comprises causing the stent first portion to undergo the bend without causing the first and second restraints to contact an inner surface of the stent.

Embodiment 301. The method of Embodiment 290, wherein the causing comprises causing the stent first portion to undergo a bend of at least about 60° without causing the first and second restraints to compress the stent against the inner wall of the catheter.

Embodiment 302. The method of Embodiment 290, wherein the causing comprises causing the stent first portion to undergo a bend of at least about 90° without causing the first and second restraints to compress the stent against the inner wall of the catheter.

Embodiment 303. The method of Embodiment 290, wherein the causing comprises causing the stent first portion to undergo a bend of at least about 110° without causing the first and second restraints to compress the stent against the inner wall of the catheter.

Embodiment 304. The method of Embodiment 290, wherein the delivery system further comprises third and fourth restraints coupled to the core member distally of the first and second restraints, the third and fourth restraints being spaced apart to provide a gap wherein a first end of a stent cover component is coupled to the core member, the stent first portion extending over the first, second, and third restraints, wherein the causing comprises causing the stent first portion to undergo the bend without causing the first, second, and third restraints to compress the stent against the inner wall of the catheter.

Embodiment 305. The method of Embodiment 304, wherein the causing comprises causing the stent first portion to undergo the bend without causing the first, second, and third restraints to contact an inner surface of the stent.

Embodiment 306. The method of Embodiment 290, wherein the causing comprises advancing the core member and the stent through the aortic arch.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

FIGS. 23-25 are side views of a medical device delivery system, illustrating relative positions of a catheter, a sheath, and a core member and a visible guide system, according to some embodiments.

DETAILED DESCRIPTION

Figure 1:
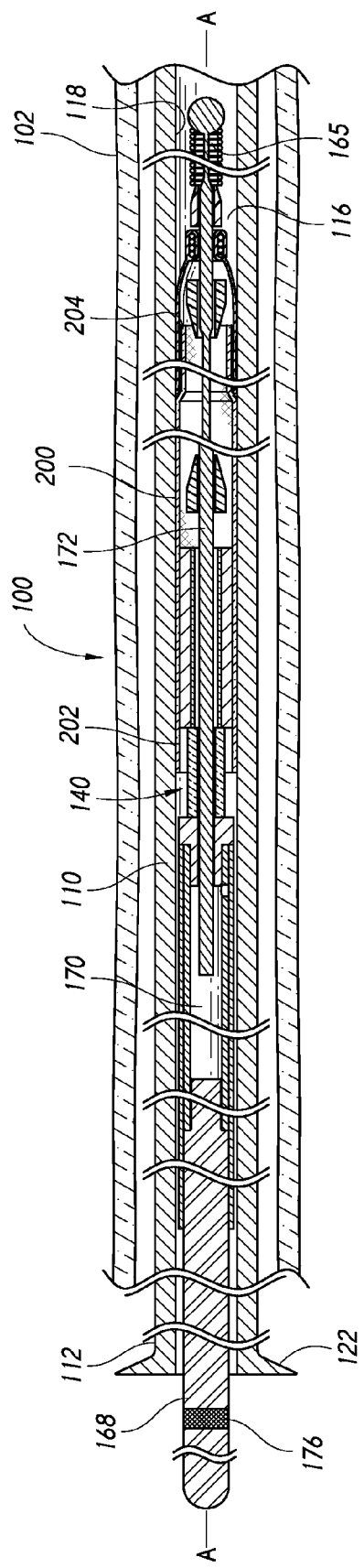
FIG. 1 is a side, cross-sectional view of a medical device delivery system disposed within a body lumen, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

FIGS. 1-8 depict embodiments of a medical device delivery system 100 which may be used to deliver and/or deploy a medical device, such as but not limited to a stent 200, into a hollow anatomical structure such as a blood vessel 102. The stent 200 can comprise a proximal end 202 and a distal end 204. The stent 200 can comprise a braided stent or other form of stent such as a laser-cut stent, roll-up stent, etc. The stent 200 can optionally be configured to act as a "flow diverter" device for treatment of aneurysms, such as those found in blood vessels including arteries in the brain or within the cranium, or in other locations in the body such as peripheral arteries. The stent 200 can optionally be similar to any of the versions or sizes of the PIPELINE™ Embolization Device marketed by Covidien of Mansfield, Mass. USA. The stent 200 can further alternatively comprise any suitable tubular medical device and/or other features, as described herein.

Figure 2:
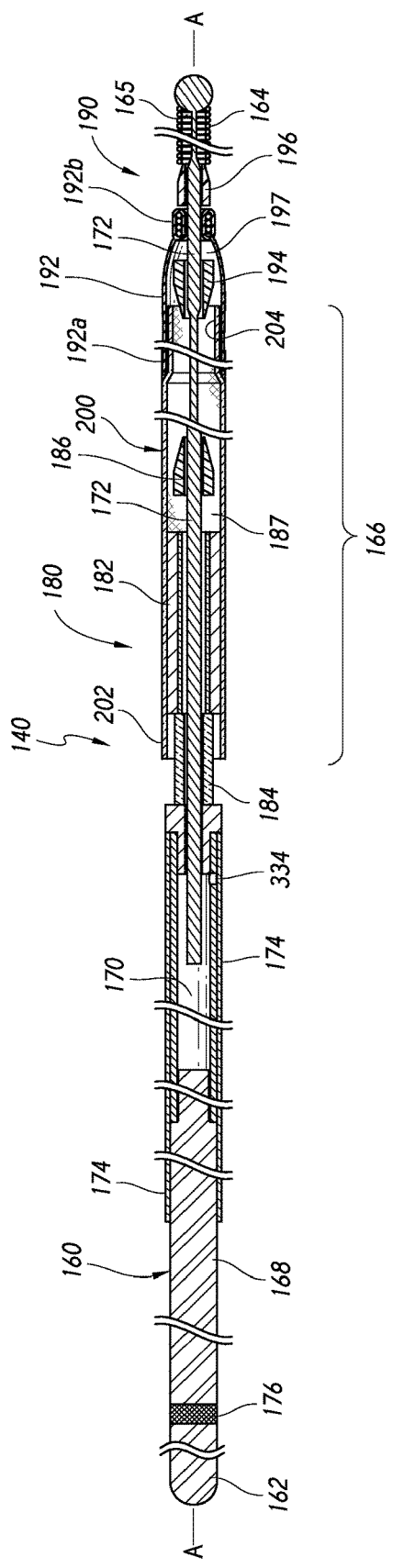
FIG. 2 is a side, cross-sectional view of a core assembly of the medical device delivery system shown in FIG. 1, according to some embodiments.

As shown in FIG. 1, the depicted medical device delivery system 100 can comprise an elongate tube or catheter 110 which slidably receives a core assembly 140 configured to carry the stent 200 through the catheter 110. FIG. 2 illustrates the core assembly 140 without depicting the catheter 110 for clarity. The depicted catheter 110 (see FIGS. 1, 3-8) has a proximal end 112 and an opposing distal end 114 which can be positioned at a treatment site within a patient, an internal lumen 116 extending from the proximal end 112 to the distal end 114, and an inner surface 118 facing the lumen 116. At the distal end 114, the catheter 110 has a distal opening 120 through which the core assembly 140 may be advanced beyond the distal end 114 in order to expand or deploy the stent 200 within the blood vessel 102. The proximal end 112 may include a catheter hub 122. The catheter 110 can define a generally longitudinal axis A-A extending between the proximal end 112 and the distal end 114. When the delivery system 100 is in use, the longitudinal axis need not be straight along some or any of its length.

The catheter 110 can optionally comprise a microcatheter. For example, the catheter 110 can optionally comprise any of the various lengths of the MARKSMAN™ catheter available from Covidien of Mansfield, Mass. USA. The catheter 110 can optionally comprise a microcatheter having an inner diameter of about 0.030 inches or less, and/or an outer diameter of 3 French or less near the distal end 114. Instead of or in addition to these specifications, the catheter 110 can comprise a microcatheter which is configured to percutaneously access the internal carotid artery, or a location within the neurovasculature distal of the internal carotid artery, with its distal opening 120.

Information regarding additional embodiments of the catheter 110, and additional details and components that can optionally be used or implemented in the embodiments of the catheter described herein, can be found in U.S. Patent Application Publication No. US 2011/0238041 A1, published on Sep. 29, 2011, titled Variable Flexibility Catheter. The entirety of the aforementioned publication is hereby incorporated by reference herein and made a part of this specification.

The core assembly 140 can comprise a core member 160 configured to extend generally longitudinally through the lumen 116 of the catheter 110. The core member 160 can have a proximal end or section 162 and a terminal or distal end 164, which can include a tip coil 165. The core member 160 can also comprise an intermediate portion 166 located between the proximal end 162 and the distal end 164, which intermediate portion is the portion of the core member 160 onto or over which the stent 200 is positioned or fitted or extends when the core assembly 140 is in the pre-deployment configuration as shown in FIGS. 1-5.

The core member 160 can generally comprise any member(s) with sufficient flexibility, column strength and thinness to move the stent 200 or other medical device through the catheter 110. The core member 160 can therefore comprise a wire, or a tube such as a hypotube, or a braid, coil, or other suitable member(s), or a combination of wire(s), tube(s), braid(s), coil(s), etc. The embodiment of the core member 160 depicted in FIGS. 1-8 is of multi-member construction, comprising a proximal wire 168, a tube 170 (e.g., a hypotube) connected at its proximal end to a distal end of the proximal wire 168, and a distal wire 172 connected at its proximal end to a distal end of the tube 170. An outer layer 174, which can comprise a layer of lubricious material such as PTFE (polytetrafluoroethylene or TEFLON™) or other lubricious polymers, can cover some or all of the tube 170 and/or proximal wire 168. The proximal and/or distal wires 168, 172 may taper or vary in diameter along some or all of their lengths. The proximal wire 168 may include one or more fluorosafe markers 176, and such marker(s) can be located on a portion of the wire 168 that is not covered by the outer layer 174, e.g., proximal of the outer layer 174. This portion of the wire 168 marked by the marker(s) 176, and/or proximal of any outer layer 174, can comprise a bare metal outer surface.

The core assembly 140 can further comprise a proximal device interface 180 and/or a distal device interface 190 that can interconnect the medical device or stent 200 with the core member 160. The proximal device interface 180 can comprise a proximal engagement member 182 that is configured to underlie the stent 200 and engage an inner wall of the stent. In this manner, the proximal engagement member 182 cooperates with the overlying inner wall 118 of the catheter 110 to grip the stent 200 such that the proximal engagement member 182 can move the stent 200 along and within the catheter 110, e.g., as the user pushes the core member 160 distally and/or pulls the core member proximally relative to the catheter 110, resulting in a corresponding distal and/or proximal movement of the stent 200 within the catheter lumen 116.

The proximal engagement member 182 can be fixed to the core member 160 (e.g., to the distal wire 172 thereof in the depicted embodiment) so as to be immovable relative to the core member 160, either in a longitudinal/sliding manner or a radial/rotational manner. Alternatively, as depicted in FIGS. 1-8, the proximal engagement member 182 can be coupled to (e.g., mounted on) the core member 160 so that the proximal engagement member 182 can rotate about the longitudinal axis A-A of the core member 160 (e.g., of the distal wire 172), and/or move or slide longitudinally along the core member. In such embodiments, the proximal engagement member 182 can have an inner lumen that receives the core member 160 therein such that the proximal engagement member 182 can slide and/or rotate relative to the core member 160. Additionally in such embodiments, the proximal device interface 180 can further comprise a proximal restraint 184 that is fixed to the core member 160 and located proximal of the proximal engagement member 182, and/or a distal restraint 186 that is fixed to the core member 160 and located distal of the proximal engagement member 182. The proximal and distal restraints 184, 186 can be spaced apart along the core member 160 by a longitudinal distance that is greater than the length of the proximal engagement member, so as to leave one or more longitudinal gaps 187 between the proximal engagement member 182 and one or both of the proximal and distal restraints 184, 186, depending on the position of the proximal engagement member between the restraints. When present, the longitudinal gap(s) 187 allow the proximal engagement member 182 to slide longitudinally along the core member 160 between the restraints 184, 186. The longitudinal range of motion of the proximal engagement member 182 between the restraints 184, 186 is approximately equal to the total length of the longitudinal gap(s) 187.

Instead of or in addition to the longitudinal gap(s) 187, the proximal device interface 180 can comprise a radial gap 188 (FIG. 3) between the outer surface of the core member 160 and the inner surface of the proximal engagement member 182. Such a radial gap 188 can be formed when the proximal engagement member 182 is constructed with an inner luminal diameter that is somewhat larger than the outer diameter of the corresponding portion of the core member 160. When present, the radial gap 188 allows the proximal engagement member 182 to rotate about the longitudinal axis A-A of the core member 160 between the restraints 184, 186. The presence of longitudinal gaps 187 of at least a minimal size on either side of the proximal engagement member 182 can also facilitate the rotatability of the proximal engagement member.

One or both of the proximal and distal restraints 184, 186 can have an outside diameter or other radially outermost dimension that is smaller than the outside diameter or other radially outermost dimension of the proximal engagement member 182, so that one or both of the restraints 184, 186 will tend not to contact the inner surface of the stent 200 during operation of the core assembly 140.

In the proximal device interface 180 shown in FIGS. 1-8, the stent 200 can be moved distally or proximally within the catheter 100 via the proximal engagement member 182. During distal movement, the distal end of the proximal restraint 184 bears on the proximal end of the engagement member 182, and the engagement member urges the stent 200 distally via frictional engagement with the inner surface of the stent 200 (assisted by the overlying catheter 110). During proximal movement, the proximal end of the distal restraint 186 bears on the distal end of the engagement member 182, which in turn moves the stent 200 proximally via such frictional engagement. Proximal movement of the stent 200 relative to the catheter 110 can be employed when withdrawing or re-sheathing the stent 200 back into the distal end 114 of the catheter 110, as will be discussed in greater detail below. When the stent 200 has been partially deployed and a portion of the stent remains disposed between the proximal engagement member 182 and the inner wall of the catheter (see FIGS. 6, 7), the stent 200 can be withdrawn back into the distal opening 120 of the catheter by moving the core assembly 140 (including the engagement member 182) proximally relative to the catheter 110 (and/or moving the catheter 110 distally relative to the core assembly 140). Re-sheathing in this manner remains possible until the engagement member 182 and/or catheter 110 have been moved to a point where the engagement member 182 is beyond the distal opening 120 of the catheter 110 and the stent 200 is released from between the member 182 and the catheter 110.

Optionally, the proximal edge of the proximal engagement member 182 can be positioned just distal of the proximal edge of the stent 200 when in the delivery configuration shown in FIGS. 1-5. In some such embodiments, this enables the stent 200 to be re-sheathed when as little as about 3 mm of the stent remains in the catheter 110. Therefore, with stents 200 of typical length, resheathability of 75% or more can be provided (i.e. the stent 200 can be re-sheathed when 75% or more of it has been deployed).

The distal device interface 190 can comprise a distal engagement member 192 that can take the form of, for example, a distal device cover or distal stent cover (generically, a "distal cover"). The distal cover 192 can be configured to reduce friction between the medical device or stent 200 (e.g., the distal portion or distal end thereof) and the inner surface 118 of the catheter 110. For example, the distal cover 192 can be configured as a lubricious, flexible structure having a free first end or section 192a that can extend over at least a portion of the stent 200 and/or intermediate portion 166 of the core assembly 160, and a fixed second end or section 192b that can be coupled (directly or indirectly) to the core member 160.

The distal cover 192 can have a first or delivery position, configuration, or orientation (see, e.g., FIGS. 1-5) in which the distal cover can extend proximally relative to the distal tip 164, or proximally from the second section 192b or its (direct or indirect) attachment to the core member 160, and at least partially surround or cover a distal portion of the stent 200. The distal cover 192 can be movable from the first or delivery orientation to a second or resheathing position, configuration, or orientation (see, e.g., FIGS. 7-8) in which the distal cover can be everted such that the first end 192a of the distal cover is positioned distally relative to the second end 192b of the distal cover 192 to enable the resheathing of the core assembly 140, either with the stent 200 carried thereby, or without the stent.

The distal cover 192, particularly the first end 192a thereof, can comprise one or more flexible, generally longitudinally extending strips, wings, or elongate portions that are coupled to or integrally formed with the second end 192b. The distal cover 192 can be manufactured or otherwise cut from a tube of the material selected for the distal cover or from multiple radial portions of such a tube. In such embodiments the first section 192a may be formed as multiple longitudinal strips cut from the tube, and the second section 192b may be an uncut (or similarly cut) length of the tube. Accordingly, the second section 192b and the proximally extending strips of the first section 192a may form a single, integral device or structure. In some embodiments, the distal cover 192 comprises only one, or no more than two strips, wings, or elongate portions.

In some embodiments, the distal cover 192 may comprise a tube or a longitudinally slit tube, and the first section 192a can include two or more semi-cylindrical or partially cylindrical strips or tube portions separated by a corresponding number of generally parallel, longitudinally oriented cuts or separations formed or otherwise positioned in the sidewall of the tube. Therefore, when in the pre-expansion state, as shown in FIGS. 1-5, the first section 192a may generally have the shape of a longitudinally split or longitudinally slotted tube extending or interposed radially between the outer surface of the stent or device 200 and the inner surface 118 of the catheter 110.

In various embodiments, the strips, wings, or elongate portions of the first section 192a may collectively span substantially the entire circumference of the outer surface of the stent 200 (e.g., where the cuts between the strips are splits of substantially zero width), or be sized somewhat less than the entire circumference (e.g., where the cuts between the strips are slots having a nonzero width). In accordance with some embodiments, the width of the strips, wings, or elongate portions of the first section 192a can be between about 0.5 mm and about 4 mm. The width can be about 0.5 mm to about 1.5 mm. In accordance with some embodiments, the width can be about 1 mm.

The strips, wings, or elongate portions of the first section 192a can also extend longitudinally over at least a portion of the distal portion of the stent 200. In various embodiments, the first section 192a can extend between about 1 mm and about 3 mm, or between about 1.5 mm and about 2.5 mm, or about 2 mm, over the distal portion of the stent.

The first section 192a and the second section 192b can define a total length of the distal cover 192. In some embodiments, the total length can be between about 4 mm and about 10 mm. The total length can also be between about 5.5 mm and about 8.5 mm. In some embodiments, the total length can be about 7 mm.

The strips of the first section 192a may be of substantially uniform size. For example, the first section 192a can comprise two strips spanning approximately 180 degrees each, three strips spanning approximately 120 degrees each, four strips spanning approximately 90 degrees each, or otherwise be divided to collectively cover all or part of the circumference of the stent, etc. Alternatively, the strips may differ in angular sizing and coverage area without departing from the scope of the disclosure. In one embodiment, only two strips or tube portions are employed in the first section 192a. The use of only two strips can facilitate radial expansion, distal movement and/or fold-over or everting of the first section 192a, as discussed herein, while minimizing the number of free or uncontained strips in the blood vessel lumen and any potential for injuring the vessel by virtue of contact between a strip and the vessel wall.

The distal cover 192 can be manufactured using a lubricious and/or hydrophilic material such as PTFE or Teflon®, but may be made from other suitable lubricious materials or lubricious polymers. The distal cover can also comprise a radiopaque material which can be blended into the main material (e.g., PTFE) to impart radiopacity. The distal cover 192 can have a thickness of between about 0.0005" and about 0.003". In some embodiments, the distal cover can be one or more strips of PTFE having a thickness of about 0.001".

The distal cover 192 (e.g., the second end 192b thereof) can be fixed to the core member 160 (e.g., to the distal wire 172 or distal tip 164 thereof) so as to be immovable relative to the core member 160, either in a longitudinal/sliding manner or a radial/rotational manner. Alternatively, as depicted in FIGS. 1-3 and 5-8, the distal cover 192 (e.g., the second end 192b thereof) can be coupled to (e.g., mounted on) the core member 160 so that the distal cover 192 can rotate about the longitudinal axis A-A of the core member 160 (e.g., of the distal wire 172), and/or move or slide longitudinally along the core member. In such embodiments, the second end 192b can have an inner lumen that receives the core member 160 therein such that the distal cover 192 can slide and/or rotate relative to the core member 160. Additionally in such embodiments, the distal device interface 190 can further comprise a proximal restraint 194 that is fixed to the core member 160 and located proximal of the (second end 192b of the) distal cover 192, and/or a distal restraint 196 that is fixed to the core member 160 and located distal of the (second end 192b of the) distal cover 192. The proximal and distal restraints 194, 196 can be spaced apart along the core member 160 by a longitudinal distance that is greater than the length of the second end 192b, so as to leave one or more longitudinal gaps 197 between the second end 192b and one or both of the proximal and distal restraints 194, 196, depending on the position of the second end 192b between the restraints. When present, the longitudinal gap(s) 197 allow the second end 192b and/or distal cover 192 to slide longitudinally along the core member 160 between the restraints 194, 196. The longitudinal range of motion of the second end 192b and/or distal cover 192 between the restraints 194, 196 is approximately equal to the total length of the longitudinal gap(s) 197.

Instead of or in addition to the longitudinal gap(s) 197, the distal device interface 190 can comprise a radial gap 198 between the outer surface of the core member 160 (e.g., of the distal wire 172) and the inner surface of the second end 192b. Such a radial gap 198 can be formed when the second end 192b is constructed with an inner luminal diameter that is somewhat larger than the outer diameter of the corresponding portion of the core member 160. When present, the radial gap 198 allows the distal cover 192 and/or second end 192b to rotate about the longitudinal axis A-A of the core member 160 between the restraints 194, 196. The presence of longitudinal gaps 197 of at least a minimal size on either side of the second end 192b can also facilitate the rotatability of the distal cover.

One or both of the proximal and distal restraints 194, 196 can have an outside diameter or other radially outermost dimension that is smaller than the (e.g., pre-deployment) outside diameter or other radially outermost dimension of the distal cover 192, so that one or both of the restraints 194, 196 will tend not to bear against or contact the inner surface 118 of the catheter 110 during operation of the core assembly 140.

In the embodiment depicted in FIGS. 1-3 and 5-8, the second end 192b of the distal cover 192 includes an internal hoop 192c which can comprise a (metallic or polymeric) coil as depicted, or other generally rigid, tubular or cylindrical internal member such as a short segment of relatively stiff polymeric or metallic tubing. The internal hoop 192c can be contained in an annular enclosure or loop(s) formed by the second end 192b, or otherwise attached to or integrated into the second end 192b in a manner that tends to maintain an inside diameter of the distal cover 192 in the second end 192b that is larger than the outside diameter of the adjacent portion of the core member 160 (or the wire 172 thereof). In other words, the hoop 192c can help maintain the presence of the radial gap 198 between the inside diameter of the second end 192b and the outside diameter of the core member 160 or distal wire 172.

The annular enclosure or loop(s) of the second end 192b can be formed by wrapping a portion of a sheet or tube of the distal cover material (e.g., PTFE) around the sidewall and through the lumen of the hoop 192c and adhering, gluing or heat bonding an end of the wrapped portion of the sheet or tube to the adjacent, proximally extending portion of the sheet or tube. Thus are formed two layers that are adhered together on the proximal side of the hoop 192. Where the distal cover material comprises PTFE, unsintered PTFE can be used to enable bonding the two portions of the material together with heat and pressure, which is not typically possible with "ordinary" or sintered PTFE.

In operation, the distal cover 192, and in particular the first section 192a, can generally cover and protect the distal end 204 of the stent 200 as the stent 200 is moved distally within the catheter 110. The distal cover 192 may serve as a bearing or buffer layer that, for example, inhibits filament ends of the distal end 204 of the stent 200 (where the stent 200 comprises a braided stent) from contacting the inner surface 118 of the catheter 110, which could damage the stent 200 and/or catheter 110, or otherwise compromise the structural integrity of the stent 200. Since the distal cover 192 may be made of a lubricious material, the distal cover 192 may exhibit a low coefficient of friction that allows the distal end 204 of the stent 200 to slide axially within the catheter 110 with relative ease. The coefficient of friction between the distal cover and the inner surface of the catheter can be between about 0.02 and about 0.4. For example, in embodiments in which the distal cover and the catheter are formed from PTFE, the coefficient of friction can be about 0.04. Such embodiments can advantageously improve the ability of the core assembly to pass through the catheter, especially in tortuous vasculature.

Further, as shown in FIGS. 1-5, at least a portion of the distal cover 192 can at least partially extend or be interposed radially between the distal portion of the stent 200 and the inner surface 118 of the catheter 110 in the first position, configuration, or orientation. In the first orientation, the first section 192a of the distal cover 192 can extend from the second section 192b in a proximal direction to a point where the first section is interposed between the distal portion of the stent 200 and the inner surface 118 of the catheter 110. In this orientation, the first section of the distal cover can take on a "proximally oriented" position or configuration.

Figure 4:
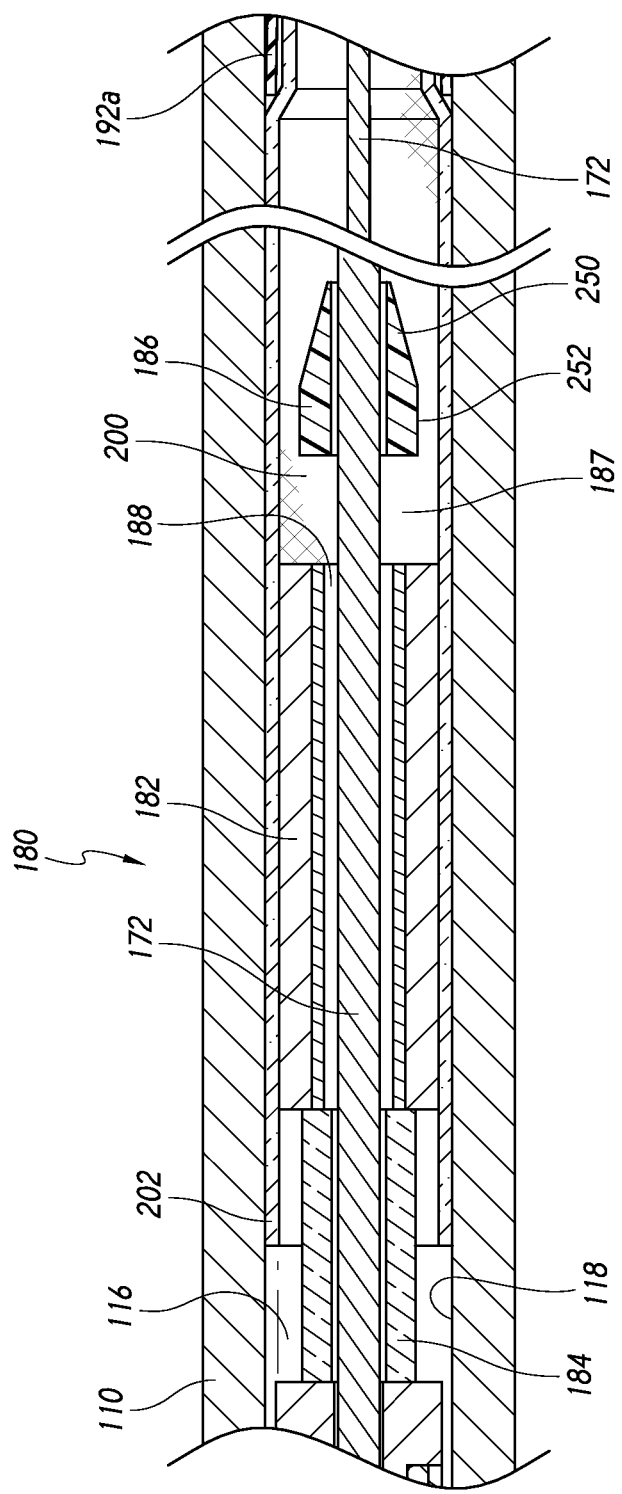
FIG. 4 is another enlarged side, cross-sectional view of the delivery system shown in FIG. 1.
Figure 5:
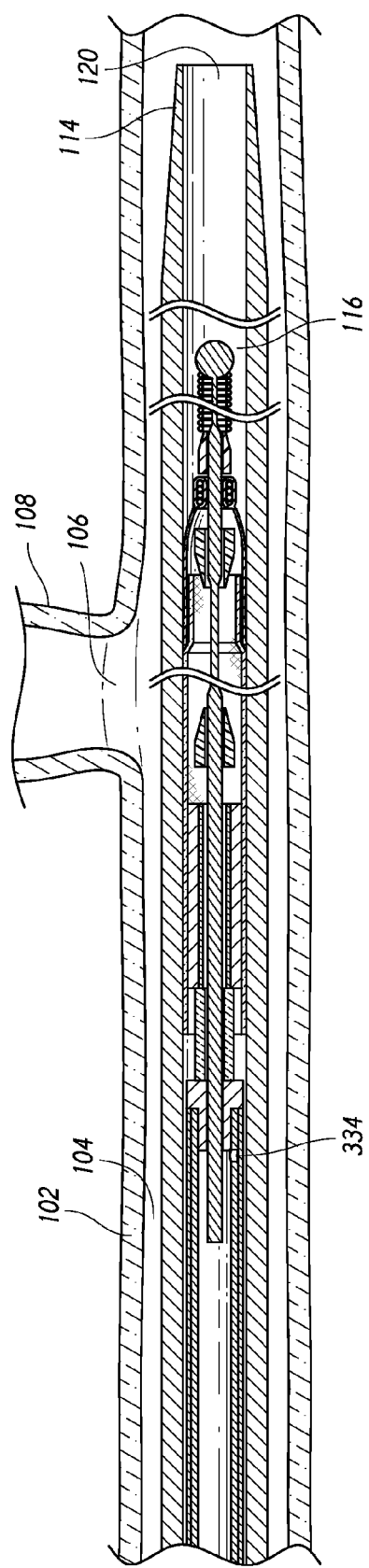
FIG. 5 is a side, cross-sectional view of a medical device delivery system in a first position, adjacent to a target location, according to some embodiments.
Figure 6:
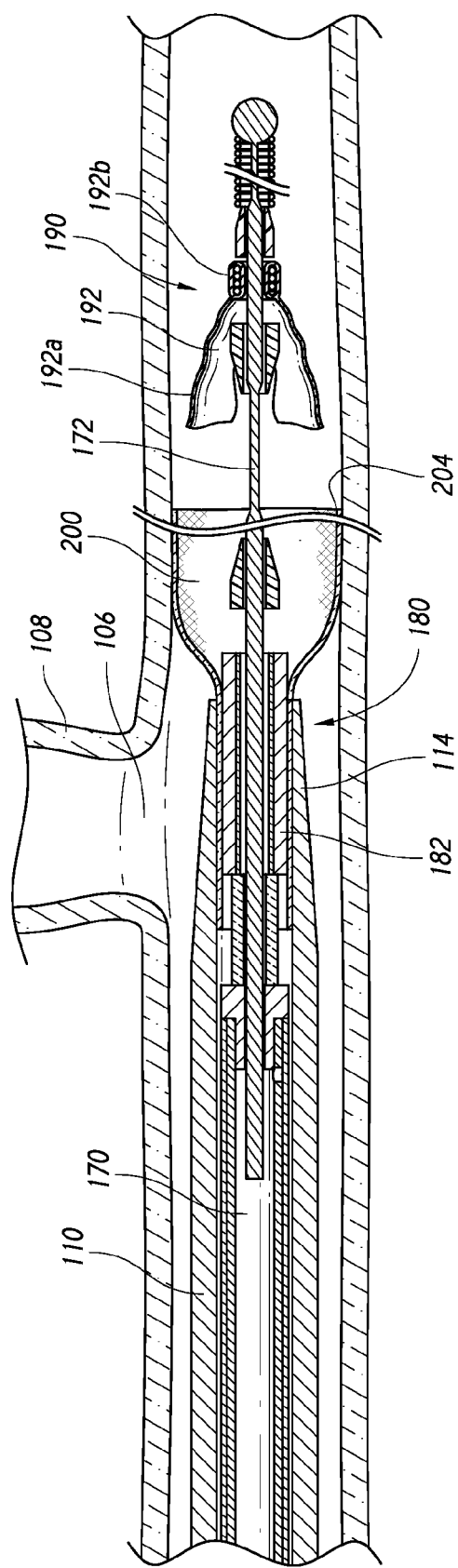
FIG. 6 is a side, cross-sectional view of the delivery system shown in FIG. 5, wherein the system is in a second position in which a stent thereof is partially expanded and a distal cover is disengaged from the stent, according to some embodiments.

The core assembly 140 shown in FIGS. 1-4 can operate as illustrated in FIGS. 5-9. The core assembly 140 can be distally advanced until the distal portion of the stent 200 is positioned distally beyond the distal end 114 of the catheter 110 to permit expansion of the distal portion of the stent 200 into a lumen 104 of the blood vessel 102. As the distal portion of the stent 200 expands, it can cause the distal cover 192 to be opened or moved from the first orientation. Because (when braided) the stent 200 can often foreshorten as it expands, the stent 200 can withdraw from engagement with the distal cover 192, as shown in FIG. 6.

Figure 7:
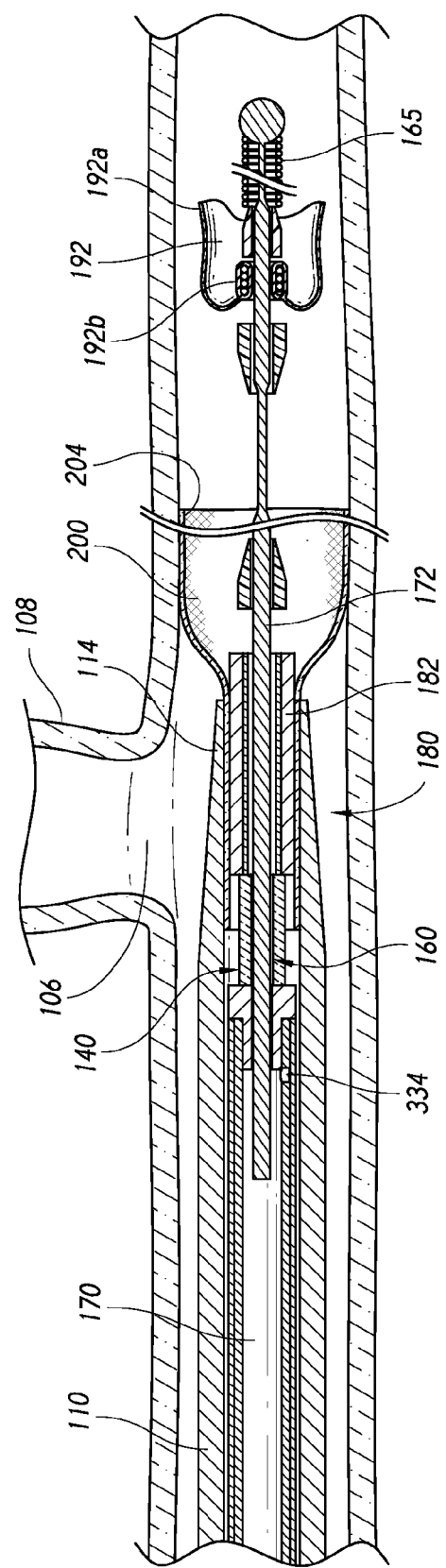
FIG. 7 is a side, cross-sectional view of the delivery system shown in FIG. 5, wherein the distal cover is moved to an everted position, according to some embodiments.
Figure 8:
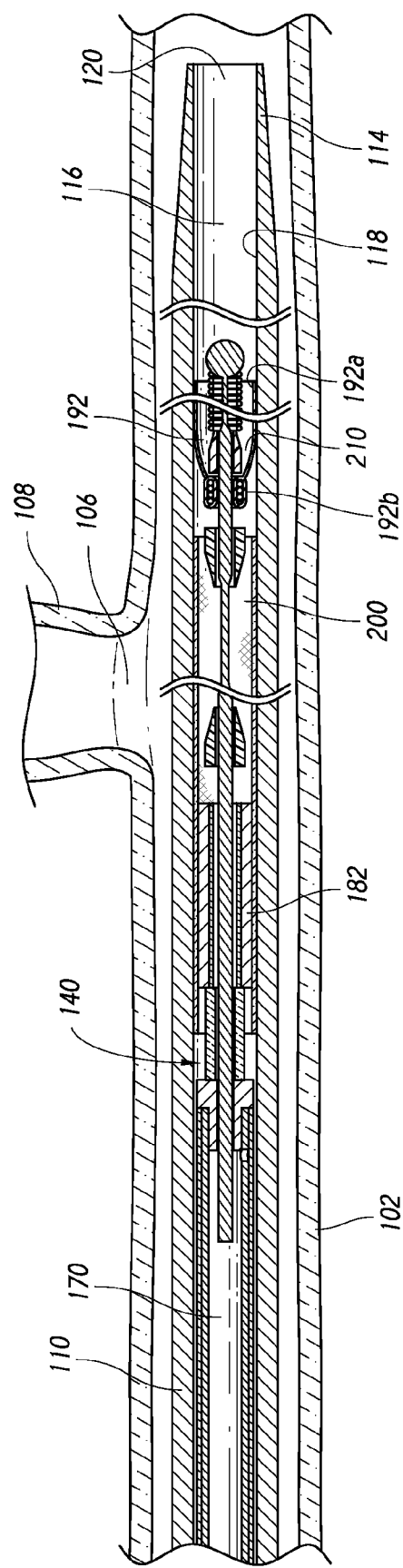
FIG. 8 is a side, cross-sectional view of the delivery system shown in FIG. 5, wherein the stent has been retracted into a catheter of the system, according to some embodiments.

After the distal cover 192 has become disengaged from the stent 200 to reach the state shown in FIG. 6, the cover can proceed to the second orientation as shown in FIG. 7, as oncoming blood flow and/or other forces urge the first section 192a distally relative to the core member 160. Alternatively, the distal cover 192 can remain substantially in the disengaged, proximally-extending configuration shown in FIG. 6 until the core assembly 140 is withdrawn proximally into the catheter 110, at which point the distal end 114 of the catheter 110 can force the approaching first section 192a of the cover 192 to evert or otherwise take on the second configuration as shown in FIGS. 7-8. In each case, the distal cover 192 can move toward an everted position or configuration in which the first section 192a of the distal cover 192 is flipped, everted or rotated to extend in a distal direction or in a "distally oriented" position or configuration. In some embodiments of a distally-oriented second configuration, all or at least a portion of the first section 192a is located distal of all or at least a portion of the second section 192b.

Figure 9:
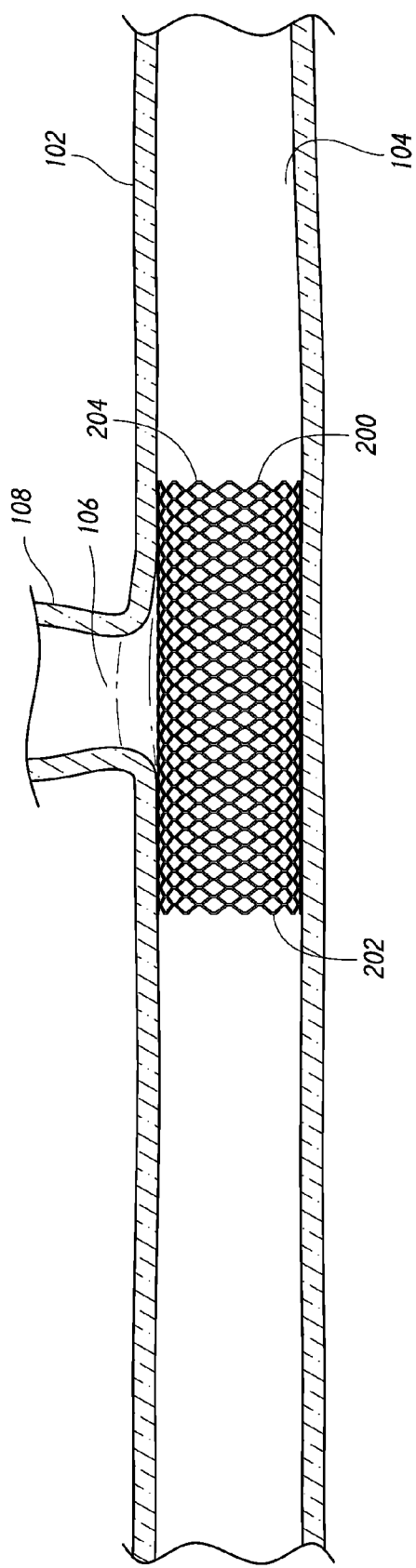
FIG. 9 is a side, cross-sectional view of the stent expanded at the target location, according to some embodiments.

The stent 200 can be further unsheathed and subsequently released into position in the lumen 104 of the vessel 102, e.g., across and/or spanning a neck 106 of an aneurysm 108 formed in the wall of the vessel 102 (as shown in FIG. 9), or the stent 200 can be retracted and withdrawn back into the catheter 110 (as shown in FIG. 8), if needed. In either situation, when the distal portion of the core assembly 140 is withdrawn into the lumen 116 of the catheter 110, the distal cover 192 can be retracted into the catheter 110 in the second position, configuration, or orientation, in which the distal cover 192 can be at least partially everted, as shown in FIGS. 7 and 8. This can facilitate complete resheathing of the stent 200 and/or the core assembly 140 within the catheter 110.

Figure 3:
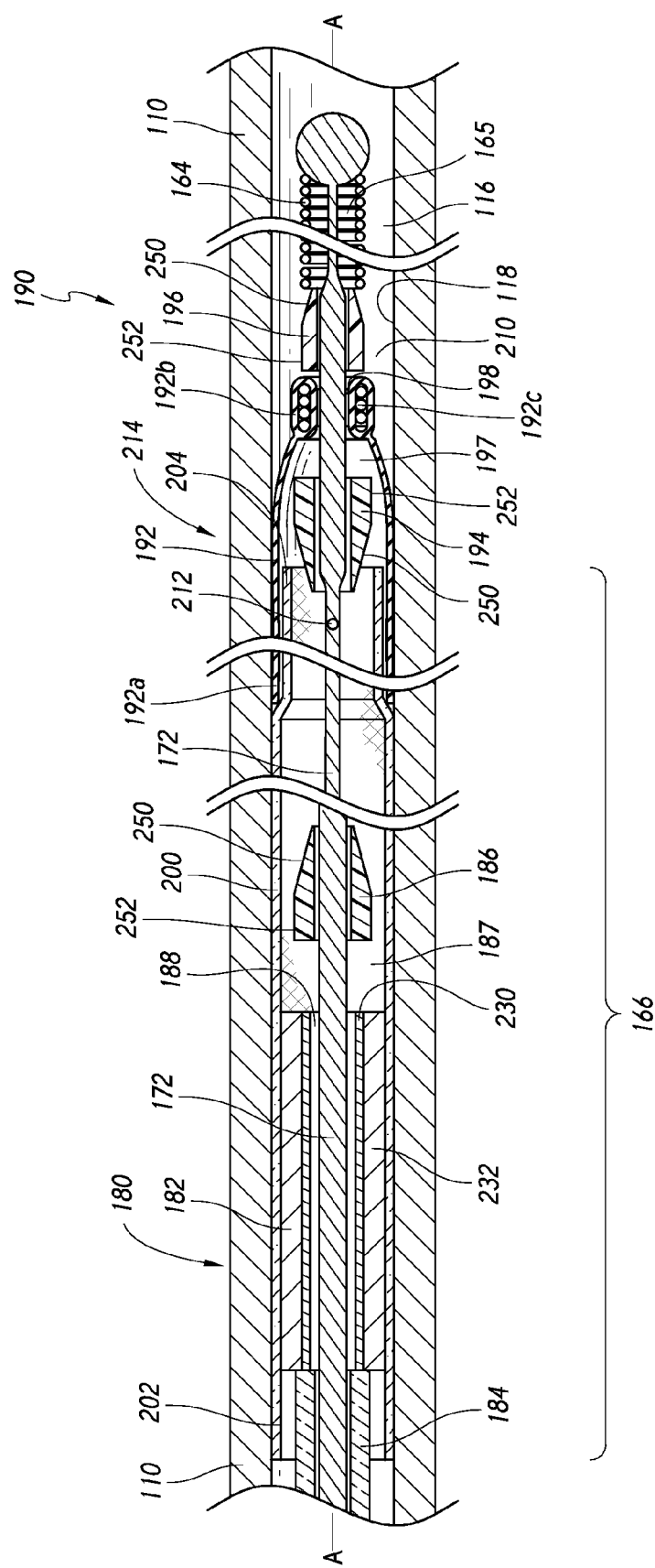
FIG. 3 is an enlarged side, cross-sectional view of the delivery system shown in FIG. 1.

In some embodiments, in the first orientation, the first section 192a of the distal cover 192 is positioned outside of a radial space 210 located between the core assembly 160 or axis A-A (in either case distal of the second section 192b or the location where the distal cover 192 is connected to the core member) and the inner wall of the catheter 110, as shown in FIG. 3. The distal cover 192 can extend proximally from the second section 192b and/or connection location, and away from the radial space 210. Additionally, in some such embodiments, in the second orientation, some or all of the first section 192a of the distal cover 192 can extend distally through the radial space 210 upon retraction of the core assembly 140 into the catheter 110, as shown in FIG. 8.

Further, in some embodiments, the first section 192a of the distal cover 192 can radially overlap with the distal end 204 of the stent 200 at an overlap point 212 along the core member 160. As illustrated in FIG. 3, the overlap point 212 can be located along the core member 160 at or near a distal end 214 of the intermediate portion 166 of the core member 160, or at any location along the core member 160 that underlies an overlap of the (first section 192a of the) distal cover 192 over the stent 200 when the core assembly 140 is in its pre-deployment configuration shown in FIGS. 1-3 and 5. Additionally, in some such embodiments, in the second orientation, the first section 192a of the distal cover 192 no longer overlaps with the (distal end 204 of) the stent 200 at the overlap point 212 (and the first section 192a can be located distally of such location), upon retraction of the core assembly 140 into the catheter 110, as shown in FIG. 8.

In the second orientation, as shown in FIGS. 7-8, there is no longer radial overlap of the stent 200 and the cover 192 at the overlap point 212 or at the distal end 214 of the intermediate section 166. Thus, after disengagement of the distal cover 192 from the stent 200, the core assembly 140 can be proximally withdrawn into the catheter 110 and the distal cover 192 can generally extend in a distal direction away from the overlap point 212. As also shown in FIG. 8, at such time that the stent 200 is resheathed or withdrawn into the catheter 110 after partial expansion or deployment, the stent 200 and the distal cover 192 will not overlap at the overlap point 212. Thus, the distal cover 192 will not overlap the stent 200 or the overlap point 212 after at least partial expansion of the stent 200 when the core assembly 140 is withdrawn into the catheter 110. Further, once the distal cover 192 is disengaged, the intermediate portion 166 of the core member 160 can be positioned radially adjacent to the distal end 114 of the catheter 110 with the distal cover 192 being positioned outside of the radial space between the intermediate portion 166 and the (inner wall 118 of the) catheter 110. Accordingly, the movement and configuration of the distal cover 192 can enable the core assembly 140 to provide radial clearance between the core member 160 or the intermediate portion 166 and the catheter 110 for facilitating resheathing of the core member 160 and stent 200, as shown in FIGS. 7-8.

Structures other than the herein-described embodiments of the distal cover 192 may be used in the core assembly 140 and/or distal device interface 190 to cover or otherwise interface with the distal end 204 of the stent 200. For example, a protective coil or other sleeve having a longitudinally oriented, proximally open lumen may be employed. Suitable such protective coils include those disclosed in U.S. Patent Application Publication No. 2009/0318947 A1, published on Dec. 24, 2009, titled SYSTEM AND METHOD FOR DELIVERING AND DEPLOYING AN OCCLUDING DEVICE WITHIN A VESSEL.

In embodiments of the core assembly 140 that employ both a rotatable proximal engagement member 182 and a rotatable distal cover 192, the stent 200 can be rotatable with respect to the core member 160 about the longitudinal axis A-A thereof, by virtue of the rotatable (connections of the) proximal engagement member 182 and distal cover 192. In such embodiments, the stent 200, proximal engagement member 182 and distal cover 192 can rotate together in this manner about the core member. When the stent 200 can rotate about the core member 160, the core assembly 140 can be advanced more easily through tortuous vessels as the tendency of the vessels to twist the stent and/or core assembly is negated by the rotation of the stent, proximal engagement member and distal cover about the core member. In addition, the required push force or delivery force is reduced, as the user's input push force is not diverted into torsion of the stent and/or core member. The tendency of a twisted stent and/or core member to untwist suddenly or "whip" upon exiting tortuosity or deployment of the stent, and the tendency of a twisted stent to resist expansion upon deployment, are also reduced or eliminated. Further, in some such embodiments of the core assembly 140, the user can "steer" the core assembly 140 via the tip coil 165, particularly if the coil 165 is bent at an angle in its unstressed configuration. Such a coil tip can be rotated about the axis A-A relative to the stent 200, engagement member 182 and/or distal cover 192 by rotating the distal end 162 of the core member 160. Thus the user can point the coil tip in the desired direction of travel of the core assembly, and upon advancement of the core assembly the tip will guide the core assembly in the chosen direction.

As noted, embodiments of the distal cover can provide various advantages. For example, the use of the distal cover can allow the core assembly to be easily urged toward the treatment site within the catheter. This can advantageously reduce the delivery force required to move the core assembly through the catheter. Further, a flexible distal cover such as the depicted distal cover 192 can also allow the distal portion of the stent to open or expand radially immediately as the distal portion of the stent exits the catheter. The distal cover can be easily urged away from the first or encapsulating position or configuration such that the expansion of the stent is not hindered and expansion can be predictable to the clinician. Where employed, this can be a significant improvement over prior art devices that used a relatively rigid tube, such as a coil to distally restrain a distal end of the stent, which could impede or make unpredictable the proper expansion or deployment of the distal end of the stent.

Further, where the first portion 192a is flexible, evertible, and/or provides a minimal cross-section, the intermediate portion of the core assembly can be easily recaptured within the catheter (with or without the stent coupled thereto (e.g., mounted thereon)) to facilitate resheathing. Thus, the catheter can remain in place in the vasculature and the entire core assembly can be withdrawn therefrom. This can enable the clinician to "telescope" one or more other stents (e.g., delivering more than one stent such that it overlaps with another stent) without having to remove the catheter, saving time and reducing trauma to the patient. This also enables the clinician to remove the core assembly and stent entirely from the catheter in the event of a failure to deploy or other evident defect in the stent, and insert another core assembly and stent through the same catheter, with the same time savings and reduction in trauma.

In other embodiments, the distal device interface 190 can omit the distal cover 192, or the distal cover can be replaced with a component similar to the proximal engagement member 182. Where the distal cover 192 is employed, it can be connected to the distal tip coil 165, e.g., by being wrapped around and enclosing some or all of the winds of the coil 165, or being adhered to or coupled to the outer surface of the coil by an adhesive or a surrounding shrink tube. In still other embodiments, the distal device interface 190 (or the proximal device interface 180) can be omitted altogether.

Additional details regarding the proximal engagement member will now be discussed, with reference especially to FIGS. 3, 10 and 11. Some embodiments of the proximal engagement member 182 can be of multi-layer construction, which can be useful for facilitating rotation of the engagement member 182 and/or stent 200 about the core member 160. For example, the proximal engagement member 182 can comprise a generally tubular or cylindrical inner layer 230, and another generally tubular or cylindrical outer layer 232 that overlies the inner layer 230. The outer layer 232 can be adhered to or otherwise securely joined to the inner layer 230 so that the two cannot rotate or move longitudinally relative to each other during the ordinary use of the core assembly 140 and delivery system 100.

The inner layer 230 and outer layer 232 can differ in mechanical properties such as hardness. For example, the outer layer 232 can comprise a relatively soft material to facilitate relatively high-friction or "high-grip" contact with the inner surface of the stent 200. The inner layer can be formed from a relatively hard or stiff material to facilitate low-friction engagement with the adjacent portion of the core member 160, and high hoop strength to resist inward deflection or collapse of the inner lumen 234 of the proximal engagement member 182. Such inward deflection or collapse can result in "pinching" the core member 160 with the inner layer 230 and consequent degradation of the ability of the proximal engagement member 182 to rotate and/or move longitudinally with respect to the core member 160. When contact does occur between the inner surface of the inner layer 230 and the outer surface of the core member 160, the relatively hard/stiff material of the inner layer 230 minimizes the friction resulting from such contact.

In some embodiments of the multi-layer proximal engagement member, the outer layer 232 can be formed from a relatively soft polymer or elastomer such as silicone, rubber (e.g., Chronoprene™), thermoplastic polyurethane (e.g., Tecoflex™) or polyether block amide (e.g., Pebax™). Whether made of such materials, or of other materials, the outer layer 232 can have a durometer of between 10 A and 50 A, or between 15 A and 40 A, or about 20 A, or about 25 A.

Instead of or in addition to the above-recited materials and/or properties of the outer layer 232, in some embodiments, the inner layer 230 can be formed from polyimide, e.g., a polyimide tube; alternatively a tubular metallic coil (e.g., a stainless steel coil) could be employed, or a metal tube, either with or without slots or a spiral cut formed in the sidewall. Whether made of such materials, or of other materials, the inner layer 230 can have a higher durometer than the outer layer 232, e.g., above 70 D or between 70 D and 100 D.

In some embodiments, the inner and outer layers 230, 232 can be integrally formed. For example, both layers could be formed from a single cylinder of soft material wherein the harder/stiffer inner layer comprises the radially inner portions of the cylinder which have been treated or processed to become harder/stiffer. Or the reverse could be done, wherein a cylinder of hard material is processed to make its outer layer softer and/or higher-friction.

Although, as disclosed above, the outer layer 232 can be made from a variety of materials, silicone is particularly preferred because it offers a high coefficient of friction, high heat resistance to facilitate sterilization, and high creep resistance to resist being "imprinted" with, or interlocked with, the filament or strut pattern of the adjacent medical device or stent 200. The high coefficient of friction of silicone also facilitates the use of a relatively short proximal engagement member, e.g., (for delivery of a neurovascular stent) less than 5 mm, less than 3 mm, between 1 mm and 3 mm, or between 2 mm and 2.5 mm. It is also preferred to use a silicone outer layer 232 in combination with a thermoset material (such as polyimide) for the inner layer 230, of a higher durometer than the outer layer 232, or generally to use thermoset materials for both the inner and outer layers 230, 232, with the outer layer of lower durometer than the inner layer.

Despite these advantages of silicone, it is difficult to process in a manner useful to form a multi-layer tubular component like the proximal engagement member 182, e.g., via co-extrusion. Because of this difficulty, it was necessary for the inventors to develop a method of manufacturing the proximal engagement member 182 with a silicone outer layer 232 and an inner layer of higher-durometer thermoset material such as polyimide.

In one embodiment, the proximal engagement member 182 can be manufactured as follows. A length of polyimide tubing of approximately 100 mm in length can be placed over a metallic mandrel so that the mandrel passes through the lumen of the tubing. The mandrel is sized to fit closely within the tubing lumen so as to hold the tubing in place on the mandrel via frictional engagement with the inner wall of the tubing. In addition, the close fit of the mandrel helps to seal the tubing lumen from inflow of silicone material during the subsequent dip coating of the tubing. Once the tubing is on the mandrel, the mandrel is mounted on a dipping fixture.

A silicone reservoir is provided in the form of a vertical, open-topped cylinder, and the cylinder is prepared by wiping the inner surfaces of it with 70% isopropyl alcohol and allowing it to dry for 5 minutes. The mounted polyimide tubing is prepared in a similar manner by wiping it twice with a lint-free cloth wetted with 70% isopropyl alcohol and allowing it to dry for 5 minutes. Once the tubing is dry, it is "painted" with a primer (e.g., MED-163 Primer from NuSil Technology of Carpinteria, Calif. USA) by first wetting the bristles of an applicator brush with a pipette full of the primer, and then painting the tubing (held along with the mandrel in a vertical orientation from the dipping fixture) with the wet brush with a bottom-to-top motion in a first pass, and then in a second pass after rotating the tubing and mandrel 90 degrees about the vertical axis of the tubing and mandrel. Once the primer has been applied to the tubing in this manner, the tubing is allowed to dry while exposed in a humidity chamber at 50%-70% relative humidity and 23°-28° C. temperature for 30-45 minutes.

Flowable silicone material is prepared using, for example, a 2-part medical silicone such as MED-4011 (Parts A and B) from NuSil Technology of Carpinteria, Calif. USA. The silicone elastomer (Part A) and liquid crosslinker (Part B) are combined in a mix of 10 parts elastomer with 1 part crosslinker, and mixed in a sealed container in a centrifugal mixer at 3000 rpm for 60 seconds. After mixing, the silicone is allowed to sit for ten minutes before the container is unsealed.

The flowable silicone is then poured into the reservoir cylinder, and the reservoir is positioned in a programmable dipping apparatus beneath a vertically moveable dipping actuator. The dipping fixture, mandrel and tubing are mounted on the dipping actuator with the mandrel and tubing in a vertical, downward-extending orientation, and the vertical axis of the mandrel and tubing aligned with the central vertical axis of the reservoir cylinder. The dipping apparatus is then operated to lower the dipping actuator, mandrel and tubing to a position in which the lower end of the tubing is just above the surface of the silicone. The tubing and mandrel are then lowered or dipped into the silicone substantially along a straight line at a velocity of 2.29 mm per minute, over a stroke distance of 110 mm. At the bottom of the stroke, the dipping actuator, tubing and mandrel are raised out of the silicone at a velocity of 400 mm/minute.

The fixture, mandrel and coated tubing are then removed from the dipping apparatus and placed in an oven at 100° C. temperature for 15 minutes. In the oven, the tubing and mandrel are oriented vertically but inverted relative to their orientation employed during the dipping process. After removal from the oven, the coated tubing is allowed to cool for 5 minutes. After cooling, the tubing is sliced into individual proximal engagement members 182 with a series of cuts made along the tubing orthogonal to the longitudinal axis of the tubing.

In some embodiments, the proximal engagement member can have an axial length of 2.25 mm, overall outside diameter of 0.02275-0.02500", inside diameter of 0.010", inner layer 230 thickness (e.g., polyimide tubing wall thickness) of 0.0015", outer layer 232 thickness greater than 0.003", and inner layer 230 outside diameter of 0.0135" or less.

The use of a "high-grip" material such as silicone for the outer layer 232 makes practical the use of a proximal engagement member 182 that is relatively short in axial length (i.e., the dimension measured along or parallel to the longitudinal axis A-A). The proximal engagement member can be less than 5.0 mm in axial length, or less than 3.0 mm in axial length, or between 1.3 mm and 5.0 mm in axial length, or between 1.3 mm and 3.0 mm in axial length. Generally, a shorter proximal engagement member 182 is advantageous because shortness tends to reduce the tendency of the engagement member 182 to stiffen the core assembly 140 and delivery system 100. Accordingly there is made possible in some embodiments an engagement member 182 that not only can rotate about the core member 160 but can also effectively grip the inner surface of the stent 200 even at lengths below 5 mm, or below 3 mm.

Figure 10:
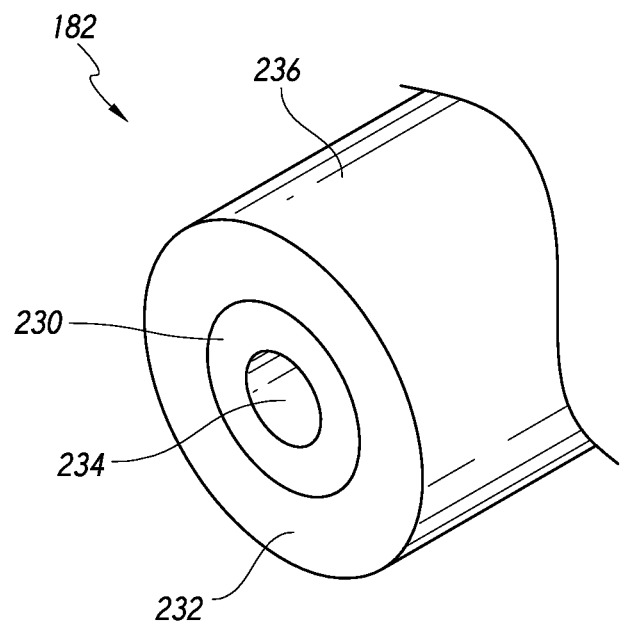
FIGS. 10 and 11 are partial perspective views of an engagement member, according to some embodiments.
Figure 11:
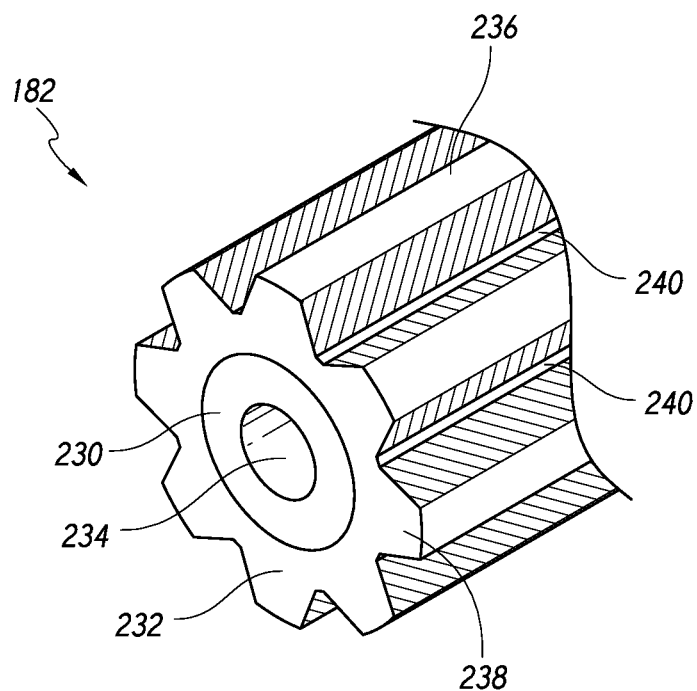

As may be observed from FIGS. 10 and 11, the outer surface 236 of the outer layer 232 can comprise a generally smooth surface as shown in FIG. 10, or a non-smooth surface such as that shown in FIG. 11, comprising, for example, a number of outwardly projecting and longitudinally extending ridges 238 that alternate with longitudinally extending recesses 240. Other patterns of projecting members and recesses, such as combinations of spikes and recessed portions, can also be employed.

Figure 12:
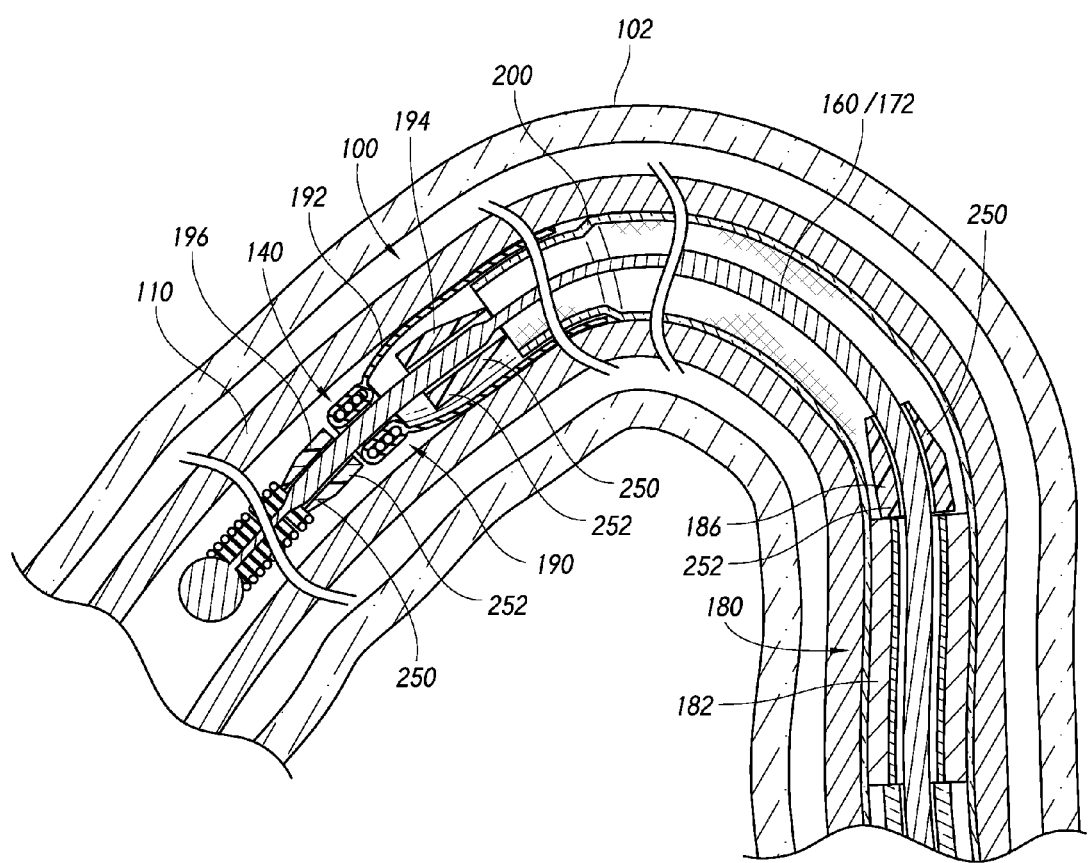
FIG. 12 is a side, cross-sectional view of a medical device delivery system being advanced through a torturous pathway, according to some embodiments.

With reference now to FIGS. 3, 4 and 12, it may be observed that the distal restraint 186 of the proximal device interface 180, and/or the proximal and/or distal restraints 194, 196 of the distal device interface 190, can each optionally comprise a tapered portion 250 and a cylindrical or non-tapered portion 252. In the proximal device interface 180, the distal restraint 186 can form a tapered portion 250 that is located distal of its non-tapered portion 252, and tapers down in diameter or cross-sectional size as it extends distally, away from the proximal engagement member 182. In the distal device interface 190, the proximal restraint 194 can form a tapered portion 250 that is located proximal of its non-tapered portion 252, and tapers down in diameter or cross-sectional size as it extends proximally, away from the distal engagement member 192; the distal restraint 196 can form a tapered portion 250 that is located distal of its non-tapered portion 252, and tapers down in diameter or cross-sectional size as it extends distally, away from the distal engagement member 192. Accordingly, in the depicted embodiment each of the restraints 186, 194, 196 forms a tapered portion 250 that tapers radially inwardly as it extends away from its respective engagement member 182/192 and/or its respective longitudinal gap(s) 187/197.

By incorporating the tapered portion(s) 250, the restraint(s) 186, 194, 196 can provide the benefit of relatively large diameter or cross-sectional size in the non-tapered portion 252 (effective longitudinal restraint of the engagement member 182/192) and/or relatively long axial length (secure attachment to the core member 160) without suffering the drawback of increased stiffness or reduced bendability of the core assembly 140 and delivery system 100. This may be understood best with reference to FIG. 12, which shows the delivery system 100 including the core assembly 140 passing through a bend in the vessel 102. In this drawing it can be observed that the tapered portion 250 of the distal restraint 186 of the proximal device interface 180 provides ample clearance for the sharply bending adjacent portion of the catheter 110 and stent 200, as compared to a non-tapered restraint of similar length and cross-sectional size or diameter. Accordingly the tapered restraint 186 allows the core assembly 140 and core member 160 to bend more sharply (and/or to bend without the restraint contacting the inner surface of the stent 200) in the vessel 102 than would be possible with a non-tapered restraint of similar axial length and cross-sectional size or diameter. In this manner the risk of a distal corner of the restraint 186 impinging on the inner surface of the stent 200 and creating a pressure concentration that can require a higher push force from the user, is reduced.

With further reference to FIG. 3, in some embodiments the distal restraint 196 of the distal device interface 190 may have a smaller (maximum) outside diameter or cross-sectional size than the proximal restraint 194 of the distal interface 190. Such a smaller distal restraint can help provide radial clearance for the everted first end 192a of the distal cover 192 during retraction into the catheter 110.

Figure 13:
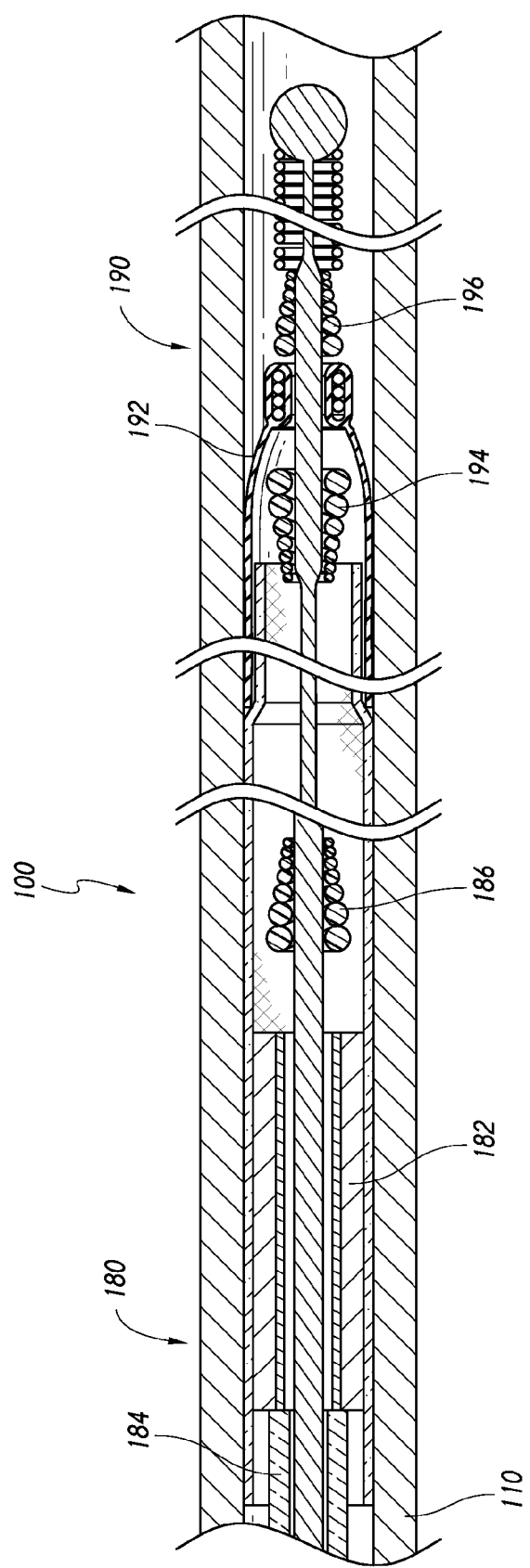
FIG. 13 is another side, cross-sectional view of a core assembly, according to some embodiments.

As seen in FIG. 13, in other embodiments, one, some or all of the restraints 184, 186, 194, 196 can comprise a tapered coil. Such coil(s) can be formed from wire stock with a tapering diameter; when wound into a coil the resulting coil tapers to a smaller diameter in the smaller diameter region of the wire. Restraints in the form of coils can provide a high degree of flexibility and improve the bendability of the core assembly 140 and delivery system 100.

One, some or all of the restraints 184, 186, 194, 196 can be formed from a radiopaque material (e.g., platinum, iridium, alloys thereof, etc.), so as to facilitate visibility of the respective portions of the core assembly 140 in a patient via fluoroscopy or other imaging. In one configuration, at least the distal restraint 186 of the proximal device interface 180 is radiopaque, and the catheter 110 is radiopaque at or near its distal tip, so as to indicate to the user that the proximal engagement member 182 is soon to exit the distal end of the catheter 110, and the delivery system 100 or core assembly 140 as a result will lose the capability to withdraw the stent 200 back into the catheter 110. Accordingly the user can observe via fluoroscopy that the distal restraint 186 is approaching the distal end 114 of the catheter 110 and thereby recognize that the delivery system 100 or core assembly 140 will soon lose the capability to withdraw the stent 200 back into the catheter 110.

As mentioned previously, the core member 160 can optionally be of multi-member construction, and can include the tube 170 which can comprise a hypotube. The tube 170 can have a sidewall that is "uncut" or without openings or voids formed therein. Alternatively, the tube 170 can have openings, voids or cuts formed in the sidewall to enhance the flexibility of the tube. This may be done by cutting a series of slots in the sidewall along part or all of the length of the tube, or cutting or drilling a pattern of other openings in the sidewall, or cutting a spiral-shaped void in the sidewall.

In some embodiments, for example where the delivery system is to be used in narrow and/or tortuous vasculature, such as the neurovasculature, the tube 170 can be of relatively small outside diameter (e.g., 0.040" or less, or 0.030" or less, or 0.027" or less, or about 0.020"); have a relatively thin sidewall thickness (e.g., 0.0050" or less, or 0.0040" or less, or about 0.0030", or between 0.0025" and 0.0035"); and/or be of relatively long overall length (e.g., 50 cm or more, or 60 cm or more, or 70 cm or more, or 80 cm or more, or about 91 cm). Instead of or in addition to any one or combination of such dimensions, the tube can have a relatively long cut length (the length of the portion of the tube in which opening(s), void(s), cut(s), spiral(s) is/are present) of 50 cm or more, or 60 cm or more, or 70 cm or more, or 80 cm or more, or about 86 cm.

A relatively long, small-diameter and/or thin-walled spiral-cut tube offers certain advantages for use in the core member 160 in narrow and/or tortuous vasculature, such as the neurovasculature. The tube can be made highly flexible (or inflexible as the case may be) where necessary by use of an appropriate spiral pitch, and the column strength or "pushability" of the tube can be maintained largely independent of its flexibility, as the diameter of the tube can remain constant along its length, in contrast with a long tapering wire which must sacrifice pushability for flexibility as it narrows. The combination of high flexibility and pushability can facilitate easier navigation into difficult, tortuous vascular locations.

Figure 14:
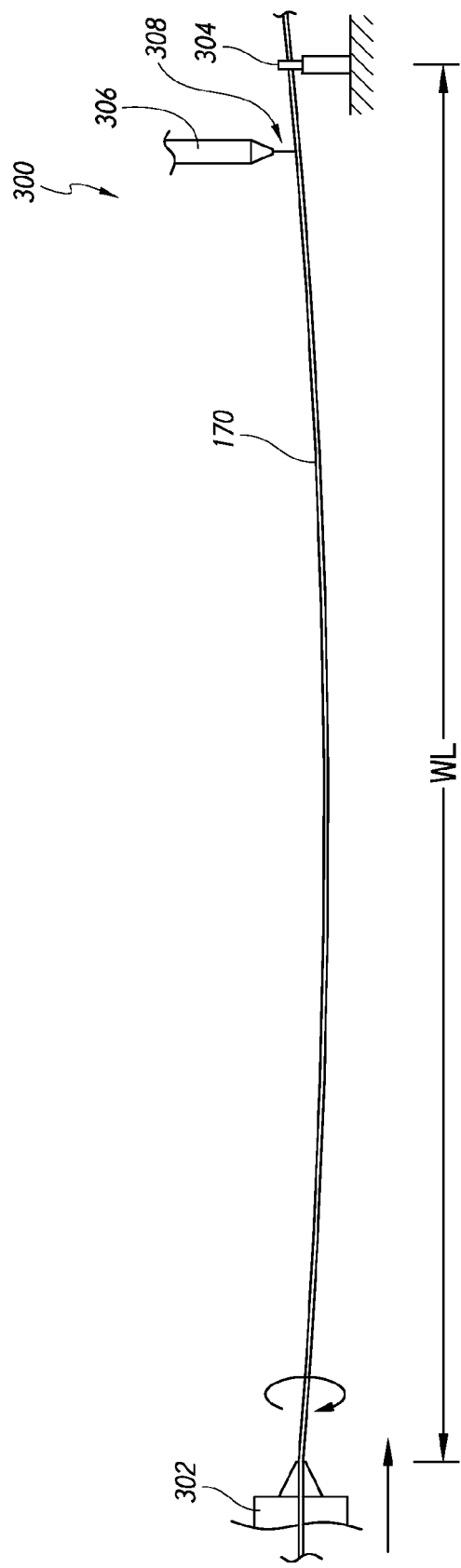
FIG. 14 is a schematic view of a laser cutting machine performing a laser cut in a catheter.

Despite these advantages, difficulties can arise when attempting to make a relatively long, small-diameter and/or thin-walled spiral-cut tube. FIG. 14 illustrates some of these difficulties in the context of a laser cutting machine 300, in which the tube 170 is supported at one end in a moveable and rotatable chuck 302 and at the other end in a stationary bushing 304. A laser 306, also stationary, is positioned between the chuck 302 and the bushing 304 and oriented to emit a cutting laser beam 308 at the sidewall of the tube 170 as the tube passes by the laser 308. The chuck 302 is programmable to rotate the tube 170 and move it laterally relative to the laser beam 308 at selected rates of rotation and lateral movement, to form a spiral cut in the sidewall of the tube at a desired pitch and location. The process begins with the chuck 302 positioned at the maximum distance away from the laser 306 and bushing 304 (with a maximum working length WL of tube 170 extending therebetween), and the chuck 302 and tube 170 coupled thereto move laterally toward the laser 306 and bushing 304 while rotating until the chuck 302 reaches a minimum distance from the laser and bushing (with a minimum working length WL of tube 170 extending therebetween). However, when the working length WL of the tube 170 is long relative to its diameter and/or wall thickness, the tube 170 can sag as shown in FIG. 14, and such sag can interfere with accurate cutting of a desired spiral pattern in the tube 170. Such a long working length WL can also lead to twisting of the tube 170 over the working length, as rotational friction in the bushing 304 resists rotation of the tube 170 driven by the chuck 302. The longer the working length WL, the more the tube tends to twist as a result of friction in the bushing 304. The resulting twisting of a long tube 170 leads to torsional error in the spiral pattern cut by the laser beam 308, which can be exacerbated as the torsion repeatedly builds up in the tube 170 and is released as the torsion periodically overcomes the friction in the bushing. In these circumstances, the tube near the bushing 304 tends to rotate in "bursts" rather than at a steady rate. Finally, at an overly long working length WL the tube 170 is susceptible to buckling as it is pushed toward the bushing 304 by the chuck 302.

Figure 15:
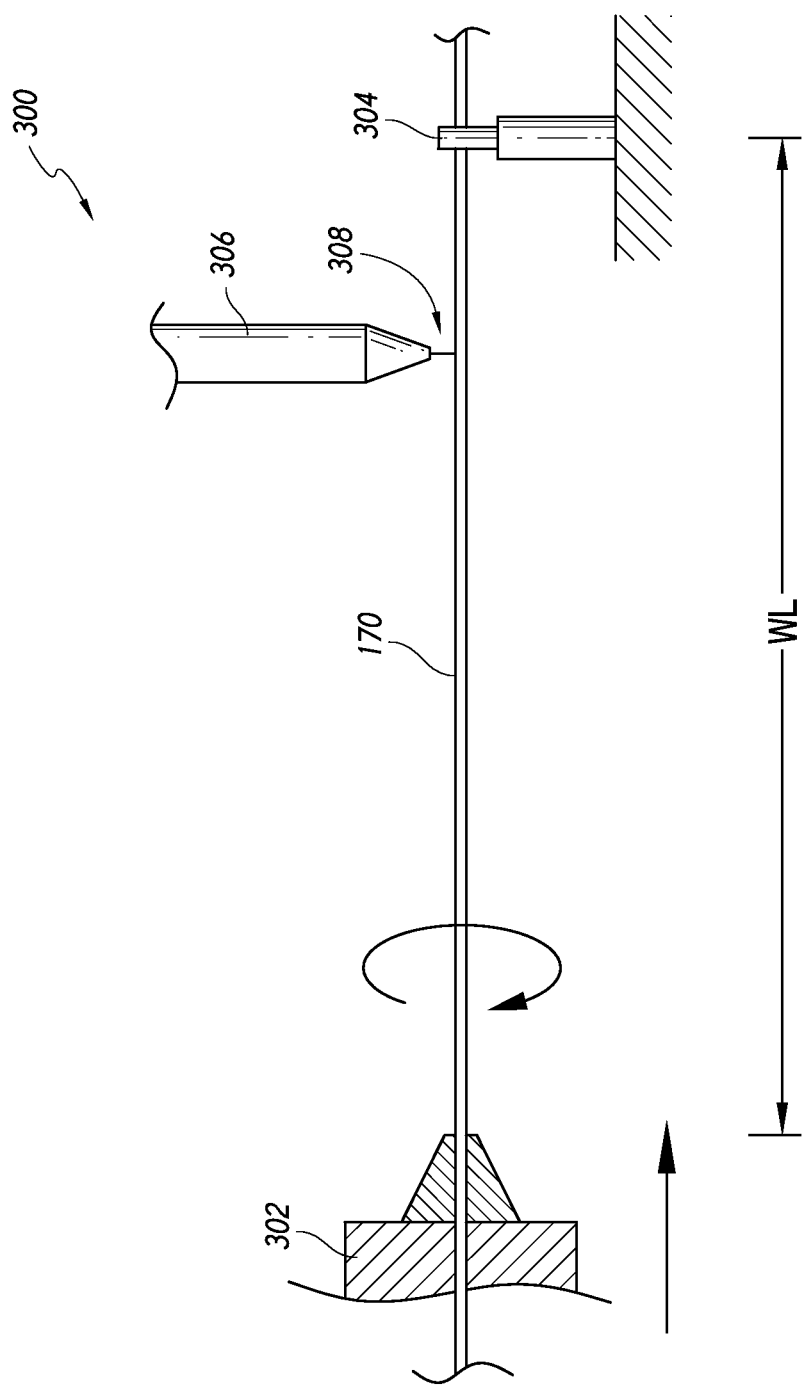
FIG. 15 is a schematic view of a laser cutting machine performing a laser cut and a catheter, according to some embodiments.

In contrast, FIG. 15 shows the benefits of a relatively short working length WL: sag, torsional error and/or buckling can be reduced or eliminated altogether. However, the inventors discovered that at the desired tube diameter and/or wall thickness the usable working length WL was much smaller than the desired overall length or cut length (e.g., 50 cm or more) of the tube 170. As an initial solution, the inventors thought to form such a longer spiral by linking together a number of separate, longitudinally adjacent spirals that are cut individually over an acceptably short working length WL. For example, five separate longitudinally adjacent cuts could be made, each at a working length of about 12 cm, in a "linked-together" fashion to form a long spiral cut of about 60 cm in length.

Figure 16:
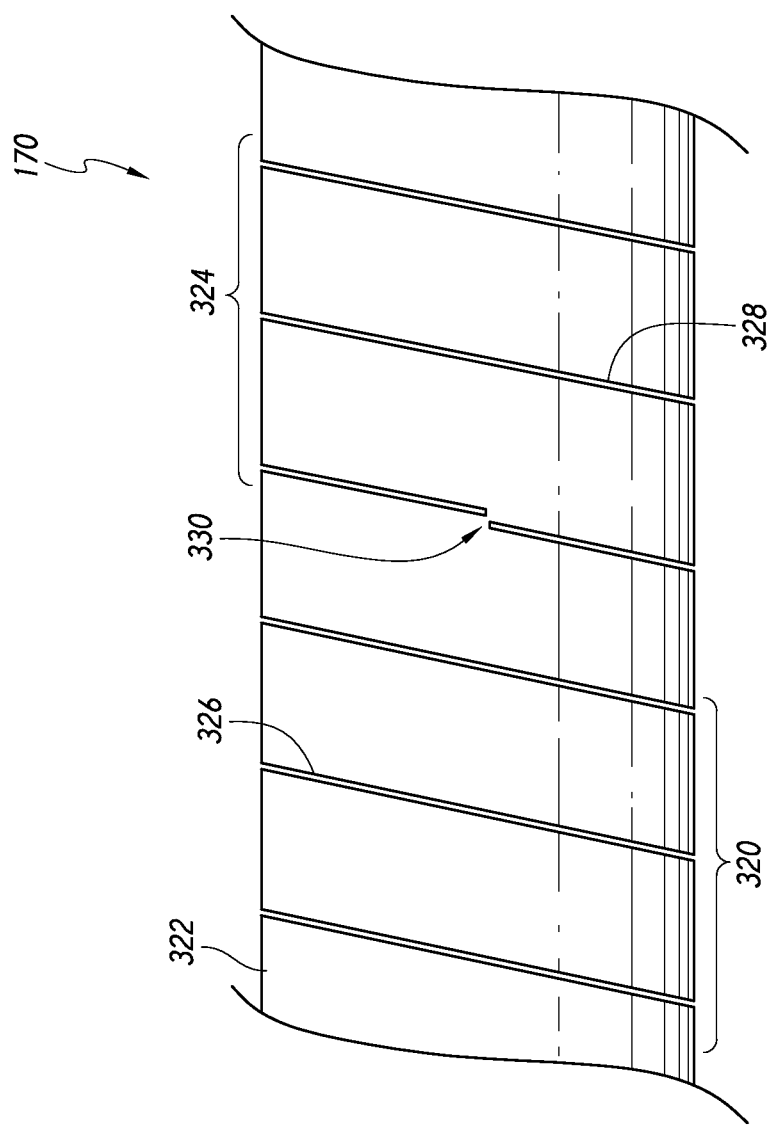
FIG. 16 is an enlarged side view illustrating drawbacks of prior art methods for creating a spiral cut in a tubular member.

FIG. 16 illustrates a problem that arises when attempting to link together separate spirals. The depicted tube 170 includes a first spiral 320 formed in the sidewall 322, and a second spiral 324 formed in the tube 170 and longitudinally adjacent to the first spiral 320. Each spiral 320, 324 comprises a respective void 326, 328 in the sidewall 322 that advances along the tube in a helical or spiraling form. The two spirals 320, 324 are longitudinally adjacent but not contiguous or continuous. Due to limitations in the laser cutting machine 300, the proximal end of the second spiral 324 cannot be positioned close enough to the distal end of the first spiral 320 to make the two spirals contiguous or continuous. Instead, the two spirals 320, 324 are separated by a discontinuity 330 between the distal end of the first spiral 320 and the proximal end of the second spiral 324. Such a discontinuity can be a source of cracks formed in the sidewall 322 when the tube 170 is subject to bending, twisting or other stresses encountered in vascular use.

Figure 17:
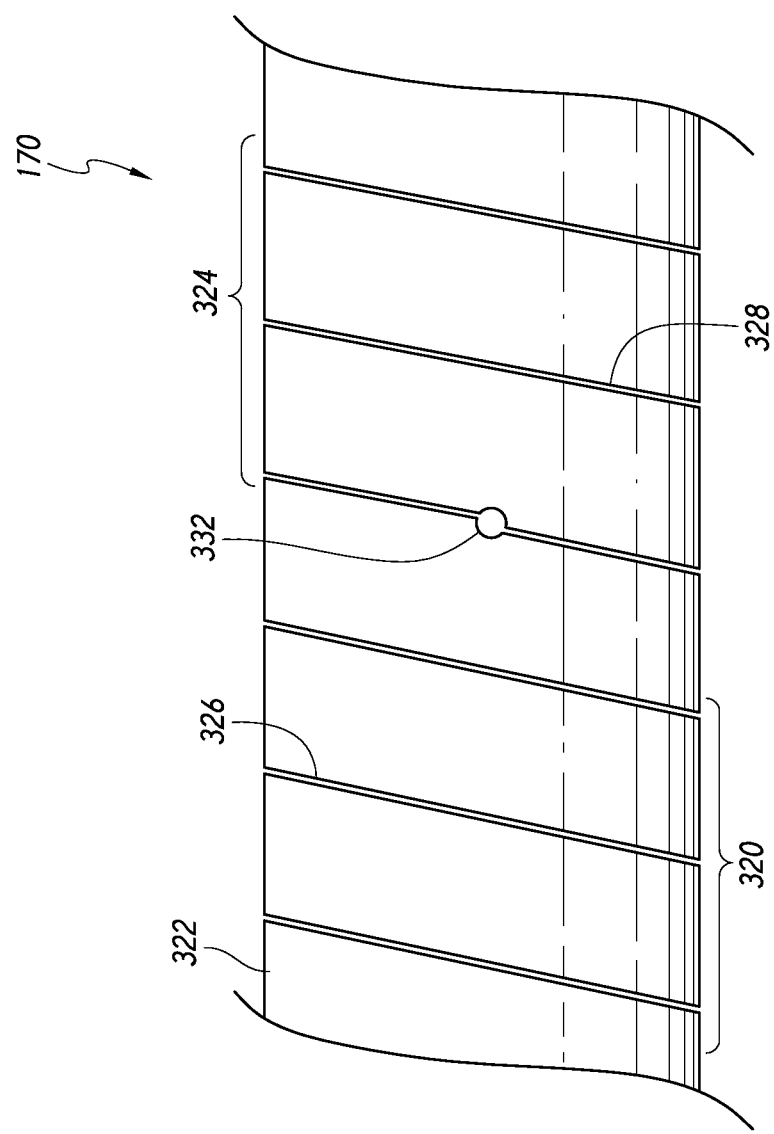
FIG. 17 is an enlarged side view of contiguous or continuous spiral cut in a tubular member, according to some embodiments.

FIG. 17 illustrates one embodiment of a solution to the problems of discontinuity and crack formation. In the embodiment of FIG. 17, the two spirals 320, 324 are formed in the same manner as in FIG. 16 but the spirals (and their respective voids 326, 328) are joined by a connection aperture 332. The connection aperture 332 can comprise an additional void that is formed (e.g., cut) in the sidewall 322 and is contiguous or continuous with the voids 326, 328 of the first and second spirals 320, 324. Accordingly, the connection aperture 332 and the voids 326, 328 can be considered to form a single, contiguous or continuous void extending along the contiguous or continuous first and second spirals 320, 324. The connection aperture 332 can comprise a circle, as shown in FIG. 17, or any other suitable shape such as an ellipse or polygon. A circle is thought to be advantageous due to a tendency to minimize the possibility of crack formation near the juncture of the voids 326, 328.

In various embodiments of the tube 170, a relatively long contiguous or continuous helical or spiral cut can be provided in the sidewall of the tube. For example, the tube 170 can have such a helical or spiral cut over any of the various cut lengths specified above or elsewhere herein for the tube 170. A tube 170 having such a helical or spiral cut have also have any one or combination of the various outside diameters, sidewall thicknesses and/or overall lengths specified above or elsewhere herein for the tube 170.

The long contiguous or continuous helical or spiral cut can be implemented as discussed herein, e.g., as with respect to FIG. 17. Two or more longitudinally adjacent spirals, cuts, slots or voids can be formed contiguously or continuously in the sidewall of the tube 170 and joined at their adjacent ends by connection aperture(s) 332 to form a spiral or helical cut, slot or void that is contiguous or continuous along the overall length or along the cut length of the tube 170. In some embodiments, the individual spirals, cuts, slots or voids can be about 15 cm in length, or 15 cm or less in length. These need not be uniform in length along the tube or cut length; for example the first or last spiral, cut, slot or void can be made somewhat shorter in order to achieve a cut length that is not an even multiple of the length of the individual spirals.

In some embodiments, one or more terminal apertures may be employed in the spiral or helical cut, slot or void. Such terminal aperture(s) can similar to any of the connecting apertures 332 disclosed herein, with the exception that they are positioned at one or both terminal ends of the spiral rather than at a juncture of two or more individual spirals. In still other embodiments of the tube 170, a spiral or helical cut, slot or void is employed with terminal aperture(s) at one or both terminal ends and no connecting apertures along the cut length. One or multiple such spirals may be formed in the sidewall 322 of a single tube 170. Where employed, the terminal aperture(s) can serve as a stress relief or measure against sidewall crack formation at the end(s) of the spiral. One example of a terminal aperture 334 can be seen in FIGS. 1-2 and 5-8.

Instead of or in addition to a spiral that is contiguous or continuous over a relatively long overall length or cut length of the tube 170, the pitch of the spiral can be controlled precisely over a long overall length or cut length. For example, the pitch of the spiral can vary over the cut length such that a pitch of a specific magnitude can prevail along a relatively short segment of the cut length, for example 5 mm or less, or 3 mm or less, or 2 mm or less, or about 1.0 mm. In this manner, the spiral pitch can be finely adjusted in small increments of the cut length thereby facilitating superior control over the mechanical properties of the tube 170 (e.g., bending stiffness, column strength) in various portions of the tube. Therefore, the tube 170 can have a pitch that varies in magnitude (including a specific "first pitch magnitude") along the overall length or cut length of the tube, and the first pitch magnitude can prevail along a first segment of the cut length. The first segment can have a length (measured along the axis A-A) of 5 mm or less, or 3 mm or less, or 2 mm or less, or about 1.0 mm. The magnitude of the pitch can change from the first magnitude at one or both ends of the first segment. The first segment can be located (e.g., in a contiguous or continuous void) anywhere along the cut length, including location(s) relatively far from the endpoints of the cut length, e.g., more than 10 cm away, or more than 20 cm away, or more than 30 cm away from an endpoint of the cut length.

Instead of or in addition to achievement of a particular pitch magnitude in one or more short segments of the cut length (and/or a spiral that is contiguous or continuous over a relatively long overall length or cut length of the tube 170), the pitch magnitude can be controlled precisely so that it can vary in relatively small increments. (The pitch can be expressed in mm/rotation.) For example, the pitch can vary in magnitude by 0.2 mm/rotation or less, or 0.1 mm/rotation or less, or 0.01 mm/rotation or less, or 0.005 mm/rotation or less. Thus is provided another manner in which the spiral can be finely controlled to facilitate desired mechanical properties in various portions of the tube 170. Therefore, the tube 170 can have a pitch that varies in magnitude (including a specific "first pitch magnitude") along the overall length or cut length of the tube, and the first pitch magnitude can prevail along a first segment of the cut length. The magnitude of the pitch can change from the first magnitude by 0.2 mm/rotation or less, or 0.1 mm/rotation or less, or 0.01 mm/rotation or less, or 0.005 mm/rotation or less, at one or both ends of the first segment. The first segment can be located (e.g., in a contiguous or continuous void) anywhere along the cut length, including location(s) relatively far from the endpoints of the cut length, e.g., more than 10 cm away, or more than 20 cm away, or more than 30 cm away from an endpoint of the cut length.

In one embodiment, the tube 170 has an overall length of 91 cm, cut length of 86 cm, outside diameter of 0.020", wall thickness of 0.003", spiral cut (slot) width of 25 microns, circular connection apertures with a diameter of 100 microns, and individual spiral cut lengths of about 15 cm.

Figure 18:
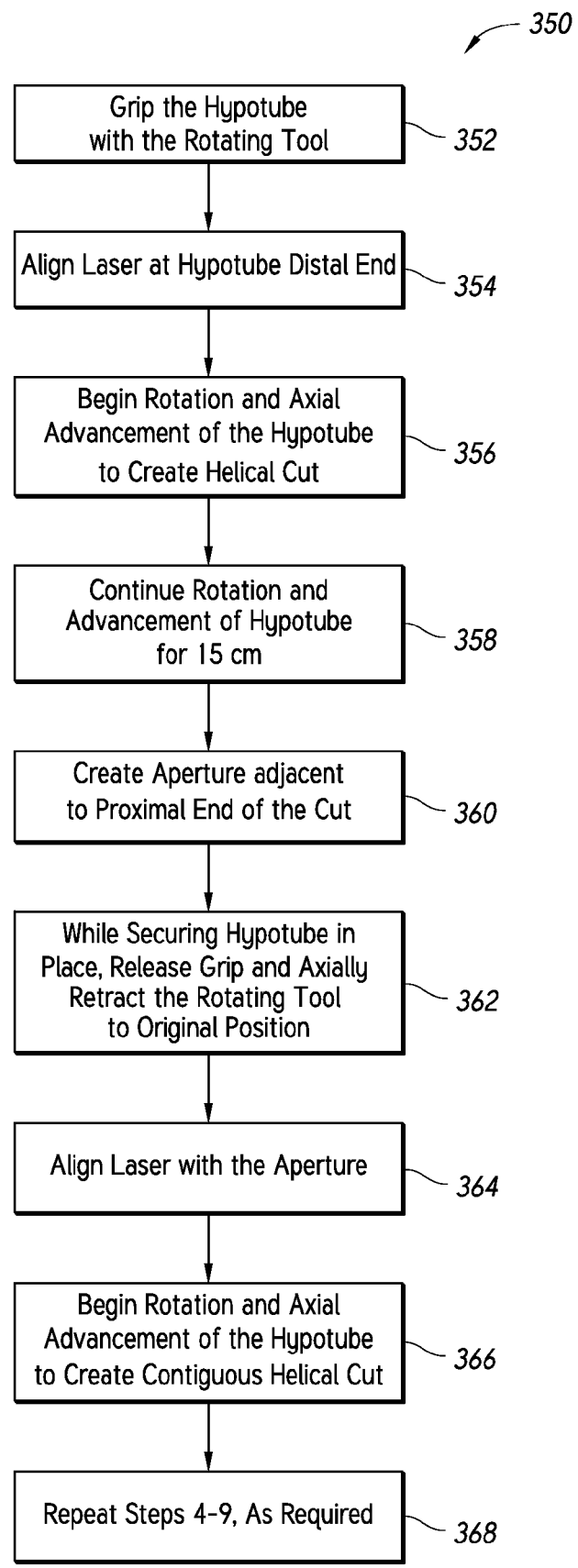
FIG. 18 is a flowchart illustrating representative steps of a method of performing a helical cut in a tubular member, according to some embodiments.

FIG. 18 depicts in flowchart form one embodiment of a method 350 of forming a relatively long spiral cut in the sidewall 322 of the tube 170, using equipment such as the laser cutting machine 300 described herein with reference to FIGS. 14-15. The method 350 begins at 352 by gripping the tube 170 with a rotating tool such as the chuck 302, followed at 354 by aligning or aiming the laser 306 with or at a portion of the tube 170, such as one of the proximal and distal ends thereof. Next, at 356 rotation and axial (lateral) advancement of the tube 170 relative to the laser 306 is commenced, at rates selected to obtain the desired spiral pitch, with the rotating tool or chuck 302. In this manner the laser 306 begins to cut a helical or spiral void in the sidewall of the tube 170. This is continued 358 until the void has been formed along the desired spiral segment length (e.g., 15 cm, or 15 cm or less). At 360, once the terminal end of the spiral segment has been formed, the rotating tool or chuck 302 (and/or the laser 306) is operated so as to form the connecting aperture 332 at the terminal end and contiguous or continuous with the just-formed spiral void. Then at 362 the tube 170 is secured in place relative to the laser 306 and bushing 304 via for example a selectively actuatable tube grip that can be incorporated into the bushing 304 or elsewhere in the machine 300, while the chuck 302 releases its grip on the tube 170 and retracts laterally away from the laser 306 and bushing 304 to the home position. Once in the home position, the chuck 302 grips the tube 170 once again and the actuatable tube grip releases the tube. At 364, the chuck 302 and/or laser 306 is operated to aim or align the laser at or with the aperture 332. Once the laser 306 is so aimed or aligned, the chuck or rotating tool can be operated again as in 356 to rotate and laterally advance the tube 170 relative to the laser 306. Thus the laser 306 begins to cut another spiral segment in the tube sidewall. Because of the initial positioning of the laser beam 308 in the aperture 332, the new spiral segment begins at the perimeter of the aperture and the new segment is contiguous or continuous with the aperture 332 and the previous segment. As indicated in 368, acts 358-366 can now be repeated until the desired number of spiral segments and connecting apertures 332 are formed, over a desired cut length of the tube 170.

Figure 19:
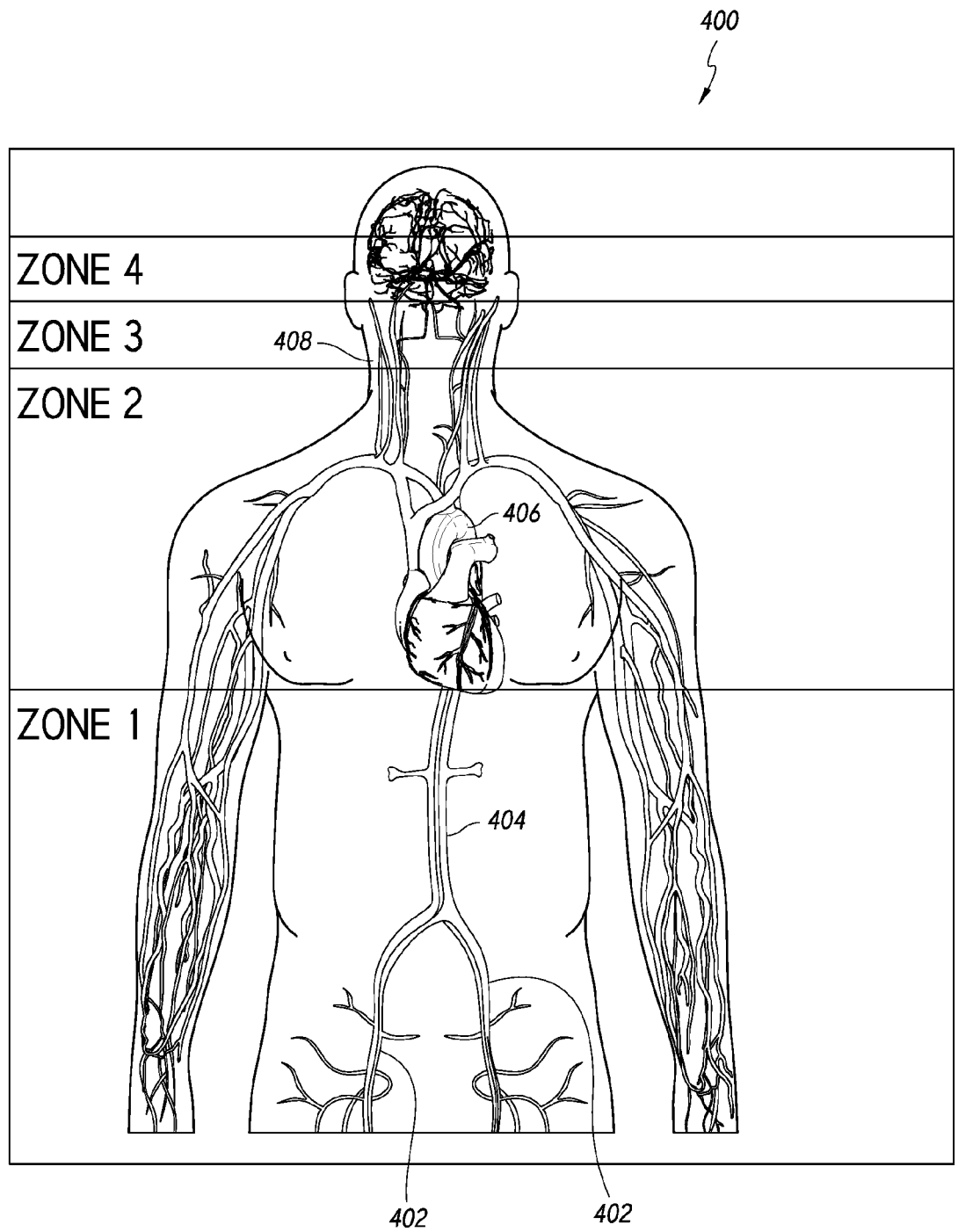
FIG. 19 is a schematic view of human vasculature, separated into representative zones, according to some embodiments.
Figure 20:
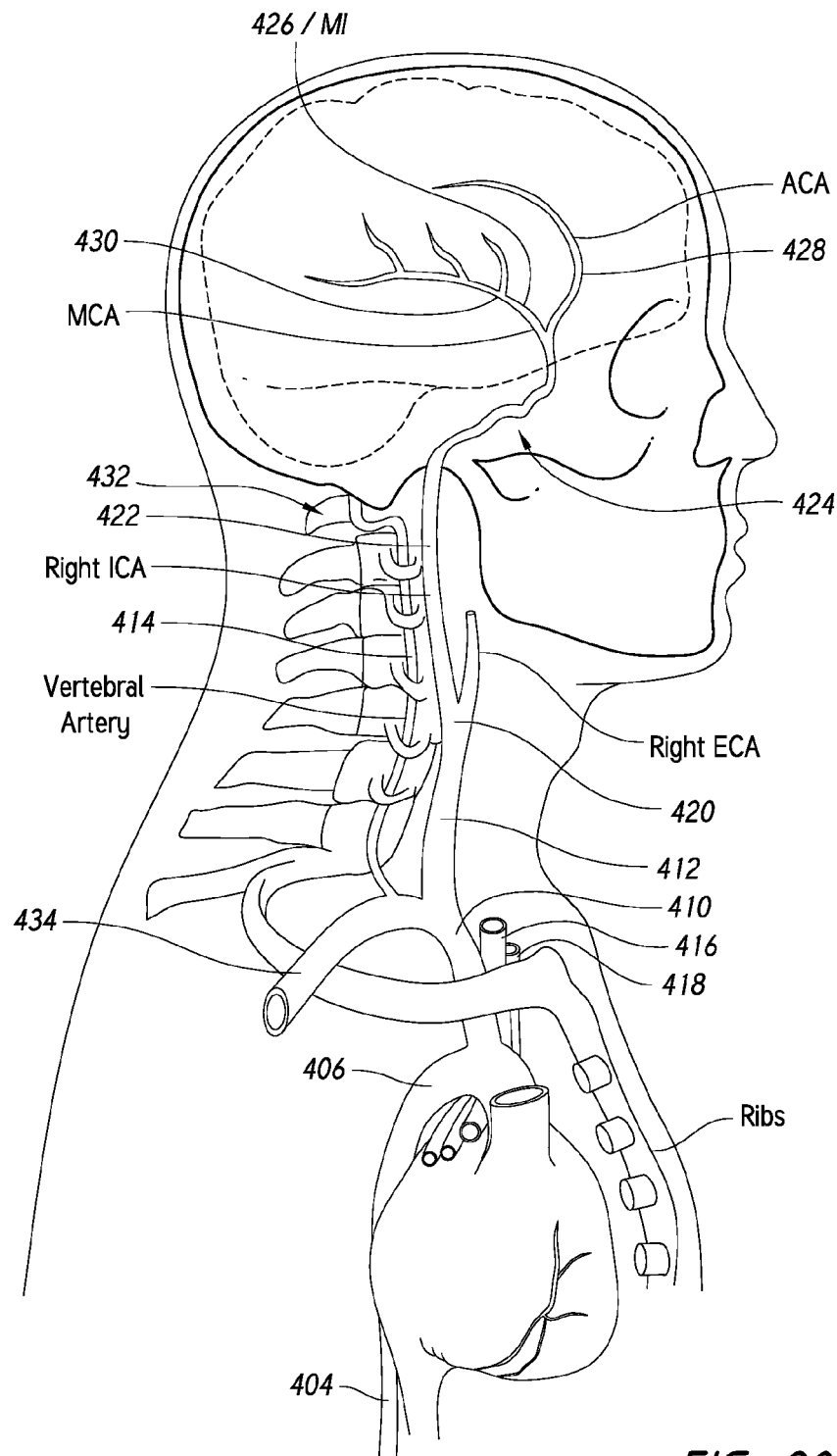
FIG. 20 is a schematic side view of human neurovasculature representative of some of the neurovasculature accessible with embodiments of the delivery systems disclosed herein.

FIGS. 19-20 show a vascular access route 400 that can be employed in some embodiments of methods of using the delivery system 100, particularly in such methods of using the delivery system 100 to deliver a medical device or the stent 200 to the neurovasculature. The route 400 can begin with percutaneous access into one of the femoral arteries 402 and then proceed to the abdominal aorta 404 and to the aortic arch 406. From the aortic arch 406 the route 400 can proceed up to and through the neck 408 through (A) the brachiocephalic artery 410 and (i) right common carotid artery 412 or (ii) right vertebral artery 414, or (B) the left common carotid artery 416, or (C) the left subclavian artery 418 and left vertebral artery (not shown). When the route 400 passes through the (right) common carotid artery 412 it can then proceed past the (right) carotid bifurcation 420 into the (right) internal carotid artery (ICA) 422. (The ICA commonly displays high tortuosity as shown at 424.) At the end of the ICA the route 400 can continue into one of the ICA's terminal branches, the middle cerebral artery (MCA) 426 or the anterior cerebral artery (ACA) 428. In the MCA 426 the route 400 can proceed through the M1 segment, to or beyond the M1 bifurcation 430.

When the route 400 passes through the (right) vertebral artery 414, it frequently encounters vertebral tortuosity such as shown at 432. From either vertebral artery, the route 400 can proceed through the basilar artery (not shown) to or past the basilar tip, posterior cerebral arteries (not shown), or posterior communicating arteries (not shown).

Instead of beginning at access via the femoral artery 402, the route 400 may begin at access via the left 418 or right 434 subclavian artery and proceed into the aortic arch 406, right common carotid artery 412 or right vertebral artery 414, and beyond as described above.

As seen in FIG. 19, the various embodiments of the vascular access route 400 may be divided into up to four zones: Zone 1, characterized by the relatively straight, large-diameter femoral artery 402 and abdominal aorta 404; Zone 2, including the sharply turning aortic arch 406 and its junctions with the arteries branching from the arch 406 toward the neck 408; Zone 3, with the common carotid and proximal vertebral arteries, and proximal ICA; and Zone 4, characterized by highly tortuous segments of the ICA 422 or vertebral artery 414, and/or smaller-diameter vessels that are frequently tortuous, such as the MCA 426 and leading up to or beyond the M1 bifurcation 430.

In some embodiments, the tube 170 can comprise a spiral-cut tube and the pitch of the spiral can vary along the overall length and/or cut length of the tube. The pitch can vary at a constant rate, or a non-constant rate. One or more segments of the cut length can have constant pitch, and these can be combined with one or more segments that have varying pitch. The tube 170 can incorporate spiral-cut and non-spiral-cut portions.

In some embodiments, the cut portion of the tube 170 can have two or more segments wherein the pitch is substantially constant (e.g., to impart mechanical properties suited to a desired one of the Zones indicated in FIG. 19) and these constant-pitch segments can be joined by segments in which the pitch varies. For example, a proximal segment may have a relatively high substantially constant pitch (in mm/rotation) to make the tube 170 relatively stiff in that segment, and a distal segment may have a relatively low substantially constant pitch (in mm/rotation) to make the tube 170 relatively flexible in that segment. These two segments may be joined by a varying-pitch segment in which the pitch is gradually reduced from that of the proximal segment to that of the distal segment. In this manner the tube 170 can incorporate a stiff proximal section for pushability and column strength, and a flexible distal section for navigability in tortuous vessels. The tube 170 can accommodate a relatively large change in pitch and stiffness between the proximal segment and the distal segment by making the change in pitch sufficiently gradual along the length of the varying-pitch segment. This can be done by incorporating a sufficient number of pitch transitions along the length of the varying-pitch segment. The number of pitch transitions per unit length of the tube can be considered a pitch transition density or PTD.

If, in a varying-pitch segment positioned between two segments that differ significantly in pitch or stiffness, the PTD is too low, the change in pitch/stiffness at any individual pitch transition will be relatively high; as a result the tube 170 may have an unduly high tendency to kink at such an individual pitch transition as the tube is advanced through a tortuous vessel and/or a high push force is exerted on the tube. In other words, if the tube incorporates an abrupt transition from a high-stiffness section to a low-stiffness section, the tube may be likely to kink at the transition point or segment when encountering a sharp turn in a vessel and/or application of a high push force.

Therefore, in order to accommodate in the tube 170 multiple segments that differ significantly in pitch/stiffness (and for example thereby tailor the mechanical properties of the tube segments to the various anatomical regions of the access route 400), without unduly increasing the tendency of the tube to kink, it can be useful to employ varying-pitch segments or transition zones that have a relatively high PTD or a relatively high overall number N of transitions. When the tube is forced to bend at or near a transition zone characterized by sufficiently high PTD and/or sufficiently high N, the bend becomes "spread" among the individual transitions in the transition zone, resulting in a gradual, arcing bend rather than a sudden, sharp kink.

Figure 21:
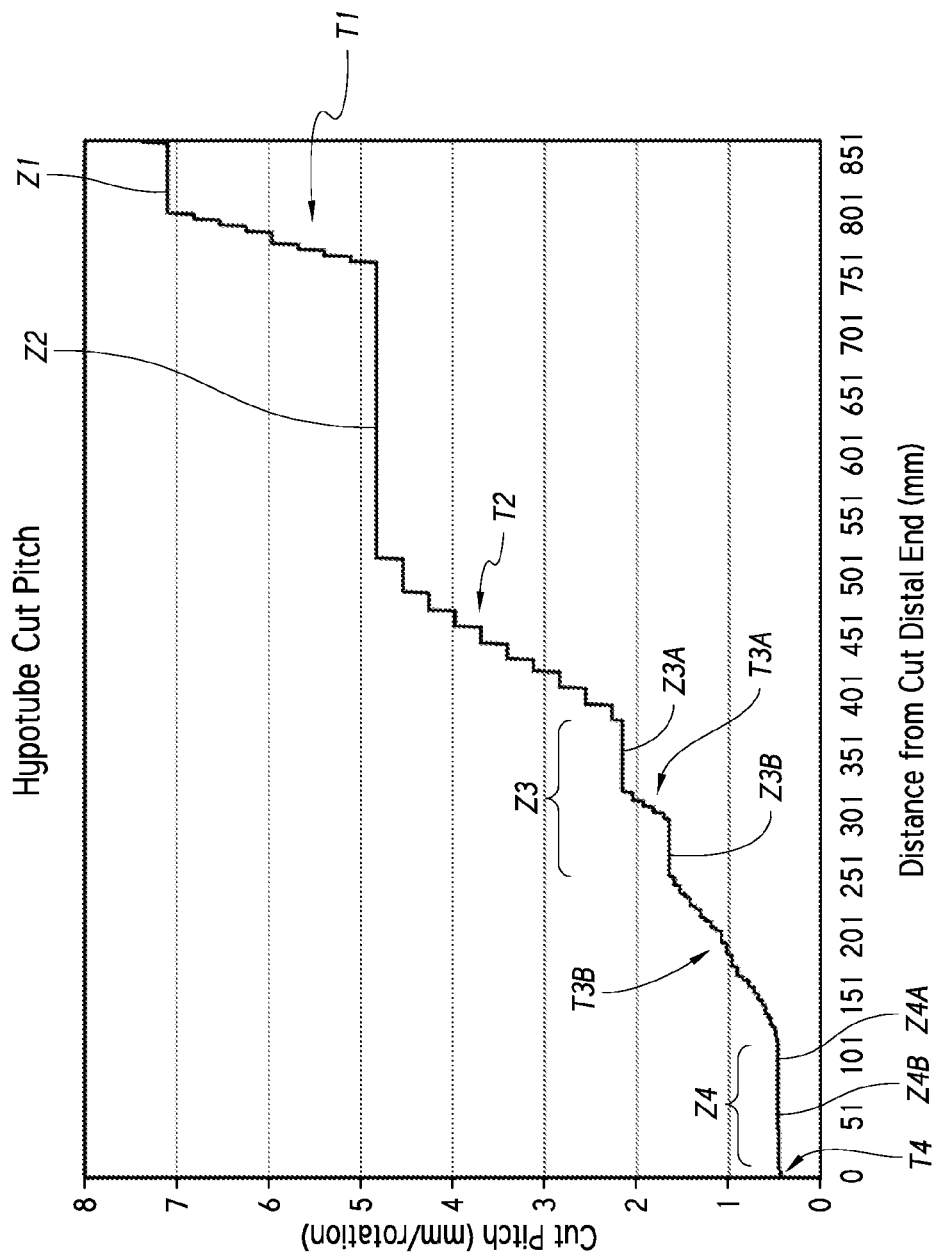
FIG. 21 is a graph illustrating the relationship between cut pitch and distance from a cut distal end of a helical cut in a tubular member, according to some embodiments.

FIG. 21 illustrates a varying pitch that may be used in some embodiments of the tube 170. The tube 170 may incorporate one or more multiple segments or flex zones of substantially or relatively constant pitch or stiffness, such as one, some or all of the zones Z1, Z2, Z3 (which can include two smaller zones Z3A, Z3B), and/or Z4 (which can include two smaller zones Z4A, Z4B). The flex zones can decrease in pitch/stiffness as the tube extends distally, e.g., with Z1>Z2>Z3>Z4 in pitch and/or stiffness. The zone Z1 can have a pitch and/or stiffness that is sufficiently flexible for navigation in Zone 1 of the access route 400 (FIG. 19), through the femoral artery 402 and abdominal aorta 404, while retaining pushability and column strength to move the distal portions of the core assembly 140 through Zones 2, 3 and 4. The zone Z2 can have a pitch and/or stiffness that is sufficiently flexible for navigation in Zone 2 of the access route 400, particularly across the aortic arch and making a turn from the arch and extending into the one of the arteries leading to the neck (brachiocephalic 410, left common carotid 418 or left subclavian 418). The zone Z3 can have a pitch and/or stiffness that is sufficiently flexible for navigation in Zone 3 of the access route 400, particularly in the common carotid artery 412, or proximal portions of the internal carotid artery 422 or vertebral artery 414. The zone Z4 can have a pitch and/or stiffness that is sufficiently flexible for navigation in Zone 4 of the access route 400, particularly in the tortuous distal portions of the internal carotid artery 422 (such as the carotid siphon) and vertebral artery 414, and/or the middle cerebral artery 426 to the M1 bifurcation 430.

The flex zones Z1, Z2, Z3, Z4 can vary significantly relative to each other in pitch and/or stiffness in order to accommodate their respective target anatomies. For example, the zone Z4 can have a bending stiffness less than 5%, or less than 3%, or less than 2%, or less than 1% of the bending stiffness of the tube 170 when uncut. The zone Z3 can have a bending stiffness (A) greater than 8%, or greater than 10%, or greater than 12% of the bending stiffness of the tube 170 when uncut; and/or (B) less than 22%, or less than 20%, or less than 18%, or less than 17% of the bending stiffness of the tube 170 when uncut. The zone Z2 can have a bending stiffness (A) greater than 27%, or greater than 29%, or greater than 30% of the bending stiffness of the tube 170 when uncut; and/or (B) less than 36%, or less than 34%, or less than 33% of the bending stiffness of the tube 170 when uncut. The zone Z1 can have a bending stiffness (A) greater than 38%, or greater than 40%, or greater than 42% of the bending stiffness of the tube 170 when uncut; and/or (B) less than 50%, or less than 46%, or less than 44% of the bending stiffness of the tube 170 when uncut. The foregoing bending stiffness values and ranges can be implemented with reference to a tube 170 of any dimensions disclosed herein, including but not limited to a tube 170 having an outside diameter of 0.040" or less and/or a wall thickness of 0.010" or less. Such a tube may be constructed from materials including polymers, and metals including nitinol and stainless steels such as 304 or 304L stainless steel. One suitable tube 170 is constructed from 304L stainless steel with an outside diameter of 0.020" and a wall thickness of 0.003".

Instead of or in addition to the bending stiffnesses specified above, the zones Z1, Z2, Z3 and/or Z4 can have one, some or all of the following bending stiffnesses in Newtons times millimeters squared (N*mm^2): Z4, less than 12, less than 10, less than 8, or about 5; Z3B, 60-100, or 70-90, or about 80; Z3A, 90-130, 100-120, or about 110; Z2,180-220, 190-210, or about 205; and/or Z1, greater than 250, greater than 270, or about 280, or 250-310, or 270-290. The uncut tube 170 can have a stiffness of 600-700, 625-675, or about 650. The foregoing bending stiffness values and ranges can optionally be normalized (to account for any differences in measuring equipment) with reference to a value of 340 N*mm^2 for 0.017" diameter solid wire made from 304 stainless steel.

One, some or all of transition zones T1, T2, T3A and/or T3B can optionally be provided to incorporate these differences in pitch/stiffness while minimizing any resulting tendency of the tube to kink between the flex zones. The transition zones T1, T2, T3A and/or T3B can have relatively high PTD or N, as discussed above. For example, the transition zone T1 can have a PTD greater than 1.0 transitions per centimeter (T/cm), or of 2.0 T/cm or greater, or of about 2.0 T/cm; the transition zone T2 can have a PTD greater than 0.5 T/cm, or of 0.74 T/cm or greater, or of about 0.74 T/cm; the transition zone T3A can have a PTD greater than 1.5 T/cm, or of 2.2 T/cm or greater, or of about 2.2 T/cm; the transition zone T3B can have a PTD greater than 1.0 T/cm, or of 1.8 T/cm or greater, or of about 1.8 T/cm; and the transition zone T4 can have a PTD greater than 6.0 T/cm, or of 8.9 T/cm or greater, or of about 8.9 T/cm.

The transition zone T3B can provide a transition in flexibility from the relatively soft zone Z4, which can have a bending stiffness (such as any of those discussed above for Z4) suitable for navigating the distal ICA and M1 segment of the MCA, up to the stiffer zone Z3. Along the transition zone T3B, the pitch can increase significantly from the pitch employed in the zone Z4, by over 150%, over 200%, over 250%, or about 254%, to the pitch employed in zone Z3. The transition zone T3B can comprise a number of individual pitch transitions, such that the average overall percent increase in pitch achieved per individual transition is 15% or less, or 12% or less, or 11% or less, or 10.5% or less, or about 10.1%. (Such an average is computed by dividing the total percent increase in pitch achieved in the transition zone by the total number of transitions in the zone.) Instead of or in addition to any of these averages, the transition zone T3B can achieve a reduction in stiffness of greater than 75%, or greater than 85%, or greater than 90%, or about 94.5%, from the zone Z3 (particularly Z3B) to the zone Z4.

The transition zone T2 can provide a transition in flexibility from the zone Z3, which can have a bending stiffness (such as any of those discussed above for Z3) suitable for navigating the common carotid artery, proximal internal carotid artery, and/or proximal vertebral artery, to the stiffer zone Z2 which can have a stiffness (such as any of those discussed above for Z2) suited to crossing the aortic arch and/or extending into one of the arteries leading from the arch toward the neck. Along the transition zone T2, the pitch can increase significantly from the pitch employed in the zone Z3, by over 80%, over 100%, over 120%, or about 125%, to the pitch employed in zone Z2. The transition zone T2 can comprise a number of individual pitch transitions, such that the average overall percent increase in pitch achieved per individual transition is 20% or less, or 15% or less, or 13% or less, or about 12.5%. (Such an average is computed by dividing the total percent increase in pitch achieved in the transition zone by the total number of transitions in the zone.) Instead of or in addition to any of these averages, the transition zone T2 can achieve a reduction in stiffness of greater than 35%, or greater than 40%, or greater than 45%, or about 47%, from the zone Z2 to the zone Z3.

The transition zone T1 can provide a transition in flexibility from the zone Z2, to the stiffer zone Z1 which can have a stiffness (such as any of those discussed above for Z1) suited to passing through the femoral artery and abdominal aorta, and providing pushability for the more distal portions of the core assembly 140. Along the transition zone T1, the pitch can increase significantly from the pitch employed in the zone Z2, by over 35%, over 40%, or about 45%, to the pitch employed in zone Z1. The transition zone T1 can comprise a number of individual pitch transitions, such that the average overall percent increase in pitch achieved per individual transition is 10% or less, or 8% or less, or 6% or less, or about 5.6%. (Such an average is computed by dividing the total percent increase in pitch achieved in the transition zone by the total number of transitions in the zone.) Instead of or in addition to any of these averages, the transition zone T1 can achieve a reduction in stiffness of greater than 15%, or greater than 20%, or greater than 25%, or about 27%, from the zone Z1 to the zone Z2.

Some, one or all flex zones Z1, Z2, Z3, Z4 can have a length greater than 30 mm, or greater than 40 mm. For example, the zone Z4 can have a length of 60 mm or more, or 80 mm or more, or 80-120 mm, or about 100 mm. The zone Z3B can have a length of 40-60 mm, or about 50 mm and the zone Z3A can have a length of 50-70 mm, or about 60 mm. The zone Z2 can have a length greater than 200 mm, or 200-300 mm, or 225-275 mm, or about 250 mm. The zone Z1 can have a length of 50-70 mm, or about 60 mm.

Instead of or in addition to any one or combination of the lengths specified above, the zones can be situated along the tube 170 with their respective distal ends located at the following distances from the distal end of the tube, or from the proximal end of the stent 200: Z4, 8-12 mm, or about 10 mm; Z3B, 225-275 mm, or 240-260 mm, or about 250 mm; Z3A, 300-340 mm, or 310-330 mm, or about 320 mm; Z2, 480-540 mm, 490-530 mm, or about 515 mm; and/or Z1, 780-820 mm, or 790-810 mm, or about 800 mm. By employing these locations along the tube, the zones Z1, Z2, Z3 and/or Z4 can be configured to occupy the anatomical regions described herein as corresponding to such region(s) when the distal end of zone Z4 or the intermediate region 166 is located within the M1 segment of the MCA.

The tube 170 can optionally include a transition zone T4 at the distal end of the cut length, e.g., distal of and adjacent to the zone Z4. The transition zone T4 can be configured to serve a "steering" function to point the tube 170 in the direction of travel of the distal portions of the core member 160 (e.g., distal wire 172) as those distal portions navigate turns within the vasculature. Accordingly the zone T4 can have a relatively high PTD (e.g., over 5 T/cm, over 7 T/cm, or about 9 T/cm), a relatively short length (e.g., less than 15 mm, or less than 12 mm, or 8-10 mm, or about 9 mm), and/or an average stiffness less than the stiffness of the zone Z4 (e.g., a stiffness that decreases from that of zone Z4 as zone T4 extends distally).

Numerous parameters for various aspects of a spiral cut of the tube 170 are specified above. The scope of the present disclosure includes any single one or any combination of any number of the specified parameters. No one parameter, and no one value of any such parameter, should be regarded as essential.

Referring now to FIGS. 22-25, in some embodiments, the core assembly 140 (and optionally together with the stent 200 or medical device carried thereby) can be packaged in, or pre-loaded in an introducer sheath 450 to thereby form a pre-load assembly 460. Such a pre-load assembly 460 and introducer sheath 450 can facilitate rapid transfer of the core assembly 140 and stent 200 into the catheter 110 via the hub 122 and/or proximal end 112. This can enable, for example, the catheter 110 to be selected independently of the core assembly 140 and stent 200. The core assembly 140 and stent 200 can be packaged in a pre-loaded condition in the introducer sheath 450 (e.g., with the resulting pre-load assembly in a coiled configuration), and the introducer sheath connected to the proximal end of the catheter 110 to enable delivery of the stent 200 via the catheter 110. The introducer sheath can have an inside diameter that is approximately equal to the inside diameter of the catheter 110, and a tapered distal tip (not shown) to facilitate connection with the proximal end of the catheter 110.

Figure 22:
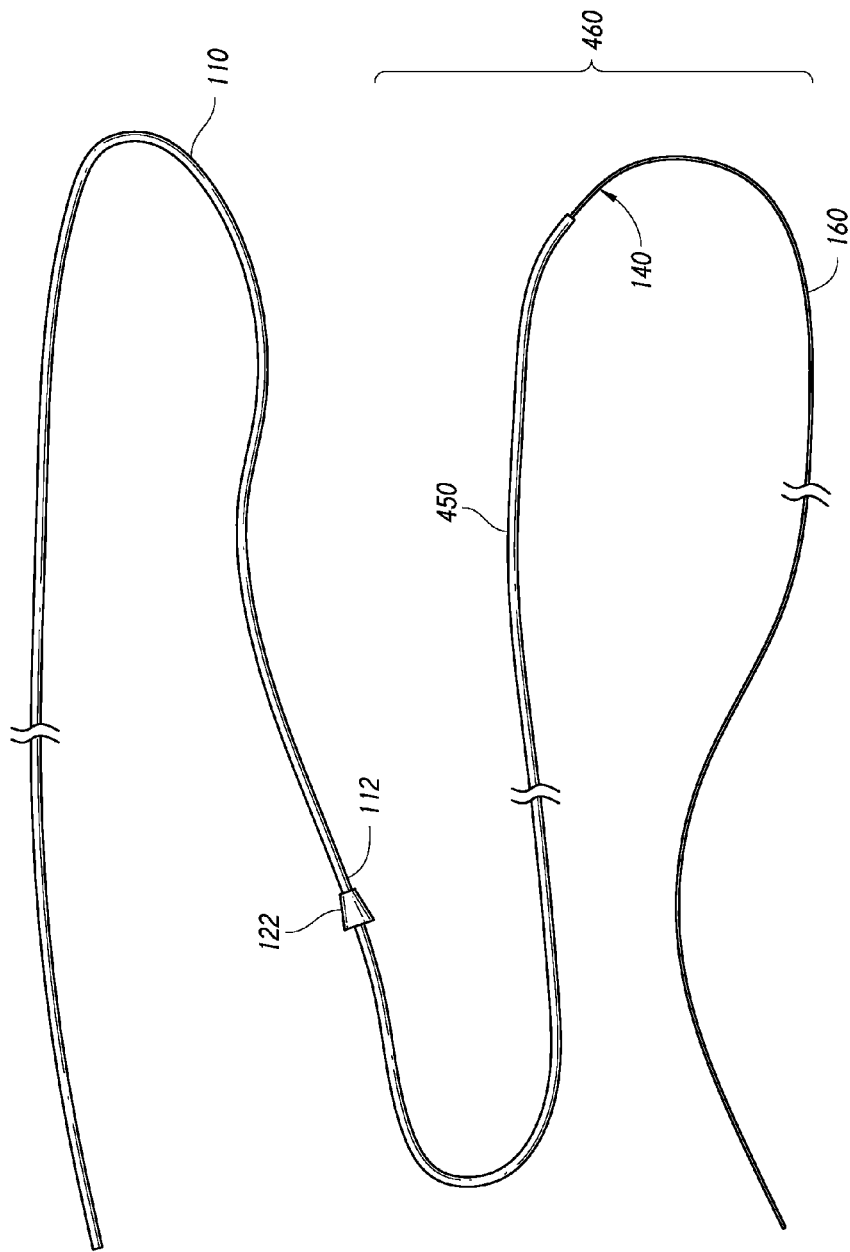
FIG. 22 is a perspective view of a medical device delivery system, according to some embodiments.

As seen in FIGS. 22-25, after connection of the distal end of the introducer sheath 450 to the proximal end 112 of the catheter 110, the pre-load assembly 460 and catheter 110 are in the state shown in FIGS. 22-23, in which the core assembly 140 and stent are inside the sheath 450, proximal of the catheter 110. From this state the core assembly 140 and stent 200 can be advanced into the catheter 110 by gripping the exposed portion of the core member 160 proximal of the sheath 450, and pushing the core assembly 140 distally, thereby reaching the state shown in FIG. 24, with the stent 200 and much of the core assembly now located in the catheter 110. At this point the introducer sheath 450 can be disconnected from the catheter 110 and refracted over the proximal portion of the core member 160, either to expose a portion of the core member proximal of the catheter 110, or retracted entirely from the core member 160 and discarded. FIG. 25 shows the result of complete retraction of the sheath 450; a portion of the core member 160 is exposed for gripping proximal of the proximal end of the catheter 110. The user can then grip the core member 160 there and push the core assembly 140 and stent 200 further distally into the catheter 110 to proceed with delivery and/or deployment of the stent according to any of the methods disclosed herein.

The introducer sheath 450 can be made relatively long, e.g., 80 cm or more, or 90 cm or more, or 100 cm or more, or about 106 cm. Alternatively, the introducer sheath 450 can have a length equal to or longer than the length of the core assembly 140 from the distal tip to the proximal end of the cut length of the tube 170. As still another alternative, the length of the introducer sheath 450 can be sufficient to cover the entire length of the core assembly 140 from its distal tip extending proximally, except for a proximal grip region 462 of the core member 160 that is at or near the full insertable diameter of the core member 160 and is at or near full stiffness (e.g., lacks significant flexibility enhancements such as a spiral cut or a pattern of slots or other openings formed or cut in the sidewall of a tube, or lacks significant tapering in the case of a wire). In the case of the core assembly 140 shown in FIGS. 1-8, the exposed proximal grip region can comprise the proximal wire 168 and/or an uncut portion of the tube 170.

An introducer sheath of such length advantageously prevents the user from gripping or pushing on any of the "soft" or highly flexible portions of the core assembly 140 or core member 160 when advancing the core assembly 140 and stent 200 into the catheter 110, thus protecting such soft/flexible portions from damage. In addition, the introducer sheath 450 helps resist buckling or kinking of the core member 160 while the core assembly 140 is being pushed into the catheter 110 via the grip region 462, by constraining the amount to which the core member 160 can bend sideways under a compressive load.

As may be observed in FIGS. 23-25, before advancement of the core assembly 140 and stent 200 distally from the sheath 450 into the catheter 110, the sheath 450 covers the entire core assembly 140 and core member 160 except for the proximal grip region 462. The user is therefore forced to grip the core member 160 in the proximal grip region 462 to advance it into the catheter 110 (and/or prevented from grasping the core member 160 anywhere else). After reaching the state shown in FIG. 24, the proximal grip region 462 is still the only exposed portion of the core assembly 140, although a smaller portion of the region 462 is now exposed. (Optionally, the sheath 450 and core member 160/proximal wire 168 can be sized so that the proximal end of the core member 160 is flush with the proximal end of the sheath 450 upon reaching the state shown in FIG. 24, or any similar state wherein the stent 200 is proximal of the distal end 114 of the catheter 110.) After partial or complete retraction of the introducer sheath 450 (FIG. 25), the proximal grip region 462 is again the only portion of the core assembly 140 and core member 160 that is exposed proximal of the catheter 110. Again the user can grip the core member 160 only in the proximal grip region while pushing the core assembly 140 distally into the catheter 110.

Instead of or in addition to the length(s) specified above, the introducer sheath can have a sidewall which is translucent and/or contrast-enhancing. For example, the sidewall can be of a translucent white or translucent yellow color (as opposed to clear or transparent). Optionally, a translucent white sidewall can be made by including titanium dioxide in the material or polymer used for forming the sheath 450. With a translucent and/or contrast-enhancing sidewall, the fluorosafe marker(s) 176 can be made black in color, such as via surface oxidation of the proximal wire 168 with a laser or other heat treatment.

The translucent and/or contrast-enhancing sheath 450 can enhance visibility of the fluorosafe marker 176, in a manner superior to a transparent sheath 450, during advancement of the core assembly 140 (particularly when the sheath lumen contains a liquid such as saline) as shown in FIGS. 23-25. Prior to advancement of the core assembly 140 (FIG. 23), the fluorosafe marker 176 can be located proximal of the sheath 450, or in a proximal portion of the sheath 450. As the core assembly 140 and core member 160 are advanced into the catheter 110, the fluorosafe marker 176 is visible through the sidewall of the sheath 450 so that the user can observe the movement of the fluorosafe marker 176 within the sheath 450 until it reaches a position near the proximal end of the catheter (FIGS. 24, 25), thereby signaling to the user that the distal end of the stent 200 is about to exit the distal end 114 of the catheter 110. Recognizing this, the user can stop advancement of the core assembly 140 until ready to move further and deploy the stent 200. If the proximal end of the core member 160 reaches the proximal end of the sheath 450 before the fluorosafe marker 176 and stent 200 reach their positions shown in FIG. 24, the user can nonetheless note the position of the fluorosafe marker 176 through the sidewall of the sheath 450, to enable the user to find the marker 176 upon refraction and/or removal of the sheath 450. After retraction/removal of the sheath 450, the user can further advance the core member 140 distally (if necessary) to reach the state shown in FIG. 25, in which the fluorosafe marker 176 is just proximal of the proximal end 112 of the catheter 110 and the distal end of the stent is just proximal of the distal end 114 of the catheter 110. By observing the position of the fluorosafe marker 176, the user recognizes that the stent is soon to emerge from the distal end 114 of the catheter 110, and that it is now appropriate to activate fluoroscopic imaging to observe deployment of the stent into a blood vessel via such imaging. Heretofore during some or all of the advancement of the core assembly 140, the imaging had been kept deactivated to minimize patient exposure to radiation.

Figure 26:
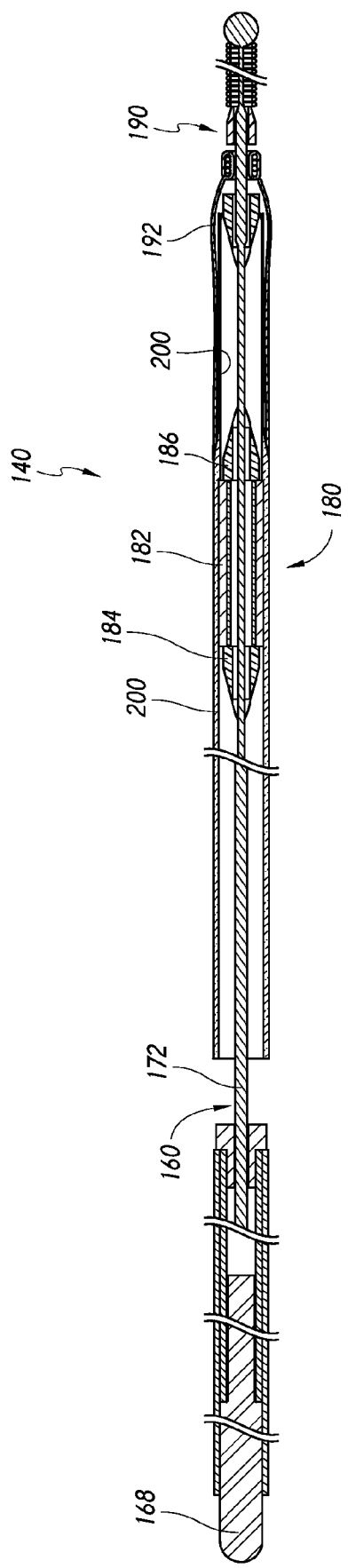
FIG. 26 is a side, cross-sectional view of another core assembly, according to some embodiments.

FIG. 26 shows an additional embodiment of the core assembly 140 (with the stent 200) which can be identical in structure, function and method(s) of use to any of the other embodiments of the core assembly 140 described herein, except as further described as follows. In this embodiment, the proximal device interface 180 (including for example the proximal engagement member 182 and/or its restraints 184, 186) can be located in a distal portion of the stent 200, e.g., in the distal half of the stent 200, overlapping with or just proximal of the distal cover 192, or partially or wholly overlapping with the distal cover 192. Further, according to some embodiments, that the proximal device interface 180 be located only in the distal half of the stent 200 does not mean that the proximal device interface 180 extends along the entire distal half, but instead can refer to embodiments in which the proximal device interface extends along less than the distal half.

For example, the proximal engagement member 182 can be located so that its distal end is less than 1 mm proximal of the proximal end of the cover 192, or distal of such location. With the proximal device interface 180 and proximal engagement member 182 so located, the member 182 can urge the stent 200 distally primarily by "pulling" the stent from a distal portion thereof, applying force to a point or region in a distal portion, or near the distal end, of the stent. When moving or pulling the stent in this fashion, the amount of push force necessary to be exerted through the core member 160 is reduced because the tendency of the stent to expand radially (as can occur when it is pushed distally and longitudinally compressed by a force applied to a point or region near the proximal end of the stent) is reduced. Optionally, in the embodiment of FIG. 26 there may be no additional structures proximal of the engagement member 182 and/or interface 180 that transmit force from the core member 160 or wire 172 to the stent 200.

Figure 27:
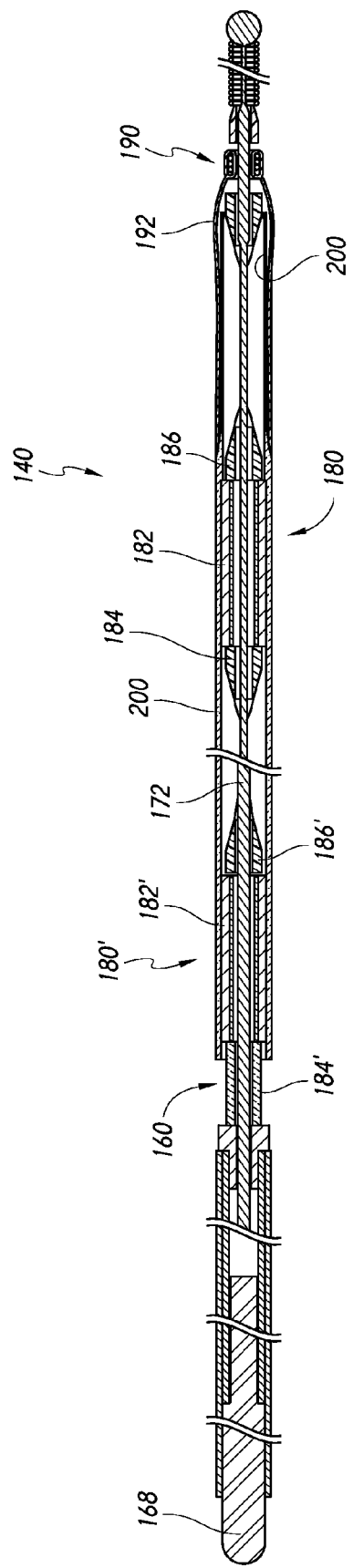
FIG. 27 is a side, cross-sectional view of another core assembly, according to some embodiments.

FIG. 27 depicts an additional embodiment of the core assembly 140 which can be identical to the embodiment of FIG. 26, with the addition of a second proximal device interface 180' in a proximal portion of the stent 200, in addition to the distally located interface 180 described with reference to FIG. 26. The second interface 180' and/or its engagement member 182' can be located in a proximal portion of the stent 200, e.g., near the proximal end or in the proximal half of the stent 200. In such an arrangement, both the interfaces 180, 180' and/or members 182, 182' can urge the stent 200 distally in response to a distal push force exerted on the core member 160, thereby both "pulling" the stent from the distal portion and "pushing" it from the proximal portion. This can also reduce the amount of push force necessary to be exerted through the core member 160 to advance the stent into or through the catheter 110. In addition, the interface 180' and member 182' when located near the proximal end of the stent 200 can facilitate re-sheathing the stent 200 even when most of the stent 200 (e.g., except for the proximal-most portion thereof) has been deployed.

In the embodiments of FIGS. 26 and 27, any of the embodiments of the proximal device interface 180 and proximal engagement member 182 described herein (rotating, non-rotating, sliding, non-sliding, and any other varieties) can be employed.

Figure 28:
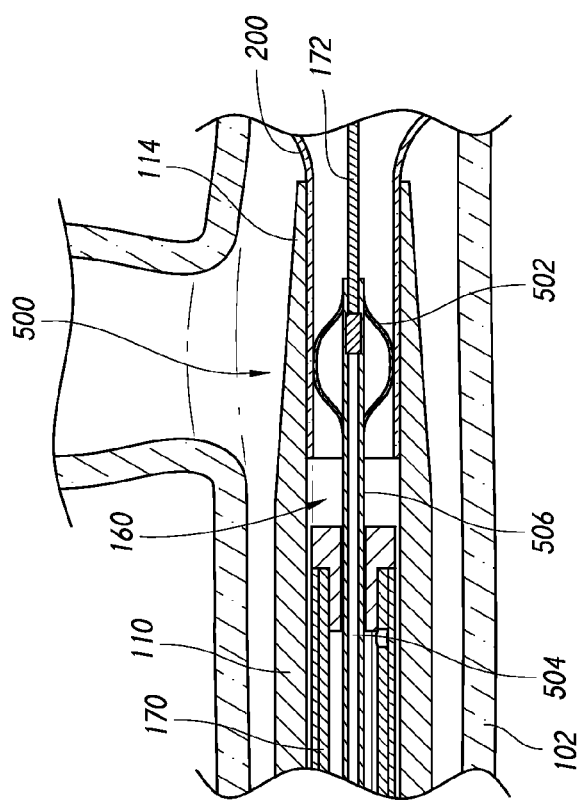
FIGS. 28 and 29 are side, cross-sectional views of device interfaces for providing enhanced proximal re-sheathing capability, according to some embodiments.
Figure 29:
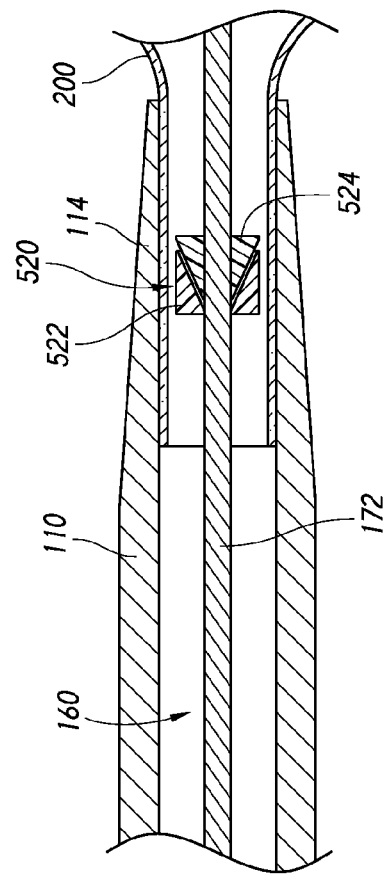

FIGS. 28 and 29 depict additional embodiments of proximal device interfaces 500, 520 that may be incorporated into the core assembly 140 of FIG. 26 to provide enhanced proximal re-sheathing capability. Accordingly, either of the interfaces 500, 520 can be incorporated in the core assembly 140 in a proximal portion of the stent 200, e.g., near the proximal end or in the proximal half of the stent 200. The device interfaces 500, 520 can be considered retraction-only interfaces in that they function only (or provide the option of functioning only) in a retraction or resheathing mode.

The interface 500 of FIG. 28 comprises a balloon 502 coupled to (e.g., mounted on) the core member 160 in a proximal portion of the stent 200. The balloon 502 can be kept deflated or otherwise disengaged with the stent 200 throughout operation of the core assembly 140 until it is desired to re-sheath the stent 200 or otherwise retract it proximally along the catheter 110. The balloon 502 can be inflated via an inflation lumen 504 to engage the inner surface of the stent 200, thereby gripping the stent 200 in cooperation with the catheter 110 in a manner similar to the engagement member 182. Upon so engaging or gripping the stent 200, the balloon 502 can be used to retract a partially-deployed stent 200 back into the catheter 110 by pulling the core member 160 proximally, in accordance with any of the re-sheathing methods described herein. The balloon 502 can be further employed to withdraw the stent 200 entirely from the catheter 110, or it can optionally be deflated and the stent 200 can be re-deployed using the proximal engagement member 182 (which has now re-engaged the retracted stent 200 so that the member 182 can urge the stent 200 distally from the catheter 110 in response to a distal push force applied to the core member 160). As yet another option, the balloon 502 can be kept deflated during distal advancement of the stent 200 through the catheter 110 until the distal end of the stent 200 is about to emerge from the distal end 114. At that point the balloon 502 can be inflated and both the balloon 502 and engagement member 182 can be used to push the stent 200 distally and deploy it. The balloon 502 can be employed to deploy the proximal portion of the stent 200, e.g., before and/or after the member 182 has emerged from the catheter 110 and become disengaged with the stent 200, while remaining available to re-sheath the stent 200 as described above.

The inflation lumen 504 can be incorporated into the core member 160 via an inflation tube 506 that passes through the lumen of the tube 170 and extends to the proximal end of the core member 160 (in which case the proximal wire 168 can be replaced with a similar length of hypotube). The distal portion of the inflation tube 506 can extend past the distal end of the tube 170 into the interior of the balloon 502. There, the tube 506 can be connected to a proximal end of the distal wire 172, which extends distally therefrom.

FIG. 29 depicts another embodiment of a retraction-only proximal device interface that can be incorporated in the core assembly 140 in a proximal portion of the stent 200, e.g., near the proximal end or in the proximal half of the stent 200. The interface 520 of FIG. 29 comprises a radially expanding member 522 that interacts with a wedge or cone 524 to expand radially, and engage an inner surface of the stent 200, only when the core member 160 is retracted. Accordingly, the interface 520 can remain in the radially contracted, non-engaging state shown in FIG. 29 (and therefore not transmit push force from the core member 160 to the stent 200) during distal advancement of the core assembly 140 and stent 200. When the stent 200 has been partially deployed, and it is desired to re-sheath the stent 200, the core member 160 can be retracted, causing the expanding member 522 to expand radially and engage the stent. The expanding member 522 thus can grip the stent 200 in cooperation with the catheter 110 in a manner similar to the engagement member 182. Upon so engaging or gripping the stent 200, the expanding member 522 can be used to retract a partially-deployed stent 200 back into the catheter 110 by pulling the core member 160 proximally, in accordance with any of the re-sheathing methods described herein. If desired, the expanding member 522 can be further employed to withdraw the stent 200 entirely from the catheter 110.

FIGS. 1, 5-9 and 12 depict some embodiments and methods of use of the medical device delivery system 100. First, the catheter 110 can be inserted into the patient's vasculature via a percutaneous access technique or other suitable method of access. The distal end 114 of the catheter 110 is then advanced to a treatment site or location in the blood vessel 102, using for example any of the access routes 400. The blood vessel 102 may comprise a vein or artery, such as an artery in a brain or within a cranium of the patient. As previously mentioned, the catheter 110 can comprise a microcatheter. A guide catheter (not shown) can be used instead of or in addition to the catheter 110; for example, the guide catheter can first be placed in the vasculature so that it extends part or all of the way to the treatment site and a microcatheter or other catheter then inserted through the guide catheter to the treatment site.

The treatment location may be near the aneurysm 108 formed in a wall of the blood vessel 102, and advancing the catheter 110 to the treatment location may include advancing the distal end 114 and/or distal opening 120 to a location that is distal of the aneurysm 108 (e.g., FIG. 5). Such advancement of the catheter 110 may include advancing the distal end 114 and/or distal opening 120 distally across the ostium or neck 106 of the aneurysm 108, to the location in the vessel 102 distal of the aneurysm.

Once the catheter 110 has been inserted, it may extend proximally from the distal end 114 and/or distal opening 120 at the treatment location, through the vascular access site, to the proximal end 112 and/or hub 122 which are preferably situated outside the patient's body.

After the catheter 110 has been placed, the core assembly 140 (with the stent 200 carried thereby) can be inserted, distal end first, into the lumen 116 of the catheter 110 via the hub 122 and/or proximal end 112. Where the core assembly 140 is initially at least partially contained within the introducer sheath 450 (FIGS. 22-25), the distal end of the introducer sheath 450 can be inserted into the proximal end of the catheter 110 and the core assembly 140 is advanced distally through the introducer sheath until the distal core assembly and stent 200 exit the distal end of the introducer sheath and pass into the lumen 116 of the catheter 110. Such advancement of the core assembly 140 can comprise gripping the core member 160 in the proximal grip region 462 as a result of its exposure proximal of the proximal end of the sheath 450 (and/or of the sheath 450 preventing the gripping of any other portion of the core assembly 140). When the core assembly 140 and stent have been sufficiently advanced, the introducer sheath 450 can be retracted from the proximal end of the catheter 110 and/or discarded. Once the sheath 450 has been so retracted/discarded, the proximal grip region 462 can be exposed for gripping proximal of the catheter proximal end 112, and the region 462 can be the only portion of the core assembly available for gripping by the user. (Other method steps, acts or functions disclosed herein with reference to FIGS. 22-25 can also optionally be performed in connection with the presently discussed method(s).)

The core assembly 140 and stent 200 are at this point disposed in the catheter 110 generally as depicted in FIG. 1. In particular, the stent 200 and distal portion of the core assembly 140 can be positioned in the lumen 116 of the catheter 110, with the stent 200 generally in contact with the inner surface 118 of the catheter 110 except where the first section 192a of the distal cover 192 is extending or interposed radially between the distal end 204 of the stent 200 and the inner surface 118 of the catheter 110. Further, the core member 160 can extend proximally of the proximal end 112 and/or hub 122 of the catheter 110 to a location outside of the patient's body, so that the proximal portions (e.g., proximal wire 168 where employed, and/or the proximal grip region 462) of the core member 160 can be easily accessed.

Next, the core assembly 140 with the stent 200 can be axially advanced distally within the lumen 116 of the catheter 110, toward the distal end 114 of the catheter 110 and treatment location. Where the core assembly 140 includes a proximal engagement member 182 and/or a distal cover 192 that can rotate about the core member 160, advancing the core assembly (in this method or in any method of advancing the core member 140 through a tortuous catheter, such as when such catheter is disposed in a laboratory model of vasculature) can further comprise rotating the stent 200, engagement member 182 and/or distal cover 192 about the core member 160. This can optionally be done without significant twisting of the core member 160 and/or stent 200.

Where the core assembly 140 includes one or more restraints 184, 194 and/or 196 having a tapered portion 250 (see FIG. 12), advancing the core assembly 140 (in this method or in any method of advancing the core member 140 through a tortuous catheter) can further comprise bending the core assembly 140 and core member 160 more sharply (and/or without the restraint 184, 194 and/or 196 contacting the inner surface of the stent 200) in the vessel 102 than would be possible with a non-tapered restraint 184, 194 and/or 196 of similar axial length and cross-sectional size or diameter.

Where the core member 160 includes a tube 170 with transition zones T3B, T3A, T2 and/or T1, advancing the core assembly 140 (in this method or in any method of advancing the core member 140 through a tortuous catheter) can further comprise forming a rounded, arc-like and/or non-kinking bend in the tube 170 in one or more of such transition zones T3B, T3A, T2 and/or T1, e.g., between the portions of the tube longitudinally adjacent to the transition zone(s) being so bent.

Where the core member 160 includes a tube 170 with flex zones Z4, Z3, Z2 and/or Z1, advancing the core assembly 140 (in this method or in any method of advancing the core member 140 through a tortuous catheter) can further comprise any one or combination of the following: advancing zone Z4 into or through the cavernous ICA, the carotid siphon, the M1 segment of the MCA, and/or the M2 segment of the MCA; advancing zone Z3 into the proximal portion of the ICA, proximal of the cavernous ICA, and/or into or through the common carotid artery; advancing zone Z2 into or through the aortic arch, and/or into any of the arteries originating at the arch and leading toward the neck; and/or advancing zone Z1 into the femoral artery and/or the abdominal aorta. The respective flex zone(s) can occupy one, some or all of the foregoing anatomical regions while the stent 200 is carried by the core assembly 140 and positioned in the M1 or M2 regions of the MCA, or while the intermediate portion 166 is in such location.

Where the core assembly 140 comprises a proximal device interface 180 and/or engagement member 182 positioned in a distal portion or half of the stent 200 (e.g., FIGS. 26-27), advancing the core assembly 140 (in this method or in any method of advancing the core member 140 through a tortuous catheter) can further comprise pulling the stent 200, or the proximal portions or proximal half thereof through the catheter 110 with the interface 180 and/or engagement member 182. This can optionally further comprise exerting less push force on the core member 160 than would be required in a similar delivery system that lacks a proximal device interface 180 and/or engagement member 182 positioned in a distal portion or half of the stent 200. Furthermore, if such a core assembly comprises a retraction-only interface in a proximal portion or half of the stent 200, advancing the core assembly can comprise doing so with the retraction-only interface disengaged from the stent.

As the stent 200 and distal cover 192 are advanced toward the distal end 114 and treatment location, the first section 192a of the distal cover 192 remains extending or interposed radially between the outer surface and/or distal end 204 of the stent 200 and the inner surface 118 of the catheter 110. Thus, the distal cover 192 may inhibit the distal end 204 of the advancing stent 200 (e.g., the filament ends thereof) from damaging, abrading, or gouging the catheter 110, and from thereby impeding progress of the stent 200 along the catheter 110. This may, in turn, avoid damage to the stent 200 such as by longitudinal compression resulting from high friction generated between the distal end 204 of the stent 200 and the catheter 110 while distally directed force is applied to the proximal portions of the stent 200.

Where the treatment location is near the aneurysm 108 and the distal end 114 and/or distal opening 120 of the catheter 110 has been advanced to a location that is distal of the aneurysm, advancement of the core assembly 140 with the stent 200 toward the distal end 114 and treatment location can include advancing the distal portion of the core assembly 140 and the distal end 204 of the stent 200 distally through the catheter 110 across the ostium or neck 106 of the aneurysm, to a location in the vessel 102 distal of the aneurysm.

As the stent 200 moves closer to the distal end of the catheter 110, the user can observe the fluorosafe marker 176 (when present) approaching the proximal end of the catheter and thereby recognize that the stent is or will soon be close to exiting the distal end of the catheter. Having recognized this, the user can activate fluoroscopic imaging to view the exit of the stent from the distal catheter end via such imaging, and then proceed to urge the core assembly distally and thereby cause the stent to exit the distal end of the catheter.

To begin expansion of the stent 200 (see FIGS. 5-9), the core assembly 140 may be held stationary and the catheter 110 may be withdrawn proximally over the stent 200 and distal portion of the core assembly 140, as shown in FIGS. 6-7. (Optionally, the core assembly and stent can be advanced distally while performing this step, instead of or in addition to withdrawal of the catheter.) Where the core assembly 140 comprises a selectively activatable interface such as the balloon 502 (FIG. 28) in a proximal portion or half of the stent 200, the interface can now be activated (e.g., the balloon now inflated and thereby changed from a deflated, disengaged condition to an inflated condition in which it engages the inner wall of the stent) to assist in urging the stent out of the catheter 110. In any event, as a result, the stent 200 (except for any portion retained within the catheter 110) can be released and permitted to expand into engagement with the inner wall of the blood vessel 102, as shown in FIGS. 6-7. Some embodiments of the stent 200 (such as certain braided stents) can shorten axially while expanding radially. As a result of (i) any axial foreshortening of the stent 200, (ii) radial expansion of the stent 200, and/or (iii) radial expansion of the distal cover 192 in response to radial expansion of the stent 200, the strips or tube portions of the first section 192a of the distal cover 192 can disengage from contact with the distal end 204 of the stent 200, while in some embodiments separating and moving radially outward as well.

As the distal portion of the stent 200 expands, it can cause the distal cover 192 to be opened or moved from the first orientation. When the stent 200 can foreshorten as it expands, the stent 200 can withdraw from engagement with the distal cover 192, as shown in FIG. 6. After the distal cover 192 has become disengaged from the stent 200 to reach the state shown in FIG. 6, the cover can proceed to the second orientation as shown in FIG. 7, as oncoming blood flow and/or other forces urge the first section 192a distally. Alternatively, the distal cover 192 can remain substantially in the disengaged, proximally-extending configuration shown in FIG. 6 until the core assembly 140 is withdrawn proximally into the catheter 110, at which point the distal end 114 of the catheter 110 can force the approaching first section 192a of the cover 192 to evert or otherwise take on the second configuration as shown in FIGS. 7-8.

In some embodiments, as the distal cover 192 disengages from the stent, it no longer covers the distal end 204 of the stent 200; instead, its first section 192a is now spaced distally from the stent distal end 204 as shown in FIG. 6. In this state, the strips or tube portions forming the first section 192a can be free or unconfined within the lumen of the blood vessel 102. As similarly noted above, the strips or tube portions can have free first ends, as well as second ends that are coupled to the core assembly 140. The free first ends can cover at least a portion of the stent distal portion during delivery of the stent. Further, when the stent is expanded and/or the core assembly 140 is proximally withdrawn into the catheter, the strips or tube portions can be everted, such that free first ends of the strips, wings, or elongate portions are drawn together distal to the second ends thereof.

The pullback of the catheter 110 (and/or distal movement of the core assembly 140) and expansion of the stent 200 may be done in multiple discrete steps. For example, the catheter 110 may initially be pulled back proximally only part of the way as shown in FIGS. 6-7, and only the distal portion 204 of the stent 200 expanded into engagement with the vessel wall. Such initial partial expansion facilitates anchoring the distal portion of the stent in the vessel 102, which in turn facilitates longitudinal stretching or compression of the stent 200 as desired by the clinician during or prior to expansion of the remaining portions of the stent 200 into the vessel 102. Initial partial expansion can also facilitate confirmation by the clinician that the distal portion of the stent 200 has "landed" in the desired location in the vessel 102 (e.g., distal of the neck or ostium of any aneurysm formed in the vessel wall) prior to expansion of the remaining portions of the stent 200. Generally, where an aneurysm is present in the vessel 102, proper placement of the stent 200 can include positioning a distal portion of the stent 200 in the vessel lumen distal of the aneurysm neck 106 and a proximal portion of the stent in the vessel lumen proximal of the aneurysm neck 106, such that the stent 200 extends across the neck (FIG. 9). Where the expanded stent 200 is appropriately configured, it may then perform a therapeutic flow-diverting function with respect to the aneurysm 108.

While the delivery system 100 is in the configuration shown in FIG. 6 or 7, with the proximal end 202 of the stent 200 retained within the catheter 110 between the proximal engagement member 182 and the inner wall 118 of the catheter, the partially expanded stent 200 can be resheathed or retracted proximally into the catheter 110 as shown in FIG. 8. The engagement member 182 and catheter 110 can secure, grip, or engage the stent 200 to a sufficient degree to permit the catheter 110 to be advanced distally over the partially expanded stent 200 (and/or the core member 160 withdrawn proximally relative to the catheter 110) until the stent 200 is again positioned in the lumen 116 of the catheter 110. Thus, the engagement member 182 can exert a proximal force on the stent 200 as the stent 200 is withdrawn or retracted into the catheter 110. Where the core assembly includes a retraction-only interface in a proximal half or portion of the stent (e.g., FIGS. 28-29), the retraction-only interface can be activated and employed to retract the stent proximally into the catheter 110. Thus, the retraction-only interface can exert a proximal force on the stent 200 as the stent 200 is withdrawn or retracted into the catheter 110.

FIGS. 6-7 also show a first aspect of a process of resheathing the stent 200, during or prior to the stent 204 being drawn into the lumen 116 of the catheter 110. Because the previously stent-engaging portion (e.g., the first section 192a) of the distal cover 192 has moved radially outward from the core member 160 (e.g., FIG. 6) and/or distally relative to the core member 160 (e.g., FIG. 7), it does not impede the entrance of the distal portion and distal end 204 of the stent 200 into the distal opening 120 of the catheter 110 (e.g., to get to the state shown in FIG. 8) during resheathing. Accordingly, the resheathing process can comprise moving the stent 200 (including the distal end 204) into the catheter 110 through the distal opening 120 while the previously stent-engaging portion (e.g., the first section 192a) of the distal cover 192 is in a second, everted, or resheathing configuration in which the stent-engaging portion is disposed radially outward from the core member 160 and/or the first section 192a of the distal cover 192 is disposed distally relative to the core member 160, the second section 192b, and/or the distal tip 165, in comparison to a first, encapsulating, or delivery configuration (e.g., FIG. 1, 3) of the stent-engaging portion (e.g., the first section 192a) of the distal cover 192.

FIG. 8 shows a second aspect of the resheathing process currently under discussion. In this aspect of the process, the core assembly 140 can be moved further proximally into the catheter 110 (and/or the catheter 110 is moved further distally over the core assembly 140) until the distal cover 192 enters the catheter 110 via the distal opening 120. As noted above, the first section 192a of the distal cover 192 is preferably sufficiently flexible to evert and thereby attain the second, everted, or resheathing configuration shown in FIGS. 7-8. In the second, everted, or resheathing configuration, the first section 192a of the distal cover 192 can extend generally in a distal direction, away from the stent 200, and/or extend distally of the second section 192b of the distal cover 192. Further, in some embodiments, the first section 192a of the distal cover 192 can also radially overlap the distal tip 165 and/or the distal restraint 196. Instead of or in addition to these aspects of the second, everted, or resheathing configuration, the distal cover 192 can be radially small enough to extend into the lumen 116 of the catheter 110, either partially or wholly as shown in FIG. 8, and/or the entire distal cover 192 can be spaced distally from the distal end 204 of the stent 200 in the lumen 116 of the catheter 110.

Accordingly, in accordance with some embodiments of methods disclosed herein, when operating the delivery system 100, a clinician can check the initial partial expansion of the stent 200 (e.g., as shown in FIGS. 6-7) and, if the initial placement is unsatisfactory or if the initial expansion of the stent 200 is unsatisfactory, the clinician can recapture, collapse, withdraw, or resheath the stent 200 into the catheter 110, as described above with respect to FIGS. 6-8. After resheathing, the clinician can attempt to deploy the stent again, as described herein, beginning for example with the state depicted in FIG. 8, and resulting for example, in the state depicted in FIG. 6-7 or 9. Resheathing can also be performed, and the delivery system 100 and stent 200 removed from the patient entirely, if for example, the delivery and/or expansion of the stent 200 damages or reveals a defect in, or improper sizing of, the stent 200 or delivery system 100. After an initial partial expansion of the stent 200, the depicted core assembly 140 can optionally be entirely removed with the stent 200 from the catheter 110 without need to remove the catheter 110 from the blood vessel 102. In this manner, access to the treatment site in the blood vessel 102 can be maintained via the catheter 110 and, if desired, additional attempts to deliver the stent 200 can be made through the catheter 110.

If the initial expansion of the stent 200 in the vessel 102 is satisfactory, full deployment and expansion can be completed to result in the state depicted in FIG. 9. The proximal end 202 of the stent 200 may be released from the catheter 110 by holding the core member 160 stationary and withdrawing the catheter proximally relative to the core member 160 and the stent 200 until the distal opening 120 is proximal of the proximal end 202 of the stent 200. No longer constrained by the catheter 110, the proximal end 202 of the stent 200 can now expand into contact with the wall of the vessel 102, as shown FIG. 9. (Note that until this point, according to an aspect of some embodiments, the partially expanded stent 200 had been fully resheathable.) The fully deployed stent 200 extends across the neck 106 of the aneurysm 108, and can optionally perform a therapeutic flow-diverting function with respect to the aneurysm.

Following full expansion of the stent 200, the core assembly 140 can be drawn back into the catheter 110. Both the catheter 110 and core assembly 140 can be withdrawn from the patient, either simultaneously or sequentially. However, when the stent has been successfully released, the core assembly 140 can also be entirely removed from the catheter 110, with the catheter 110 remaining in place, and a second core assembly can be inserted into the catheter lumen. The second core assembly can be configured to deliver a second stent to the treatment site in order to perform, e.g., a telescoping procedure.

In the present disclosure, numerous references are made to moving the catheter 110 axially over the core assembly 140, and moving the core assembly 140 axially within the catheter 110. Except where specifically noted to the contrary, all such references to one form of this relative movement should be understood to include the other as an alternative.

Information regarding additional embodiments of the medical device delivery system 100, and additional details, components and methods that can optionally be used or implemented in or with the embodiments of the delivery system 100 described herein, can be found in U.S. patent application Ser. No. 13/664,547, filed on Oct. 31, 2012, titled METHODS AND APPARATUS FOR LUMINAL STENTING, the entirety of which is hereby incorporated by reference herein and made a part of this specification. The delivery system 100 and methods disclosed herein can optionally be similar to any of the delivery systems or methods disclosed in the above-incorporated application, except as further described herein.

The apparatus and methods discussed herein are not limited to the deployment and use of a medical device or stent within the vascular system but may include any number of further treatment applications. Other treatment sites may include areas or regions of the body including any hollow anatomical structures.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A stent delivery system, comprising:
a core member having a distal segment;
a stent engagement member having a generally tubular body positioned about the core member distal segment and rotatably coupled to the core member, the engagement member comprising an inner layer having a first durometer and an outer layer comprising silicone and having a second durometer less than the first durometer, the outer layer defining a cylindrical smooth outer surface; and a stent extending along the core member distal segment such that an inner surface of the stent is engaged by the engagement member outer layer for facilitating rotation of the stent relative to the core member, wherein the stent engagement member has a length of less than 5 mm.

2. The system of claim 1, wherein the inner layer comprises a substantially cylindrical inner surface surrounding the core member.

3. The system of claim 1, wherein the inner layer comprises polyimide.

4. The system of claim 1, wherein the stent is a self-expanding stent.

5. The system of claim 1, wherein the stent is moveable within a tubular component by virtue of engagement with the engagement member.

6. The system of claim 1, wherein the outer layer comprises a durometer of between about 10 A to about 50 A.

7. The system of claim 6, wherein the outer layer comprises a durometer of between about 15 A to about 40 A.

8. The system of claim 7, wherein the outer layer comprises a durometer of about 20 A.

9. The system of claim 1, further comprising a sheath having a lumen configured to receive the core member, engagement member, and stent, wherein the stent is radially compressed between an inner surface of the sheath and the engagement member outer layer.

10. The system of claim 9, wherein friction between the engagement member and the stent is greater than friction between the sheath inner surface and the stent.

11. A stent delivery system, comprising:

a core member having a distal segment;

a stent engagement member positioned about the core member distal segment and rotatably coupled to the core member, the engagement member comprising an inner layer and an outer layer, the outer layer comprising silicone and having a durometer of less than 50 A, and the outer layer defining a cylindrical smooth outer surface; and a stent extending along the core member distal segment such that an inner surface of the stent is engaged by the engagement member outer layer for facilitating rotation of the stent relative to the core member, wherein the stent engagement member has a length less of than 5.0 mm.

12. The system of claim 11, wherein the inner layer comprises a substantially cylindrical inner surface surrounding the core member.

13. The system of claim 11, wherein the inner layer comprises a durometer of between about 70 A to about 100 A.

14. The system of claim 11, wherein the inner layer comprises polyimide.

15. The system of claim 1, wherein the outer layer has a durometer of less than 50 A.

16. The system of claim 11, wherein the outer layer comprises a durometer of between about 10 A to about 50 A.

17. The system of claim 16, wherein the outer layer comprises a durometer of between about 15 A to about 40 A.

18. The system of claim 17, wherein the outer layer comprises a durometer of about 20 A.

* * * * *